United States Patent
Yang et al.

(10) Patent No.: US 11,667,919 B2
(45) Date of Patent: Jun. 6, 2023

(54) TARGETING CANCER-ASSOCIATED LONG NON-CODING RNAS

(71) Applicant: University of Pittsburgh—Of the Commonwealth System of Higher Education, Pittsburgh, PA (US)

(72) Inventors: Da Yang, Pittsburgh, PA (US); Zehua Wang, Pittsburgh, PA (US)

(73) Assignee: University of Pittsburgh—of the Commonwealth System of Higher Education, Pittsburgh, PA (US)

(*) Notice: Subject to any disclaimer, the term of this patent is extended or adjusted under 35 U.S.C. 154(b) by 336 days.

(21) Appl. No.: 16/970,845

(22) PCT Filed: Feb. 22, 2019

(86) PCT No.: PCT/US2019/019155
§ 371 (c)(1),
(2) Date: Aug. 18, 2020

(87) PCT Pub. No.: WO2019/165212
PCT Pub. Date: Aug. 29, 2019

(65) Prior Publication Data
US 2021/0115441 A1    Apr. 22, 2021

Related U.S. Application Data

(60) Provisional application No. 62/633,828, filed on Feb. 22, 2018.

(51) Int. Cl.
*C12N 15/113* (2010.01)
*A61K 31/551* (2006.01)
*A61K 31/5517* (2006.01)
*A61K 31/7088* (2006.01)
*C12Q 1/6886* (2018.01)

(52) U.S. Cl.
CPC .......... *C12N 15/113* (2013.01); *A61K 31/551* (2013.01); *A61K 31/5517* (2013.01); *A61K 31/7088* (2013.01); *C12Q 1/6886* (2013.01); *C12N 2310/14* (2013.01); *C12N 2320/31* (2013.01); *C12Q 2600/106* (2013.01); *C12Q 2600/154* (2013.01)

(58) Field of Classification Search
CPC .............. C12N 15/113; C12N 2310/14; C12N 2320/31; C12Q 2600/178; A61P 35/00
USPC ........... 435/6.1, 6.11, 91.1, 91.31, 455, 458; 514/44 A; 536/23.2, 24.5
See application file for complete search history.

(56) References Cited

U.S. PATENT DOCUMENTS

| 5,032,401 A | 7/1991 | Jamas et al. |
| 5,607,677 A | 3/1997 | Jamas et al. |
| 7,618,814 B2 * | 11/2009 | Bentwich ............... G16B 20/30 536/24.31 |
| 7,737,265 B2 | 6/2010 | Akinc et al. |
| 8,101,348 B2 | 1/2012 | Tuschl et al. |
| 8,178,503 B2 * | 5/2012 | Rigoutsos ............... G16B 20/20 514/44 A |
| 10,822,659 B2 * | 11/2020 | Cao ..................... C12Q 1/6883 |
| 2005/0281781 A1 | 12/2005 | Ostroff |
| 2016/0271163 A1 * | 9/2016 | Marine ............. G01N 33/5743 |
| 2017/0081667 A1 | 3/2017 | Chen et al. |
| 2018/0346988 A1 * | 12/2018 | French ................ A61K 31/713 |

FOREIGN PATENT DOCUMENTS

| WO | 2016209862 A1 | 12/2016 |
| WO | 2017047102 A1 | 3/2017 |

OTHER PUBLICATIONS

Yang et al (Abstract 3495, AACR Annual Meeting Apr. 1-5, 2017, Molecular and Cellular Biology, Genetics, Publ. Jul. 2017) (Year: 2017).*
And Hamilton et al (AIMS Biophys., vol. 2, No. 4, pp. 794-809 (2015)) (Year: 2015).*
Agrelo et al., SATB1 Defines the Developmental Context for Gene Silencing by Xist in Lymphoma and Embryonic Cells, Developmental Cell, Apr. 21, 2009, pp. 507-516, vol. 16, DOI: 10.1016/j.devcel.2009.03.006.
Amati et al., Oncogenic Activity of the c-Myc Protein Requires Dimerization with Max, Cell, Jan. 29, 1993, pp. 233-245, vol. 72.
Amin et al., Epigenomic footprints across 111 reference epigenomes reveal tissue-specific epigenetic regulation of lincRNAs, Nature Communications, 2015, vol. 6, No. 6370, DOI: 10.1038/ncomms7370.
Barretina et al., The Cancer Cell Line Encycolpedia enables predictive modelling of anticancer drug sensitivity, Nature, Mar. 29, 2012, pp. 603-607, vol. 483, DOI: 10.1038/nature11003.
Batista et al., Long-Noncoding RNAs: Cellular Address Codes in Development and Disease, Cell, Mar. 14, 2013, pp. 1298-1307, vol. 152, DOI: 10.1016/j.cell.2013.02.012.
Baylin et al., DNA Methylation Patterns of the Calcitonin Gene in Human Lung Cancers and Lymphomas, Cancer Research, Jun. 1986, pp. 2917-2922, vol. 46.
Blackwood et al., Max: A Helix-Loop-Helix Zipper Protein That Forms a Sequence-Specific DNA-Binding Complex with Myc, Science, Mar. 8, 1991, vol. 251, No. 4998.
Cawley et al., Unbiased Mapping of Transcription Factor Binding Sites along Human Chromosomes 21 and 22 Points to Widespread Regulation of Noncoding RNAs, Cell, Feb. 20, 2004, pp. 499-509, vol. 116.
Chen et al., Diffrential Effects on ARF Stability by Normal versus Oncogenic Levels of c-Myc Expression, Molecular Cell, Jul. 11, 2013, pp. 46-56, vol. 51, DOI: 10.1016/j.molcel.2013.05.006.
Corey, Chemical Modification: the key to clinical application of RNA interference?, J Clin Invest., 2007, pp. 3615-3622, vol. 117, No. 12, DOI: 10.1172/JCI334483.

(Continued)

*Primary Examiner* — Jane J Zara
(74) *Attorney, Agent, or Firm* — The Webb Law Firm

(57) ABSTRACT

Methods of treating cancer are provided along with nucleic acids and nucleic acid analog sequences of a long-non-coding RNA (lncRNA), and reagents useful for knocking down the lncRNA.

20 Claims, 16 Drawing Sheets

Specification includes a Sequence Listing.

(56) References Cited

OTHER PUBLICATIONS

Cunningham et al., New Connections between Old Pathways: PDK1 Signaling Promotes Cellular Transformation through PLK1-Dependent MYC Stabilization, Cancer Discovery, Oct. 2013, pp. 1099-1102, DOI: 10.1158/2159-8290.CD-13-0581.

Dang et al., MYC-Induced Cancer Cell Energy Metabolism and Therapeutic Opportunities, Clin Cancer Res, Nov. 1, 2009, pp. 6479-6483, vol. 15, No. 21, DOI: 10.1158/1078-0432.CCR-09-0889.

Djebali et al., Landscape of transcription in human cells, Nature, Sep. 6, 2012, pp. 101-108, vol. 489, DOI: 10.1038/nature11233.

Doose et al., MINCR is a MYC-induced lncRNA able to modulate MYC's transcriptional network in Burkitt lymphoma cells, PNAS, Sep. 15, 2015, E5261-E5270, DOI: 10.1073/pnas.1505753112.

Du et al., Integrative genomic analyses reveal clinically relevant long noncoding RNAs in human cancer, Nature Structural & Molecular Biology, Jul. 2013, pp. 908-913, vol. 20, No. 7, DOI: 10.1038/nsmb.2591.

Du et al., Integrative analyses reveal a long noncoding RNA-mediated sponge regulatory network in prostate cancer, Nature Communications, Mar. 15, 2016, vol. 7, No. 10982, DOI: 10.1038/ncomms10982.

Fernandez et al., Genomic targets of the human c-Myc protein, Genes & Development, 2003, pp. 1115-1129, vol. 17, DOI: 10.1101/gad.1067003.

Gartel et al., Myc represses the p21 (WAF1/CIP1) promoter and interacts with Sp1/Sp3, PNAS, Apr. 10, 2001, pp. 4510-4515, vol. 98, No. 8, DOI: 10.1073ypnas.081074898.

Gartel et al., Lost in Transcription: p21 Repression, Mechanisms, and Consequences, Cancer Res, May 15, 2005, pp. 3980-3985, vol. 65, No. 10.

Guo et al., Modulation of long noncoding RNAs by risk SNPs underlying genetic predispositions to prostate cancer, Nature Genetics, Oct. 2016, pp. 1142-1150, vol. 48, No. 10, DOI: 10.1038/ng.3637.

Gupta et al., Long noncoding RNA HOTAIR reprograms chromatin state to promote cancer metastasis, Nature, Apr. 15, 2010, pp. 1071-1076, vol. 464, No. 7291, DOI: 10.1038/nature08975.

Guttman et al., Chromatin signature reveals over a thousand highly conserved large non-coding RNAs in mammals, Nature, Mar. 12, 2009, pp. 223-227, vol. 458, No. 7235, DOI: 10.1038/naure07672.

Hamilton et al., The Interplay of long non-coding RNAs and MYC in cancer, AIMS Biophys., 2015, pp. 794-809, vol. 2, No. 4, DOI: 10.3934/biophy.2015.4.794.

Hancock et al., A CTCF-binding silencer regulates the imprinted genes AWT1 and WT1-AS and exhibits sequential epigenetic defects during Wilms' tumourigenesis, Human Molecular Genetics, 2007, pp. 343-354, vol. 16, No. 3, DOI: 10.1093/hmg/ddl478.

Hu et al., A Functional Genomic Approach Identifies FAL1 as an Oncogenic Long Noncoding RNA that Associates with BMI1 and Represses p21 Expression in Cancer, Cancer Cell, Sep. 8, 2014, pp. 344-357, vol. 26, DOI: 10.1016/j.ccr.2014.07.009.

Hung et al., A long noncoding RNA connects c-Myc to tumor metabolism, PNAS, Dec. 30, 2014, pp. 18697-18702, vol. 111, No. 52, DOI: 10.1073/pnas.1415669112.

Irizarry et al., The human colon cancer methylome shows similar hypo- and hypermethylation at conserved at conserved tissue-specific CpG island shores, Naure Genetics, Feb. 2009, pp. 178-186, vol. 41, No. 2, DOI: 10.1038/ng.298.

Iyer et al., The landscape of long noncoding RNAs in the human transcriptome, Nature Genetics, Mar. 2015, pp. 199-208, vol. 47, No. 3, DOI: 10.1038/ng.3192.

Izumi et al. Mechanism for the transcriptional repression by c-MYc on PDGF β-receptor, Journal of Cell Science, 2001, pp. 1533-1544, vol. 114.

Jones et al., The Fundamental Role of Epigenetic Events in Cancer, Nature Reviews Genetics, Jun. 2002, pp. 415-428, vol. 3, DOI: 10.1038/nrg816.

Kim et al., An Extended Transcriptional Network for Pluripotency of Embryonic Stem Cells, Cell, Mar. 21, 2008, pp. 1049-1061, vol. 132, DOI: 10.1016/j.cell.2008.02.039.

Lee et al., Cell-type specific and combinatorial usage of diverse transcription factors revealed by genome-wide binding studies in multiple human cells, Genome Research, 2012, pp. 9-24, vol. 22, DOI: 10.1101/gr.127597.111.

Lee et al., Noncoding RNA NORAD Regulates Genomic Stability by Sequestering PUMILIO Proteins, Cell, 2016, pp. 69-80, vol. 164, DOI: 10.1016/j.cell.2015.12.017.

Lehmann et al., Identification of human triple-negative breast cancer subtypes and preclinical models for selection of targeted therapies, J Clin Invest, 2011, pp. 2750-2767, vol. 121, No. 7, DOI: 10.1172/JCI45014.

Leucci et al., Melanoma addition to the long non-coding RNA SAMMSON, Nature, Mar. 24, 2016, pp. 518-522, vol. 531, DOI: 10.1038/nature17161.

Li et al., A global transcriptional regulatory role for c-Myc in Burkitt's lymphoma cells, PNAS, Jul. 8, 2003, pp. 8164-8169, vol. 100, No. 14, DOI: 10.1073ypnas.1332764100.

Li et al., Functional and molecular interactions between the HGF/c-Met pathway and c-Myc in large-cell medulloblastoma, Laboratory Investigation, 2008, pp. 98-111, vol. 88, DOI: 10.1038/labinvest.3700702.

Li et al., Microarray expression profile of long noncoding RNAs in human osteosarcoma, Biochemical and Biophysical Research Communications, 2013, pp. 200-206, No. 433, DOI: 10.1016/j.bbrc.2013.02.083.

Lima et al., Single-Stranded siRNAs Activate RNAi in Animals, Cell, Aug. 31, 2012, pp. 883-894, vol. 150, DOI: 10.1016/j.cell.2012.08.014.

Ling et al., CCAT2, a novel noncoding RNA mapping to 8q24, underlies metastatic progression and chromosomal instability in colon cancer, Genome Research, 2013,pp. 1446-1461, vol. 23, DOI: 10.1101/gr.152942.112.

Lüscher, Function and regulation of the transcription factors of the Myc/Max/Mad network, Gene, 2001, pp. 1-14, vol. 277.

Marques Howarth et al., Long noncoding RNA EWSAT1-mediated gene repression facilitates Ewing sarcoma oncogenesis, J Clin Invest, 2014, pp. 5275-5290, vol. 124, No. 12, DOI: 10.1172/JCI72124.

Mohammad et al., Kcnq1ot1/Lit1 Noncoding RNA Mediates Transcriptional Silencing by Targeting to the Perinucleolar Region, Molecular and Cellular Biology, Jun. 2008, p. 3713-3728, vol. 28, No. 11, DOI: 10.1128/MCB.02263-07.

Mondal et al., MEG3 long noncoding RNA regulates the TGF-β pathway genes through formation of RNA-DNA triplex structures, Nature Communications, 2015, vol. 6, No. 7743, DOI: 10.1038/ncomms8743.

Mukherjee et al., c-Myc Suppresses p21 WAF1/CIP1 Expression during Estrogen Signaling and Antiestrogen Resistance in Human Breast Cancer Cells, The Journal of Biological Chemistry, May 6, 2005, pp. 17617-17625, vol. 280, No. 18, DOI: 10.1074/jbc.M502278200.

Noushmehr et al., Identification of a CpG Island Methylator Phenotype that Defines a Distinct Subgroup of Glioma, Cancer Cell, May 18, 2010, pp. 510-522, vol. 17, DOI: 10.1016/j.ccr.2010.03.017.

Pandey et al., Kcnq1ot1 Antisense Noncoding RNA Mediates Lineage-Specific Transcriptional Silencing through Chromatin-Level Regulation, Molecular Cell, Oct. 24, 2008, pp. 232-246, vol. 32, DOI: 10.1016/j.molcel.2008.08.022.

Perou et al., Molecular portraits of human breast tumours, Nature, Aug. 17, 2000, pp. 747-752, vol. 406.

Peukert et al., An alternative pathway for gene regulation by Myc, The EMBO Journal, 1997, pp. 5672-5686, vol. 16, No. 18.

Plass et al., Restriction landmark genome scanning for aberrant methylation in primary refractory and relapsed acute myeloid leukemia; involvement of the WIT-1 gene, Oncogene, 1999, pp. 3159-3165, vol. 18.

Presner et al., The Emergence of lncRNAs in Cancer Biology, Cancer Discovery, Oct. 2011, pp. 391-407, DOI: 10.1158/2159-8290.CD-11-0209.

(56) References Cited

OTHER PUBLICATIONS

Raabe et al., High-Risk Medulloblastoma: Does c-myc Amplification Overrule Histopathology?, Pediatr Blood Cancer, Mar. 2010, pp. 344-345, vol. 54, No. 3, DOI: 10.1002/pbc.22398.
Reon et al., Expression of lncRNAs in Low-Grade Gliomas and Glioblastoma Multiforme: An In Silico Analysis, PLOS Medicine, Dec. 6, 2016, DOI: 10.1371/journal.pmed.1002192.
Rinn et al., Functional Demarcation of Active and Silent Chromatin Domains in Humas HOX Loci by Noncoding RNAs, Cell, Jun. 29, 2007, pp. 1311-1323, vol. 129, DOI: 10.1016/j.cell.2007.05.022.
Roy et al., Direct role for Myc in transcription initiation mediated by interactions with TFII-I, Nature, Sep. 23, 1993, pp. 359-361, vol. 365.
Ruan et al., Long non-coding RNA small nucleolar RNA host gene 12 (SNHG12) promotes cell proliferation and migration by unregulating angiomotin gene expression in human osteosarcoma cells, Tumor Biol., 2016, pp. 4065-4073, vol. 37, DOI: 10.1007/s13277-015-4256-7.
Sanchez et al., Genome-wide analysis of the human p53 transcriptional network unveils a lncRNA tumour suppressor signature, Nature Communications, 2014, vol. 5, No. 5812, DOI: 10.1038/ncomms6812.
Schmitt et al., Long Noncoding RNAs in Cancer Pathways,Cancer Cell, Apr. 11, 2016, pp. 452-463, vol. 29, DOI: 10.1016/j.ccell.2016.03.010.
Schmitt et al., An inducible long noncoding RNA amplifies DNA damage signaling, Nature Genetics, Nov. 2016, pp. 1370-1376, vol. 48, No. 11, DOI: 10.1038/ng.3673.
Scott et al., Constitutional 11p15 abnormalities, including heritable imprinting center mutations, cause nonsyndromic Wilms tumor, Nature Genetics, Nov. 2008, pp. 1329-1334, vol. 40, No. 11, DOI: 10.1038/ng.243.
Sengupta et al., Cyclin dependent kinase-9 mediated transcriptional de-regulation of cMYC as a critical determinant of endocrine-therapy resistance in breast cancers, Breast Cancer Res Treat, 2014, pp. 113-124, vol. 143, DOI: 10.1007/s10549-013-2789-2.
Shen et al., Interplay between the Cancer Genome and Epigenome, Cell, Mar. 28, 2013, pp. 38-55, vol. 153, DOI: 10.1016/j.cell.2013.03.008.
Shlyueva et al., Transcriptional enhancers: from properties to genome-wide predictions, Nature, Apr. 2014, pp. 272-286, vol. 15, DOI: 10.1038/nrg3682.
Shrivastava et al., Inhibition of Transcriptional Regulator Yin-Yan-1 by Association with c-Myc, Science, Dec. 17, 1993, pp. 1889-1892, vol. 262, No. 5141.
Stearns et al., c-Myc Overexpression Causes Anaplasia in Medulloblastoma, Cancer Res, Jan. 15, 2006, pp. 673-681, vol. 66, No. 2, DOI: 10.1158/0008-5472.CAN-05-1580.
Subramanian et al., Gene set enrichment analysis: A knowledge-based approach for interpreting genome-wide expression profiles, PNAS, Oct. 25, 2005, pp. 15545-15550, vol. 102, No. 43, DOI: 10.1073ypnas.0506580102.
Tavana et al., HAUSP deubiquitinates and stabilizes N-Myc in neuroblastoma, Nature Medicine, Oct. 2016, pp. 1180-1186, vol. 22, No. 10, DOI: 10.1038/nm.4180.
The Cancer Genome Atlas Network, Comprehensive molecular portraits of human breast tumours, Nature, Oct. 4, 2012, pp. 61-70, vol. 490, DOI: 10.1038/nature11412.
The Cancer Genome Atlas Research Network, Comprehensive molecular profiling of lung adenocarcinoma, Nature, Jul. 31, 2014, pp. 543-550, vol. 511, DOI: 10.1038/nature13385.
The Encode Project Consortium, An Integrated Encyclopedia of DNA Elements in the Human Genome, Nature, Sep. 6, 2012, pp. 57-74, vol. 489, No. 7414, DOI: 10.1038/nature11247.
Tseng et al., PVT1 dependence in cancer with MYC copy-number increase, Nature, Aug. 7, 2014, pp. 82-86, vol. 512, DOI:10.1038/nature13311.

Vennstrom et al., Isolation and Characterization of c-myc, a Cellular Homolog of the Oncogene (v-myc) of Avian Myelocytomatosis Virus Strain 29, Journal of Virology, Jun. 1982, pp. 773-779, vol. 42, No. 3.
Verma et al., Transcriptome sequencing reveals thousands of novel long non-coding RNAs in B cell lymphoma, Genome Medicine, 2015, vol. 7, No. 110, DOI: 10.1186/s13073-015-0230-7.
Vogelstein et al., Cancer Genome Landscapes, Science, Mar. 29, 2013, pp. 1546-1558, vol. 330, DOI: 10.1126/science.1235122.
Von Der Lehr et al., The F-Box Protein Skp2 Participates in c-Myc Proteosomal Degradation and Acts as a Cofactor for c-Myc-Regulated Transcription, May 2003, pp. 1189-1200, vol. 11.
Wang et al., LncRNA MALAT1 enhances oncogenic activities of EZH2 in castration-resistant prostate cancer, Oncotarget, Oct. 15, 2015, pp. 41045-41055, vol. 6, No. 38.
Wang et al., Systematic identification of non-coding pharmacogenomic landscape in cancer, Nature Communications, 2018, vol. 9, No. 3192, DOI: 10.1038/s41467-018-05495-9.
Wang et al., lncRNA Epigenetic Landscape Analysis Identifies EPIC1 as an Oncogenic lncRNA that Interacts with MYCand Promotes Cell-Cycle Progression in Cancer, Cancer Cell, 2018, pp. 706-720, vol. 33, DOI: 10.1016/j.ccell.2018.03.006.
Watts et al., Gene silencing by siRNAs and antisense oligonucleotides in the laboratory and the clinic, J Pathol, Jan. 2012, pp. 365-379, vol. 226, No. 2, DOI: 10.1002/path.2993.
Wijnen et al., KCNQ1OT1 Hypomethylation: A Novel Disguised Genetic Predisposition in Sporadic Pediatric Adrenocortical Tumors?, Pediatr Blood Cancer, 2012, pp. 565-566, vol. 59, DOI: 10.1002/pbc.23398.
Wu et al., Role of H3K27 methylation in the regulation of lncRNA expression, Cell Research, 2010, pp. 1109-1116, vol. 20, DOI: 10.1038/cr.2010.114.
Wu et al., Improved siRNA/shRNA Functionality by Mismatched Duplex, PLoS ONE, Dec. 2011, e28580, vol. 6, No. 12, DOI: 10.1371/journal.pone.0028580.
Xiang et al., Human colorectal cancer-specific CCAT1-L lncRNA regulates long-range chromatin interactions at the MYC locus, Cell Research, 2014, pp. 513-531, vol. 24, DOI: 10.1038/cr.2014.35.
Xu et al., MYC and Breast Cancer, Genes & Cancer, pp. 629-640, vol. 1, No. 6, DOI: 10.1177/1947601910378691.
Yan et al., Comprehensive Genomic Characterization of Long Non-coding RNAs across Human Cancers, Cancer Cell, 2015, pp. 529-540, vol. 28, DOI: 10.1016/j.ccell.2015.09.006.
Yang et al., Long non-coding RNA GHET1 promotes gastric carcinoma cell proliferation by increasing c-Myc mRNA stability, FEBS Journal, 2014, pp. 802-813, vol. 281, DOI: 10.1111/febs.12625.
Yang et al., The DNA methylation landscape of long non-coding RNAs in human cancer [abstract]. In: Proceedings of the American Association for Cancer Research Annual Meeting 2017 Washington, DC., Apr. 1-5, 2017,, Abstract 3495, DOI: 10.1158/1538-7445.AM2017-3495.
Zeller et al., Global mapping of c-Myc binding sites and target gene networks in human B cells, PNAS, Nov. 21, 2006, pp. 17834-17839, vol. 103, No. 47, DOI: 10.1073ypnas.0604129103.
Zhang et al., Maternally Expressed Gene 3 (MEG3) Noncoding Ribonucleic Acid: Isoform Structure, Expression, and Functions, Endocrinology, Mar. 2010, pp. 939-947, vol. 151, No. 3, DOI: 10.1210/en.2009-0657.
Zhao et al., Genome-wide Identification of Polycomb-Associated RNAs by RIP-seq, Molecular Cell, Dec. 22, 2010, pp. 939-953, vol. 40, DOI: 10.1016/j.molcel.2010.12.011.
Zhou et al., MEG3 noncoding RNA: a tumor suppressor, Journal of Molecular Endocrinology, 2012, pp. R45-R53, vol. 48, DOI: DOI: 10.1530/JME-12-0008.
Zhu et al., Genome-scale deletion screening of human long non-coding RNAs using a paired-guide RNA CRISPR-Cas9 library, Nature Biotechnology, Dec. 2016, pp. 1279-1286, vol. 34, No. 12, DOI: 10.1038/nbt.3715.

* cited by examiner

>*EPIC1 v1 (SEQ ID NO: 1)*
AGTCCGCCATTGCAAACACGAAGCTCTTCCAGAAACGCCCTCACAGACACCCCGGAAGTCACGTACCC
ACTCTGTAGGTGCCCCGGGGCACAGGCAAGCGGACGAGCCAGTTATCCCTCAGAGCTCCTGCTGCCTC
GCCCGCTTTCTCTCGGAAACGTGAAGTGTGGCCTCAGCTGAAAGTGAGGTGGGCCTCATTCAATCAGT
TGAATTCTTCAAGAGAGAAAAACTGAAGTCCCTTAGAAGGAAAGAGTTCTGCCTTCAGACTGTCTTTG
AACTTAAGACTGTAGCGTCGACTCCTGCCGGAATTTCCAGCCTGCTGGCCAGCTCTGCAGATTCACAC
TTGCCAGCCTCCACAATCGTGTGAGCCAATTCCTTAACTTCTCTTTCTCCGTGTATCCCTTTGGTGCT
GCCTCTCTGGGGAGCCCTGACTAATATGCATGCAGATGATACGGTGCCTGGCATTCTGAATACATGCA
CTAAATCCACCACTTTTCCCCATTTATAGATTTGGATTAACACACTAACTTACTCATATCTGCAAGTA
TAAATAAAAAAAATTGCTGGTGC
>*EPIC1 v2 (SEQ ID NO: 2)*
AGTCCGCCATTGCAAACACGAAGCTCTTCCAGAAACGCCCTCACAGACACCCCGGAAGTCACGTACCC
ACTCTGTAGGTGCCCCGGGGCACAGGCAAGCGGACGAGCCAGTTATCCCTCAGAGCTCCTGCTGCCTC
GCCCGCTTTCTCTCGGAAACGTGAAGTGTGGCCTCAGCTGAAAGTGAGGTGGGCCTCATTCAATCAGT
TGAATTCTTCAAGAGAGAAAAACTGAAGTCCCTTAGAAGGAAAGAGTTCTGCCTTCAGACTGTCTTTG
AACTTAAGACTGTAGCGTCGACTCCTGCCGGAATTTCCAGCCTGCTGGCCAGCTCTGCAGATTCACAC
TTGCCAGCCTCCACAATCTTCCTGGATTTGAAACTGAAGAAGCAAGCAATCTGGAAATGTCAGTGGAT
GCACACAAAGAAACAACCGCAAAAGCCTGCTCGCTCTAGCCAAGGGACAAGAATAGGGGCAGTCCATC
AAGACAGAATCCTTTTAAAAAATAACCACTCCACTCCAGCAATACCACAGAAGAATCTGGCTGTACCC
CAGGTACATCAGCAAAGATAACCTTTACCTAGCAGTAAAGAGGTCCCCCTTACACTGGGAGCCCTAGT
GAAGAGCAGGGACTTTCACCCCCACTTAGCAGTGATGGGCCCCACCCACCACAGTGCCAGCAGAGAC
CATGTGGGAGCCAGAATCCTCATCCCTACCCAGCAGTAACAAGGAGCCCTCCTCACTGCGGGCATCAA
GGGTGAGTGAGTGCAAAACCTGGGTGTCACTCGGAAGGGAAGAATGGTGTCTCCTTCCTTCCCATCCC
CTGCCAGAGTGATATCACTAGGAAAAAG
>*EPIC1 v3 (SEQ ID NO: 3)*
AGTCCGCCATTGCAAACACGAAGCTCTTCCAGAAACGCCCTCACAGACACCCCGGAAGTCACGTACCC
ACTCTGTAGGTGCCCCGGGGCACAGGCAAGCGGACGAGCCAGTTATCCCTCAGAGCTCCTGCTGCCTC
GCCCGCTTTCTCTCGGAAACGTGAAGTGTGGCCTCAGCTGAAAGTGAGGTGGGCCTCATTCAATCAGT
TGAATTCTTCAAGAGAGAAAAACTGAAGTCCCTTAGAAGGAAAGAGTTCTGCCTTCAGACTGTCTTTG
AACTTAAGACTGTAGCGTCGACTCCTGCCGGAATTTCCAGCCTGCTGGCCAGCTCTGCAGATTCACAC
TTGCCAGCCTCCACAATCGCAGCTGAGGCGGAGGAACCCTAAGGGCTCATTGAGATCATGGATTTGCC
CTTCTATGCATTGATGGAGCACCTGCTGCCCACAGCGTCTGTATTTGGTGCTGGGATGCTGAGCCTCC
TTCTTTATGAATTTTTAAAAGGACACTGAGATCTTCAAACAGAGGCTGCCACTCTAAGCAAACAGATC
CCGAGTCCTGGACTCTGAAGCTTGGGCCCAGTTCTCCTTTTCTCCGGGTTTCAGATCCCACTGTAAAG
TGAGGGGGCCCTTCTGATTCAGGACCCGGGGAAGCCAGGGGCATGAGCATCGGTGCCTCTTCTCTATT
TCAAGGACCCTTCTGGGTGTAAAGTTCTCTGAGATGCCTTACATGGATTCCCACCACTGCAAGATAAC
CATCGTATGTAAAGTGTTATGACCAGCAGAGTGTAATTGAAGTGCATTCCAGAGGGAAAGACAGCGGC
TCAGATTCTATTGAAAGAAACATGACATAATGATACCACAGCAAAAGCCAATCTTGCTCCTTTTTA

*FIG. 1*

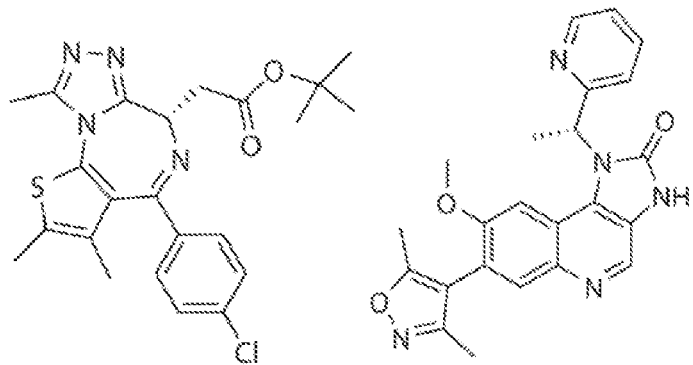
(+)-JQ1  I-BET151 (GSK1210151A)
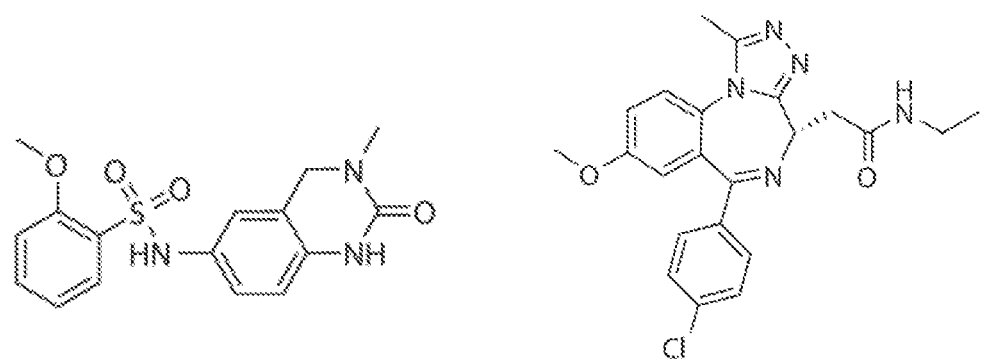
PFI-1 (PF-6405761)  I-BET-762
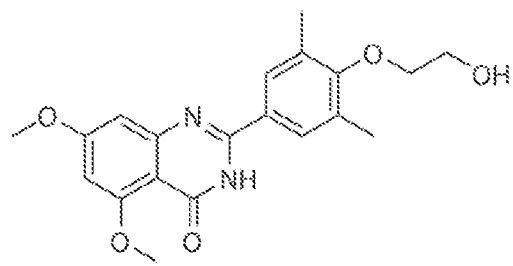
Apabetalone (RVX-208)
*FIG. 2*

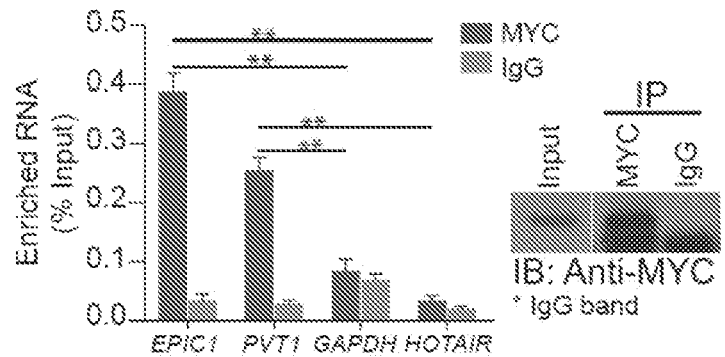
FIG. 9B
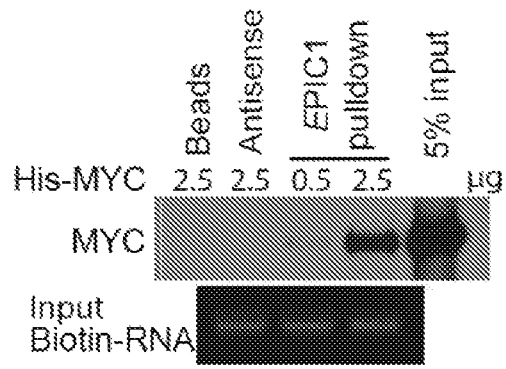
FIG. 9C
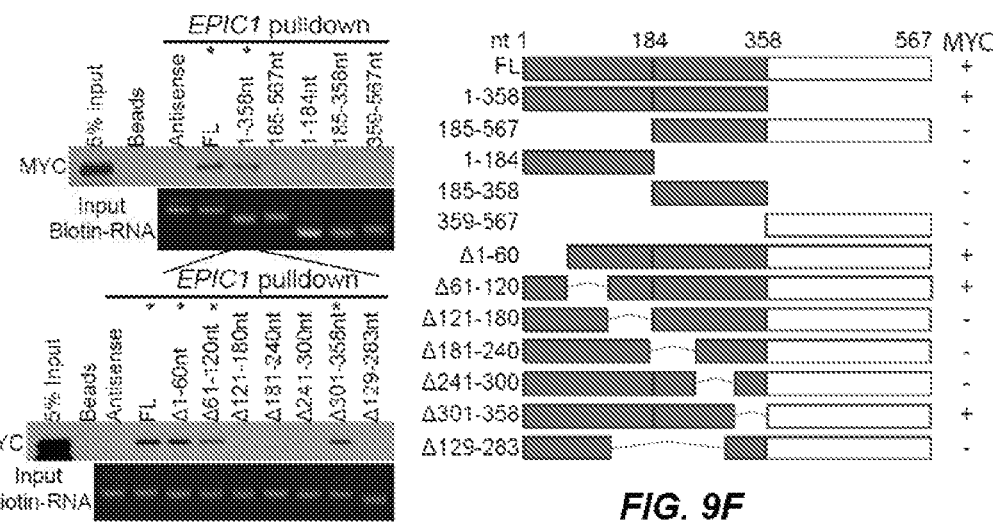
FIG. 9D
FIG. 9E
FIG. 9F

SEQUENCE LISTING

<160> NUMBER OF SEQ ID NOS: 21

<210> SEQ ID NO 1
<211> LENGTH: 567
<212> TYPE: DNA
<213> ORGANISM: Homo sapiens

```
<400> SEQUENCE: 1
agtccgccat tgcaaacacg aagctcttcc agaaacgccc tcacagacac cccggaagtc    60
acgtacccac tctgtaggtg ccccggggca caggcaagcg gacgagccag ttatccctca   120
gagctcctgc tgcctcgccc gctttctctc ggaaacgtga agtgtggcct cagctgaaag   180
tgaggtgggc ctcattcaat cagttgaatt cttcaagaga gaaaaactga agtcccttag   240
aaggaaagag ttctgccttc agactgtctt tgaacttaag actgtagcgt cgactcctgc   300
cggaatttcc agcctgctgg ccagctctgc agattcacac ttgccagcct ccacaatcgt   360
gtgagccaat tccttaactt ctctttctcc gtgtatccct ttggtgctgc ctctctgggg   420
agccctgact aatatgcatg cagatgatac ggtgcctggc attctgaata catgcactaa   480
atccaccact tttccccatt tatagatttg gattaacaca ctaacttact catatctgca   540
agtataaata aaaaaaattg ctggtgc                                       567

<210> SEQ ID NO 2
<211> LENGTH: 844
<212> TYPE: DNA
<213> ORGANISM: Homo sapiens

<400> SEQUENCE: 2
agtccgccat tgcaaacacg aagctcttcc agaaacgccc tcacagacac cccggaagtc    60
acgtacccac tctgtaggtg ccccggggca caggcaagcg gacgagccag ttatccctca   120
gagctcctgc tgcctcgccc gctttctctc ggaaacgtga agtgtggcct cagctgaaag   180
tgaggtgggc ctcattcaat cagttgaatt cttcaagaga gaaaaactga agtcccttag   240
aaggaaagag ttctgccttc agactgtctt tgaacttaag actgtagcgt cgactcctgc   300
cggaatttcc agcctgctgg ccagctctgc agattcacac ttgccagcct ccacaatctt   360
cctggatttg aaactgaaga agcaagcaat ctggaaatgt cagtggatgc acacaaagaa   420
acaaccgcaa aagcctgctc gctctagcca agggacaaga ataggggcag tccatcaaga   480
cagaatcctt ttaaaaaata accactccac tccagcaata ccacagaaga atctggctgt   540
accccaggta catcagcaaa gataacctt acctagcagt aaagaggtcc cccttacact   600
gggagcccta gtgaagagca gggactttca ccccacttta gcagtgatgg ggccccaccc   660
accacagtgc cagcagagac catgtgggag ccagaatcct catccctacc agcagtaac   720 aaggagccct cctcactgcg ggcatcaagg gtgagtgagt gcaaacctg ggtgtcactc   780 ggaagggaag aatggtgtct ccttccttcc catcccctgc cagagtgata tcactaggaa   840
aaag                                                               844

<210> SEQ ID NO 3
<211> LENGTH: 882
<212> TYPE: DNA
<213> ORGANISM: Homo sapiens

<400> SEQUENCE: 3
agtccgccat tgcaaacacg aagctcttcc agaaacgccc tcacagacac cccggaagtc    60
acgtacccac tctgtaggtg ccccggggca caggcaagcg gacgagccag ttatccctca   120
gagctcctgc tgcctcgccc gctttctctc ggaaacgtga agtgtggcct cagctgaaag   180
tgaggtgggc ctcattcaat cagttgaatt cttcaagaga gaaaaactga agtcccttag   240
aaggaaagag ttctgccttc agactgtctt tgaacttaag actgtagcgt cgactcctgc   300
cggaatttcc agcctgctgg ccagctctgc agattcacac ttgccagcct ccacaatcgc   360
```

```
agctgaggcg gaggaacccct aagggctcat tgagatcatg gatttgccct tctatgcatt    420
gatggagcac ctgctgccca cagcgtctgt atttggtgct gggatgctga gcctccttct    480
ttatgaattt ttaaaaggac actgagatct tcaaacagag gctgccactc taagcaaaca    540
gatcccgagt cctggactct gaagcttggg cccagttctc cttttctccg ggtttcagat    600
cccactgtaa agtgagggggg cccttctgat tcaggacccg gggaagccag ggcatgagc    660 atcggtgcct cttctctatt tcaaggaccc ttctgggtgt aaagttctct gagatgcctt    720
acatggattc ccaccactgc aagataacca tcgtatgtaa agtgttatga ccagcagagt    780
gtaattgaag tgcattccag agggaaagac agcggctcag attctattga aagaaacatg    840
acataatgat accacagcaa aagccaatct tgctcctttt ta                       882
```

```
<210> SEQ ID NO 4
<211> LENGTH: 19
<212> TYPE: RNA
<213> ORGANISM: Artificial Sequence
<220> FEATURE:
<223> OTHER INFORMATION: RNAi agent

<400> SEQUENCE: 4
ccuucagacu gucuuugaa                                                   19

<210> SEQ ID NO 5
<211> LENGTH: 19
<212> TYPE: RNA
<213> ORGANISM: Artificial Sequence
<220> FEATURE:
<223> OTHER INFORMATION: RNAi agent

<400> SEQUENCE: 5
gcuuucucuc ggaaacgug                                                   19

<210> SEQ ID NO 6
<211> LENGTH: 19
<212> TYPE: RNA
<213> ORGANISM: Artificial Sequence
<220> FEATURE:
<223> OTHER INFORMATION: RNAi agent

<400> SEQUENCE: 6
aguguggccu cagcugaaa                                                   19

<210> SEQ ID NO 7
<211> LENGTH: 21
<212> TYPE: DNA
<213> ORGANISM: Artificial Sequence
<220> FEATURE:
<223> OTHER INFORMATION: shRNA target

<400> SEQUENCE: 7
tgccttcaga ctgtctttga a                                                21

<210> SEQ ID NO 8
<211> LENGTH: 21
<212> TYPE: DNA
<213> ORGANISM: Artificial Sequence
<220> FEATURE:
<223> OTHER INFORMATION: shRNA target

<400> SEQUENCE: 8
gctttctctc ggaaacgtga a                                                21
```

```
<210> SEQ ID NO 9
<211> LENGTH: 16
<212> TYPE: DNA
<213> ORGANISM: Artificial Sequence
<220> FEATURE:
<223> OTHER INFORMATION: antisense target sequence

<400> SEQUENCE: 9
gtcgactcct gccgga                                                    16

<210> SEQ ID NO 10
<211> LENGTH: 21
<212> TYPE: DNA
<213> ORGANISM: Artificial Sequence
<220> FEATURE:
<223> OTHER INFORMATION: siRNA

<400> SEQUENCE: 10
ccuucagacu gucuuugaat t                                              21

<210> SEQ ID NO 11
<211> LENGTH: 21
<212> TYPE: DNA
<213> ORGANISM: Artificial Sequence
<220> FEATURE:
<223> OTHER INFORMATION: siRNA

<400> SEQUENCE: 11
uucaaagaca gucugaaggt t                                              21

<210> SEQ ID NO 12
<211> LENGTH: 21
<212> TYPE: DNA
<213> ORGANISM: Artificial Sequence
<220> FEATURE:
<223> OTHER INFORMATION: siRNA

<400> SEQUENCE: 12
gcuuucucuc ggaaacgugt t                                              21

<210> SEQ ID NO 13
<211> LENGTH: 21
<212> TYPE: DNA
<213> ORGANISM: Artificial Sequence
<220> FEATURE:
<223> OTHER INFORMATION: siRNA

<400> SEQUENCE: 13
cacguuuccg agagaaagct t                                              21

<210> SEQ ID NO 14
<211> LENGTH: 21
<212> TYPE: DNA
<213> ORGANISM: Artificial Sequence
<220> FEATURE:
<223> OTHER INFORMATION: siRNA

<400> SEQUENCE: 14
aguguggccu cagcugaaat t                                              21

<210> SEQ ID NO 15
<211> LENGTH: 21
<212> TYPE: DNA
<213> ORGANISM: Artificial Sequence
<220> FEATURE:
<223> OTHER INFORMATION: siRNA
```

```
<400> SEQUENCE: 15
uuucagcuga ggccacacut t                                              21

<210> SEQ ID NO 16
<211> LENGTH: 21
<212> TYPE: DNA
<213> ORGANISM: Artificial Sequence
<220> FEATURE:
<223> OTHER INFORMATION: siRNA

<400> SEQUENCE: 16
gugcguuguu aguacuaaut t                                              21

<210> SEQ ID NO 17
<211> LENGTH: 21
<212> TYPE: DNA
<213> ORGANISM: Artificial Sequence
<220> FEATURE:
<223> OTHER INFORMATION: siRNA

<400> SEQUENCE: 17
auuaguacua acaacgcact t                                              21

<210> SEQ ID NO 18
<211> LENGTH: 20
<212> TYPE: DNA
<213> ORGANISM: Artificial Sequence
<220> FEATURE:
<223> OTHER INFORMATION: PCR primer

<400> SEQUENCE: 18
tatccctcag agctcctgct                                                20

<210> SEQ ID NO 19
<211> LENGTH: 20
<212> TYPE: DNA
<213> ORGANISM: Artificial Sequence
<220> FEATURE:
<223> OTHER INFORMATION: PCR primer

<400> SEQUENCE: 19
aggctggcaa gtgtgaatct                                                20

<210> SEQ ID NO 20
<211> LENGTH: 20
<212> TYPE: DNA
<213> ORGANISM: Artificial Sequence
<220> FEATURE:
<223> OTHER INFORMATION: PCR primer

<400> SEQUENCE: 20
ggtgaaggtc ggagtcaacg                                                20

<210> SEQ ID NO 21
<211> LENGTH: 22
<212> TYPE: DNA
<213> ORGANISM: Artificial Sequence
<220> FEATURE:
<223> OTHER INFORMATION: PCR primer

<400> SEQUENCE: 21
tgggtggaat catattggaa ca                                             22
```

TARGETING CANCER-ASSOCIATED LONG NON-CODING RNAS

CROSS REFERENCE TO RELATED APPLICATIONS

This application is the United States national phase of International Application No. PCT/US2019/019155 filed Feb. 22, 2019, and claims the benefit of U.S. Provisional Patent Application No. 62/633,828, filed Feb. 22, 2018, each of which is incorporated herein by reference in its entirety.

STATEMENT REGARDING FEDERAL FUNDING

This invention was made with government support under Grant No. CA222274 awarded by the National Institutes of Health. The government has certain rights in the invention.

SEQUENCE LISTING

The Sequence Listing associated with this application is filed in electronic format via EFS-Web and is hereby incorporated by reference into the specification in its entirety. The name of the text file containing the Sequence Listing is 6527_2004400_ST25.txt. The size of the text file is 6,979 bytes, and the text file was created on Aug. 17, 2020.

Provided herein are methods of treating cancers and improving chemotherapies and immunotherapies for cancers.

Recent large-scale studies, such as the Encyclopedia of DNA Elements (ENCODE), suggest that 75% of the human genome is capable of being transcribed into primary RNA transcripts, including numerous non-coding RNA (ncRNA). Long non-coding RNAs (lncRNAs) are ncRNA transcripts larger than 200 nt that do not have protein-coding potential. The most recent genome-wide characterization of the human cancer transcriptome in multiple cancer types has revealed that lncRNAs are among the most prevalent transcriptional changes in cancer. Functional characterizations of lncRNAs have suggested that some lncRNAs play important roles in tumorigenesis. Cancer is a complex disease involving multistep genetic and epigenetic changes. Tremendous efforts have been made to better characterize the cancer to identify novel biomarkers and develop new therapy. Those large-scale high-throughput cancer genomics efforts, mainly focusing on protein coding components of the genome, have led to many insightful discoveries, but also new questions: few new cancer genes were identified in cancer to fully explain the molecular and clinical heterogeneity of this aggressive disease. New therapies are needed for the treatment of cancer.

SUMMARY

In one aspect, a method is provided for reducing the occupancy of Myc protein to the promoters of its target genes in a cell. The method comprises knocking down or silencing EPigenetically Induced lnCRNA1 (EPIC1) levels in the cell with a nucleic acid or nucleic acid analog able to knock down expression of EPIC1.

In another aspect, a method of treating cancer in a patient is provided. The method comprises knocking down or silencing EPigenetically Induced lnCRNA1 (EPIC1) levels in a cancer cell of the patient with a nucleic acid or nucleic acid analog able to knock down expression of EPIC1.

In another aspect, nucleic acid or nucleic acid analog is provided that comprises a sequence that has at least 95% sequence identity, at least 99% sequence identity, or 100% sequence identity with at least 15 contiguous bases of SEQ ID NO: 1, SEQ ID NO: 2, or SEQ ID NO: 3, or a sequence complementary thereto.

BRIEF DESCRIPTION OF THE DRAWINGS

FIG. 1 provides exemplary cDNA sequences for three isoforms of EPIC1 (SEQ ID NOS: 1-3).

FIG. 2 provides structures of exemplary iBET compounds.

(FIG. 5A) Kaplan-Meier survival curve represents the proportion survival of breast cancer patients with three subgroups. (FIG. 5B) Forest plot of EPIC1's association with survival in six independent breast cancer cohorts. EPIC1's expression is measured by Affymetrix 1563009_at (HG-U133_Plus_2). (FIG. 5C) Association between EPIC1 expression and breast cancer survival in six independent breast cancer cohorts.

FIG. 6B. (Quantitative RT-PCR analysis of knockdown efficiency of EPIC1 siRNAs in MCF-7 cells. (FIGS. 6C-6E) Quantitative RT-PCR analysis of EPIC1 expression (FIG. 6C), MTT assay (FIG. 6D), and anchorage-independent colony formation assays and representative images (FIG. 6E) of MCF-7 cells stably expressing shCtrl and shEPIC1 RNA, respectively. Error bars indicate mean±SD, n=3 for technical replicates. *p<0.05, **p<0.01.

FIGS. 9A-H. EPIC1 Binds Directly with MYC. Western blot of MYC proteins retrieved by in-vitro-transcribed biotinylated EPIC1 from MCF-7 cell nuclear extracts. Antisense EPIC1 was used as a negative control. S, sense strand; AS, antisense strand. FIG. 9A. qRT-PCR analysis of EPIC1 and PVT1 enriched by MYC proteins in MCF-7 cells. Western blot of MYC is shown (right). HOTAIR and GAPDH served as negative controls. Error bars indicate mean±SD, n=3 for technical replicates. **p<0.01. FIG. 9B. Western blot of recombinant MYC proteins retrieved by EPIC1 RNA in in vitro binding assay. EPIC1 antisense was used as a negative control. FIG. 9C. Western blot of MYC pulled down by truncated EPIC1. FIG. 9D. Mapping of the MYC binding region within the 1-358 region of EPIC1. FIG. 9E. Schematic of truncated or deletion mutants of EPIC1. The MYC binding capability is shown (right). FIG. 9G. Western blot of truncated MYC proteins retrieved by in-vitro-transcribed EPIC1. FIG. 9H. Schematic of truncated MYC protein. The EPIC1 binding capability is shown. TAD, N-terminal transactivation domain; MB1-3, MYC boxes 1-3; bHLHLZ, basic-helix-loop-helix-leucine zipper domain; CTD, C-terminal domain.

(FIGS. 10B and 10C) Western blot of MYC targets (FIG. 10B) and MTT assay (FIG. 10C) after treatment with MYC siRNAs in MCF-7 cells with stable overexpression of EPIC1 and empty vector. (FIG. 10D Cell-cycle analysis of EPIC1, CDKN1A, and CCNA2 level in MCF-7 cells transfected with LNA against EPIC1 followed by overexpression of indicated vectors. Error bars indicate mean±SD, n=3 for technical replicates. *p<0.05, **p<0.01. NS, not significant.

FIG. 11A: Endogenous expression level of EPIC1 in 13 cell lines and water. FIG. 11B: Growth inhibition curves for EPIC1 knockdown or control MCF-7 cells treated with BET inhibitor I-BET-762 (left) and JQ-1 (right). FIG. 11C: Growth inhibition curves for EPIC1 overexpression or control MCF-7 cells treated with BET inhibitor I-BET-762 (left) and JQ-1 (right). Data are presented as mean±SD (n=3 for technical replicates)

DETAILED DESCRIPTION

Figure 3:
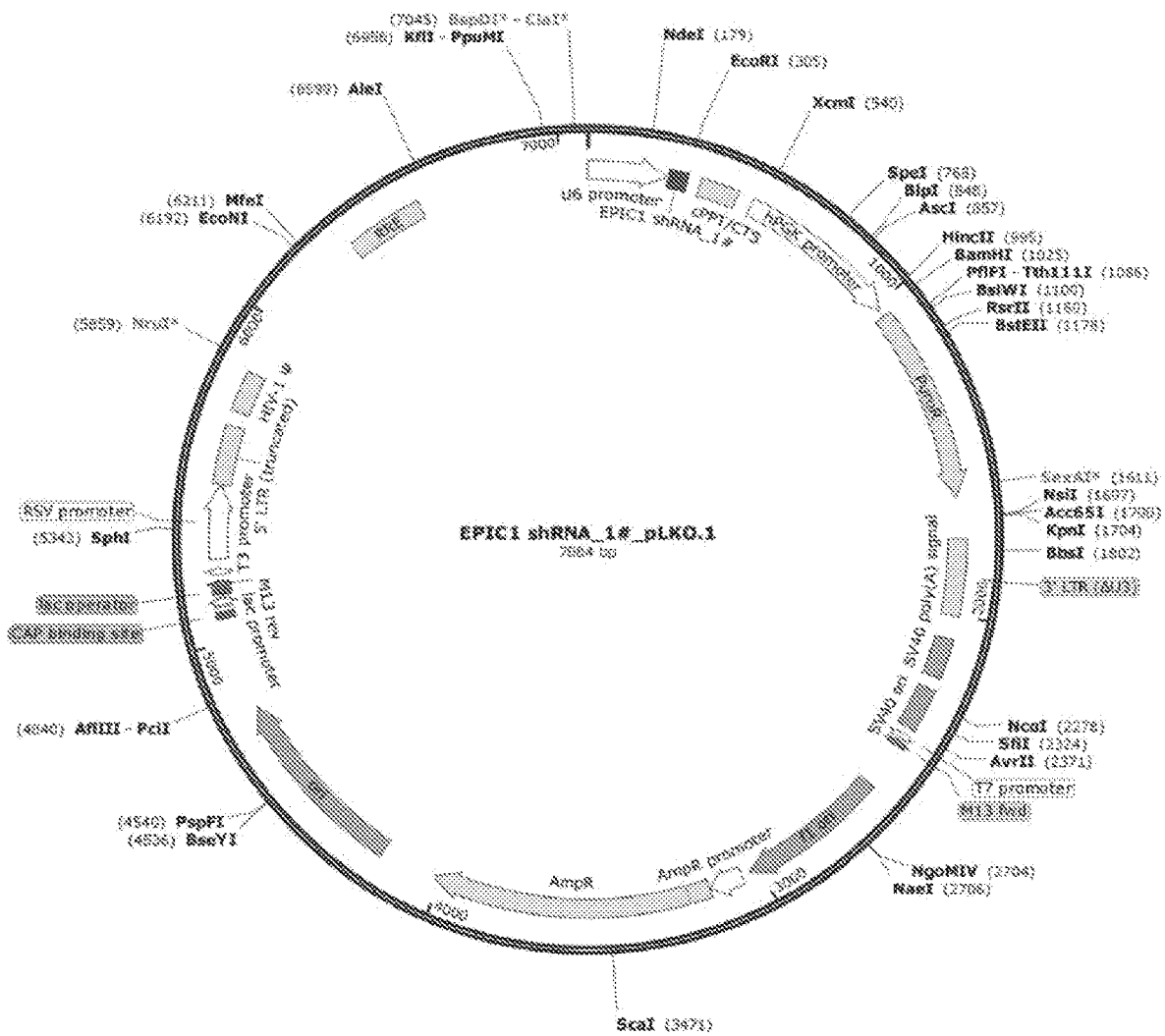
FIG. 3 is a plasmid map of an exemplary shRNA expression construct.

The following description is merely exemplary in nature and is in no way intended to limit the invention, its application, or uses. While the description is designed to permit one of ordinary skill in the art to make and use the invention, and specific examples are provided to that end, they should in no way be considered limiting. It will be apparent to one of ordinary skill in the art that various modifications to the following will fall within the scope of the appended claims. The present invention should not be considered limited to the presently disclosed aspects, whether provided in the examples or elsewhere herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. As used herein "a" and "an" refer to one or more.

As used herein, the terms "comprising," "comprise" or "comprised," and variations thereof, are open ended and do not exclude the presence of other elements not identified. In contrast, the term "consisting of" and variations thereof is intended to be closed and excludes additional elements in anything but trace amounts.

As used herein, the term "patient" or "subject" refers to members of the animal kingdom including but not limited to human beings and "mammal" refers to all mammals, including, but not limited to human beings.

As used herein, the "treatment" or "treating" of obesity, hyperglycemia, diabetes, metabolic syndrome, insulin resistance (insulin insensitivity), impaired glucose tolerance, high glucose levels, pulmonary hypertension, and/or a condition arising from any of the foregoing, in a patient, means administration to a patient by any suitable dosage regimen, procedure and/or administration route of a composition, device, or structure with the object of achieving a beneficial or desirable clinical/medical end-point, including but not limited to, preventing, reducing, and/or eliminating any symptom of obesity, hyperglycemia, diabetes, metabolic syndrome, insulin resistance (insulin insensitivity), impaired glucose tolerance, high glucose levels, pulmonary hypertension, and/or a condition arising from any of the foregoing, in a patient. An amount of any agent, administered by any suitable route, effective to treat a patient is an amount capable of preventing, reducing, and/or eliminating any symptom of obesity, hyperglycemia, diabetes, metabolic syndrome, insulin resistance (insulin insensitivity), impaired glucose tolerance, high glucose levels, pulmonary hypertension, and/or a condition arising from any of the foregoing, in a patient.

The compositions described herein can be administered by any effective route, such as parenteral, e.g., intravenous, intramuscular, subcutaneous, intradermal, etc., formulations of which are described below and in the below-referenced publications, as well as is broadly-known to those of ordinary skill in the art.

Suitable dosage forms may include single-dose, or multiple-dose vials or other containers, such as medical syringes, containing a composition comprising an active ingredient useful for treatment of obesity, hyperglycemia, diabetes, metabolic syndrome, insulin resistance (insulin insensitivity), impaired glucose tolerance, high glucose levels, pulmonary hypertension, and/or a condition arising from any of the foregoing, as described herein.

EPIC1 is a non-coding gene, comprising at least three isoforms. cDNA sequences from three isoforms of EPIC1 are provided in FIG. 1 (SEQ ID NOS: 1-3). By EPIC1, it is meant not only human EPIC1, but EPIC1 from any vertebrate or mammalian source, including, but not limited to, human, bovine, chicken, rodent, mouse, rat, porcine, ovine, primate, monkey, and guinea pig, unless specified otherwise. The term also refers to fragments, variants, alleles, and isoforms of native EPIC1 that maintain at least one in vivo or in vitro activity of EPIC1 as exemplified by SEQ ID NOS: 1-3. The term encompasses full-length unprocessed precursor forms of EPIC1, as well as mature forms resulting from further processing, e.g., from post-translational processing.

In one aspect, where an RNAi agent is used to knock down expression of EPIC1, the target portion of the sequence will be at least long enough to serve as a substrate for iRNA-directed cleavage at or near that portion of the nucleotide sequence of an mRNA molecule formed during the transcription of an EPIC1 gene.

"Expression" of a gene refers to the conversion of a DNA sequence of a gene, e.g., the EPIC1 gene, to an active, mature gene product such as a polypeptide/protein, or a functional nucleic acid, and includes, for example, transcription, post-transcriptional modification (e.g., splicing), translation, and post-translational processing and/or modification of a protein. In the case of EPIC1, the mature gene product is an RNA. Expression of a gene can be reduced by any effective mechanism at any stage of the gene expression process, such as by affecting transcriptional activation, transcription, post-transcriptional RNA processing, translation, and post-translational processing or modification. Expression of an RNA, such as the EPIC1 RNA (EPIC1 ncRNA) described herein refers to, without limitation, any aspect of transcription of, splicing of, translation of, and post-translational processing, stability, and activity of a protein product of the mRNA, e.g., any aspect of transcription, splicing, and post-transcriptional stability of the RNA product of the EPIC1 gene. Decreasing the activity of a gene product may be accomplished not only by decreasing expression of the active RNA or protein product, but by affecting the mature RNA or protein product, such as by blocking, decoying, or otherwise interfering with the binding of the active product, or a complex containing the active product, to prevent its activity.

A "vector" refers to a nucleic acid construct including sequences for delivering and replicating a sequence or foreign genetic material in a cell. The foreign genetic material can be a gene for expressing a ncRNA or protein, e.g., SEQ ID NOs: 1-3, or shRNAs as described herein. Non-limiting examples of vectors include plasmids, viral genomes such as phage genomes and particles, recombinant viral genomes and particles, artificial chromosomes, and genomic inserts. When the vector is transformed in the appropriate host, the vector may replicate and function independent of the host genome, or in some cases, may be incorporated with the genome itself. A large variety of vectors, such as retroviral, AAV, plasmid, and CRISPR vectors are available from a variety of sources, both commercial and non-commercial, and are broadly-known to those of ordinary skill in the art.

Drug products, or pharmaceutical compositions comprising an active agent (e.g., drug), for example, an active agent that decreases EPIC1 expression, stability, or activity may be prepared by any method known in the pharmaceutical arts, for example, by bringing into association the active ingredient with the carrier(s) or excipient(s). As used herein, a "pharmaceutically acceptable excipient", "carrier" or "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable excipients include one or more of water, saline, phosphate buffered saline, dextrose, glycerol, ethanol and the like, as well as combinations thereof. In many cases, it may be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the active agent. In certain aspects, the active compound may be prepared with a carrier that will protect the compound against rapid release, such as a controlled release formulation, including implants, transdermal patches, and microencapsulated delivery systems. Biodegradable, biocompatible polymers can be used in delivery systems, such as ethylene vinyl acetate, polyanhydrides, polyglycolic acid, collagen, polyorthoesters, and polylactic acid. Many methods for the preparation of such formulations are broadly-known to those skilled in the art.

Additionally, active agent-containing compositions may be in variety of forms. The preferred form depends on the intended mode of administration and therapeutic application, which will in turn dictate the types of carriers/excipients. Suitable forms include, but are not limited to, liquid, semi-solid and solid dosage forms.

Pharmaceutical formulations adapted for oral administration may be presented, for example and without limitation, as discrete units such as capsules or tablets; powders or granules; solutions or suspensions in aqueous or non-aqueous liquids; edible foams or whips; or oil-in-water liquid emulsions or water-in-oil liquid emulsions. In certain embodiments, the active agent may be contained in a formulation such that it is suitable for oral administration, for example, by combining the active agent with an inert diluent or an assimilable edible carrier. The active agent (and other ingredients, if desired) may also be enclosed in a hard- or soft-shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Pharmaceutical formulations adapted for transdermal administration may be presented, for example and without limitation, as discrete patches intended to remain in intimate contact with the epidermis of the recipient for a prolonged period of time or electrodes for iontophoretic delivery.

Pharmaceutical formulations adapted for topical administration may be formulated, for example and without limitation, as ointments, creams, suspensions, lotions, powders, solutions, pastes, gels, sprays, aerosols or oils.

Pharmaceutical formulations adapted for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include, without limitation, fine particle dusts or mists which may be generated by means of various types of metered dose pressurized aerosols, nebulizers or insufflators. In the context of delivery of the active agents described herein by inhalation, inhalation drug products, such as metered-dose inhalers, as are broadly-known in the pharmaceutical arts, are used. Metered dose inhalers are configured to deliver a single dose of an active agent per actuation, though multiple actuations may be needed to effectively treat a given patient.

Pharmaceutical formulations adapted for parenteral administration include aqueous and non-aqueous sterile injection solutions which may contain, for example and without limitation, anti-oxidants, buffers, bacteriostats, lipids, liposomes, emulsifiers, also suspending agents and rheology modifiers. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets.

Therapeutic compositions typically must be sterile and stable under the conditions of manufacture and storage. For example, sterile injectable solutions can be prepared by incorporating the active agent in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, typical methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

A "therapeutically effective amount" refers to an amount of a drug product or active agent effective, at dosages and for periods of time necessary, to achieve the desired therapeutic result. An "amount effective" for treatment of a condition is an amount of an active agent or dosage form, such as a single dose or multiple doses, effective to achieve a determinable end-point. The "amount effective" is preferably safe—at least to the extent the benefits of treatment outweighs the detriments, and/or the detriments are acceptable to one of ordinary skill and/or to an appropriate regulatory agency, such as the U.S. Food and Drug Administration. A therapeutically effective amount of an active agent may vary according to factors such as the disease state, age, sex, and weight of the individual, and the ability of the active agent to elicit a desired response in the individual. A "prophylactically effective amount" refers to an amount effective, at dosages and for periods of time necessary, to achieve a desired prophylactic result. Typically, since a prophylactic dose is used in subjects prior to or at an earlier stage of disease, the prophylactically effective amount may be less than the therapeutically effective amount.

Dosage regimens may be adjusted to provide the optimum desired response (e.g., a therapeutic or prophylactic response). For example, a single bolus may be administered, several divided doses may be administered over time, or the composition may be administered continuously or in a pulsed fashion with doses or partial doses being administered at regular intervals, for example, every 10, 15, 20, 30, 45, 60, 90, or 120 minutes, every 2 through 12 hours daily, or every other day, etc., be proportionally reduced or increased as indicated by the exigencies of the therapeutic situation. In some instances, it may be especially advantageous to formulate compositions, such as parenteral or inhaled compositions, in dosage unit form for ease of administration and uniformity of dosage. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

By "target-specific" or reference to the ability of one compound to bind another target compound specifically, it is meant that the compound binds to the target compound to the exclusion of others in a given reaction system, e.g., in vitro, or in vivo, to acceptable tolerances, permitting a sufficiently specific diagnostic or therapeutic effect according to the standards of a person of skill in the art, a medical community, and/or a regulatory authority, such as the U.S. Food and Drug Agency (FDA), in aspects, in the context of targeting EPIC1, and down-regulating EPIC1 activity, and effectively treating a cancer, or as an adjunct to a chemotherapy, as described herein.

A "gene" is a sequence of DNA or RNA which codes for a molecule, such as a protein or a functional RNA, such as a ncRNA that has a function. Nucleic acids are biopolymers, or small biomolecules, essential to all known forms of life. They are composed of nucleotides, which are monomers made of three components: a 5-carbon sugar, a phosphate group and a nitrogenous base. If the sugar is a simple ribose, the polymer is RNA; if the sugar is derived from deoxyribose, the polymer is DNA. DNA typically uses the nitrogenous bases guanine, thymine, adenine, and cytosine. RNA typically uses the nitrogenous bases guanine, uracil, adenine, and cytosine.

Complementary refers to the ability of polynucleotides (nucleic acids) to hybridize to one another, forming interstrand base pairs. Base pairs are formed by hydrogen bonding between nucleotide units in antiparallel polynucleotide strands. Complementary polynucleotide strands can base pair (hybridize) in the Watson-Crick manner (e.g., A to T, A to U, C to G), or in any other manner that allows for the formation of duplexes. When using RNA as opposed to DNA, uracil rather than thymine is the base that is complementary to adenosine. Two sequences comprising complementary sequences can hybridize if they form duplexes under specified conditions, such as in water, saline (e.g., normal saline, or 0.9% w/v saline) or phosphate-buffered saline), or under other stringency conditions, such as, for example and without limitation, 0.1×SSC (saline sodium citrate) to 10×SSC, where 1×SSC is 0.15M NaCl and 0.015M sodium citrate in water. Hybridization of complementary sequences is dictated, e.g., by salt concentration and temperature, with the melting temperature (Tm) lowering with increased mismatches and increased stringency. Perfectly matched sequences are said to be fully complementary, or have 100% sequence identity (gaps are not counted and the measurement is in relation to the shorter of the two sequences). In one aspect, a sequence that "specifically hybridizes" to another sequence, does so in a hybridization solution containing 0.5M sodium phosphate buffer, pH 7.2, containing 7% SDS, 1 mM EDTA, and 100 mg/ml of salmon sperm DNA at 65° C. for 16 hours and washing twice at 65° C. for twenty minutes in a washing solution containing 0.5×SSC and 0.1% SDS, or does so under conditions more stringent than 2×SSC at 65° C., for example, in 0.2×SSC at 55° C. A sequence that specifically hybridizes to another typically has at least 80%, 85%, 90%, 95%, or 99% sequence identity with the other sequence.

Gene expression is the process by which information from a gene is used in the synthesis of a functional gene product, e.g., a protein or functional RNA. Gene expression involves various steps, including transcription, translation, and post-translational modification of a protein.

Transcription is the process by which the DNA gene sequence is transcribed into pre-mRNA (messenger RNA). The steps include: RNA polymerase, together with one or more general transcription factors, binds to promoter DNA. Transcription factors (TFs) are proteins that control the rate of transcription of genetic information from DNA to messenger RNA, by binding to a specific DNA sequence (i.e., the promoter region). The function of TFs is to regulate genes in order to make sure that they are expressed in the right cell at the right time and in the right amount throughout the life of the cell and the organism. The promoter region of a gene is a region of DNA that initiates transcription of that particular gene. Promoters are located near the transcription start sites of genes, on the same strand, and often, but not exclusively, are upstream (towards the 5' region of the sense strand) on the DNA. Promoters can be about 100-1000 base pairs long. Additional sequences and non-coding elements can affect transcription rates. If the cell has a nucleus (eukaryotes), the RNA is further processed. This includes polyadenylation, capping, and splicing. Polyadenylation is the addition of a poly(A) tail to a messenger RNA. The poly(A) tail consists of multiple adenosine monophosphates; in other words, it is a stretch of RNA that has only adenine bases. In eukaryotes, polyadenylation is part of the process that produces mature messenger RNA (mRNA) for translation. Capping refers to the process wherein the 5' end of the pre-mRNA has a specially altered nucleotide. In eukaryotes, the 5' cap (cap-0), found on the 5' end of an mRNA molecule, consists of a guanine nucleotide connected to mRNA via an unusual 5' to 5' triphosphate linkage. During RNA splicing, pre-mRNA is edited. Specifically, during this process introns are removed and exons are joined together. The resultant product is known as mature mRNA. The RNA may remain in the nucleus or exit to the cytoplasm through the nuclear pore complex.

RNA levels in a cell, e.g., mRNA levels, can be controlled post-transcriptionally. Native mechanisms, including: endogenous gene silencing mechanisms, interference with translational mechanisms, interference with RNA splicing mechanisms, and destruction of duplexed RNA by RNAse H, or RNAse H-like activity. As is broadly-recognized by those of ordinary skill in the art, these endogenous mechanisms can be exploited to decrease or silence mRNA activity in a cell or organism in a sequence-specific, targeted manner. Antisense technology typically involves administration of a single-stranded antisense oligonucleotide (ASO) that is chemically-modified, e.g., as described herein, for bio-stability, and is administered in sufficient amounts to effectively penetrate the cell and bind in sufficient quantities to target mRNAs in cells. RNA interference (RNAi) harnesses an endogenous and catalytic gene silencing mechanism, which means that once, e.g., a microRNA, or double-stranded siRNA has been delivered into the cytosol, they are efficiently recognized and stably incorporated into the RNA-induced silencing complex (RiSC) to achieve prolonged gene silencing. Both antisense technologies and RNAi have their strengths and weaknesses, either may be used effectively to knock-down or silence expression of a gene or gene product, such as EPIC1 (see, e.g., Watts, J. K., et al. Gene silencing by siRNAs and antisense oligonucleotides in the laboratory and the clinic (2012) 226(2):365-379).

The terms "iRNA," "RNAi agent," "RNAi agent," and "RNA interference agent" as used interchangeably herein, refer to an agent that contains RNA nucleotides, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., knocks down or silences, the expression of EPIC1 RNA in a cell, e.g., a cell within a subject, such as a mammalian subject.

In one aspect, an RNAi agent includes a single stranded RNAi that interacts with a target RNA sequence, e.g., an EPIC1 RNA sequence, to direct the cleavage of the target RNA. Without wishing to be bound by theory it is believed that long double stranded RNA introduced into cells is broken down into double stranded short interfering RNAs (siRNAs) comprising a sense strand and an antisense strand by a Type III endonuclease known as Dicer. Dicer, a ribonuclease-III-like enzyme, processes these dsRNA into 19-23 base pair short interfering RNAs with characteristic two base 3' overhangs. These siRNAs are then incorporated into an RNA-induced silencing complex (RISC) where one or more helicases unwind the siRNA duplex, enabling the complementary antisense strand to guide target recognition. Upon binding to the appropriate target mRNA, one or more endonucleases within the RISC cleave the target to induce silencing. Thus, in one aspect the invention relates to a single stranded RNA (ssRNA) (the antisense strand of an siRNA duplex) generated within a cell and which promotes the formation of a RISC complex to effect silencing of the target gene. Accordingly, the term "siRNA" is also used herein to refer to an interfering RNA (iRNA).

In another aspect, the RNAi agent may be a single-stranded RNA that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded RNAs are described in U.S. Pat. No. 8,101,348 and in Lima et al., (2012) Cell 150:883-894. Any of the RNAi agents described herein may be used as a single-stranded siRNA as described herein or as chemically modified by the methods described in Lima et al.

In another aspect, an "iRNA" or RNAi agent" for use in the compositions and methods described herein is a double stranded RNA and can be referred to herein as a "double stranded RNAi agent," "double stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, e.g., an EPIC1 RNA. In some aspects, a double stranded RNA (dsRNA) triggers the degradation of a target RNA, e.g., an mRNA, through a post-transcriptional gene-silencing mechanism referred to herein as RNA interference or RNAi.

The majority of nucleotides of each strand of a dsRNA molecule may be ribonucleotides, but as described in detail herein, each or both strands can also include nucleotide analogs, where one or more non-ribonucleotides, e.g., a deoxyribonucleotide and/or a modified nucleotide. In addition, as used in this specification, an "RNAi agent" or "RNAi agent" may include ribonucleotides with chemical modifications; an RNAi agent may include substantial modifications at multiple nucleotides. As used herein, the term "modified nucleotide" refers to a nucleotide having, independently, a modified sugar moiety, a modified inter-nucleotide linkage, and/or modified nucleobase. Thus, the term modified nucleotide encompasses substitutions, additions or removal of, e.g., a functional group or atom, to internucleoside linkages, sugar moieties, or nucleobases. The modifications suitable for use in the agents described herein include all types of modifications disclosed herein or known in the art. Any such modifications, as used in a siRNA type molecule, are encompassed by "RNAi agent" or "RNAi reagent" for the purposes of this disclosure.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34,35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some aspects, the hairpin loop can comprise at least 2, at least 3, at least 4, at least 5, at least 6, at least 7, at least 8, at least 9, at least 10, at least 20, at least 23, or more unpaired nucleotides. In some aspects, the hairpin loop can be 10 or fewer nucleotides. In some aspects, the hairpin loop can be 8 or fewer unpaired nucleotides. In some aspects, the hairpin loop can be 4-10 unpaired nucleotides. In some aspects, the hairpin loop can be 4-8 nucleotides.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

In one aspect, an RNAi agent is a dsRNA, each strand of which comprises 19-23 nucleotides, that interacts with a target RNA sequence, e.g., an EPIC1 RNA, without wishing to be bound by theory, long double stranded RNA introduced into cells is broken down into siRNA by a Type III endonuclease known as Dicer. Dicer, a ribonuclease-III-like enzyme, processes the dsRNA into 19-23 base pair short interfering RNAs with characteristic two base 3' overhangs. The siRNAs are then incorporated into an RNA-induced silencing complex (RISC) where one or more helicases unwind the siRNA duplex, enabling the complementary antisense strand to guide target recognition. Upon binding to the appropriate target RNA, one or more endonucleases within the RISC cleave the target to induce silencing. In one aspect, an RNAi agent is a dsRNA of 24-30 nucleotides that interacts with a target RNA sequence, e.g., an EPIC1 RNA sequence, to direct the cleavage of the target RNA.

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively, the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

In one aspect of the dsRNA, at least one strand comprises a 3 ' overhang of at least 1 nucleotide. In another aspect, at least one strand comprises a 3' overhang of at least 2 nucleotides, e.g., 2, 3, 4, 5, 6, 7, 9, 10, 11, 12, 13, 14, or 15 nucleotides. In other aspects, at least one strand of the RNAi agent comprises a 5' overhang of at least 1 nucleotide. In certain aspects, at least one strand comprises a 5' overhang of at least 2 nucleotides, e.g., 2, 3, 4, 5, 6, 7, 9, 10, 11, 12, 13, 14, or 15 nucleotides. In still other aspects, both the 3' and the 5' end of one strand of the RNAi agent comprise an overhang of at least 1 nucleotide.

In one aspect, the antisense strand of a dsRNA has a 1-10 nucleotide, e.g., a 1, 2, 3, 4, 5, 6, 7, 8, 9, or 10 nucleotides, overhang at the 3'-end and/or the 5'-end. In one aspect, the sense strand of a dsRNA has a 1-10 nucleotide, e.g., a 1, 2, 3, 4, 5, 6, 7, 8, 9, or 10 nucleotides, overhang at the 3'-end and/or the 5'-end. In certain aspects, the overhang on the sense strand or the antisense strand, or both, can include extended lengths longer than 10 nucleotides, e.g., 1-30 nucleotides, 2-30 nucleotides, 10-30 nucleotides, or 10-15 nucleotides in length. In certain aspects, an extended overhang is on the sense strand of the duplex. In certain aspects, an extended overhang is present on the 3'end of the sense strand of the duplex. In certain aspects, an extended overhang is present on the 5'end of the sense strand of the duplex. In certain aspects, an extended overhang is on the antisense strand of the duplex. In certain aspects, an extended overhang is present on the 3'end of the antisense strand of the duplex. In certain aspects, an extended overhang is present on the 5'end of the antisense strand of the duplex. In another aspect, one or more of the nucleotides in the overhang is replaced with a nucleoside thiophosphate.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt.

Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double stranded over its entire length.

The term "antisense strand" or "guide strand" refers to the strand of an iRNA, e.g., a dsRNA, which includes a region that is substantially complementary to a target sequence, e.g., an EPIC1 RNA. As used herein, the term "region of complementarity" refers to the region on the antisense strand that is substantially complementary to a sequence, for example, a target sequence, e.g., an EPIC1 RNA sequence sequence, e.g., as described herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the iRNA.

The term "sense strand" or "passenger strand" as used herein, refers to the strand of an iRNA that includes a region that is substantially complementary to a region of the antisense strand as that term is defined herein.

As used herein, the term "cleavage region" refers to a region that is located immediately adjacent to the cleavage site. The cleavage site is the site on the target at which cleavage occurs. In some aspects, the cleavage region comprises three bases on either end of, and immediately adjacent to, the cleavage site. In some aspects, the cleavage region comprises two bases on either end of, and immediately adjacent to, the cleavage site. In some aspects, the cleavage site specifically occurs at the site bound by nucleotides 10 and 11 of the antisense strand, and the cleavage region comprises nucleotides 11, 12 and 13.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3, or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary," and "substantially complementary" herein can be used with respect to the base matching between the sense strand and the antisense strand of a dsRNA, or between the antisense strand of an RNAi agent and a target sequence, as will be understood from the context of their use.

As used herein, a polynucleotide that is "substantially complementary to at least part of a messenger RNA (mRNA)" refers to a polynucleotide that is substantially complementary to a contiguous portion of the mRNA of interest (e.g., an EPIC1 RNA).

Accordingly, in some aspects, the antisense strand polynucleotides disclosed herein are fully complementary to the target EPIC1 RNA sequence. In other aspects, the antisense strand polynucleotides disclosed herein are substantially complementary to the target EPIC1 RNA sequence and comprise a contiguous nucleotide sequence which has at least about 80% sequence identity to the nucleotide sequence of any of SEQ ID NOS: 1-3 (FIG. 1), or a fragment thereof, such as about 85%, about 86%, about 87%, about 88%, about 89%, about 90%, about 91%, about 92%, about 93%, about 94%, about 95%, about 96%, about 97%, about 98%, or about 99% complementary.

It is understood that the sequence of the EPIC1 RNA must be sufficiently complementary to the antisense strand of the RNAi agent for the agent to be used in the indicated patient, e.g. human, mammalian, or vertebrate species.

The term "inhibiting," as used herein, is used interchangeably with "reducing," "silencing," "downregulating," "suppressing," "knocking down," and other similar terms, and includes any level of inhibition.

The phrase "knocking down or silencing of EPIC1 RNA," as used herein, includes inhibition of expression of any EPIC1 gene (such as, e.g., a mouse EPIC1 gene, a rat EPIC1 gene, a monkey EPIC1 gene, or a human EPIC1 gene) as well as variants or mutants of an EPIC1 gene, in its production of EPIC1 RNA, affecting the stability of EPIC1 RNA, such as by antisense or RNAi technologies. "Knocking down or silencing of EPIC1 RNA " includes any level of inhibition of an EPIC1 RNA, e.g., at least partial suppression of the expression of an EPIC1 RNA, such as an inhibition by at least about 20%. In certain aspects, inhibition is by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

The expression of an EPIC1 RNA may be assessed based on the level of any variable associated with EPIC1 RNA expression, e.g., EPIC1 RNA level. The expression of an EPIC1 RNA may also be assessed indirectly based on assay of physiological markers associated with decreased expression of the EPIC1 RNA in a patient or a tumor cell.

In one aspect, at least partial suppression of the expression of an EPIC1 RNA, is assessed by a reduction of the amount of EPIC1 RNA that can be isolated from or detected in a cell or group of cells, e.g., in a tumor cell. As such, in aspects, EPIC1 levels are determined from a tumor biopsy, or from a normal tissue sample obtained from a patient. A reduction of the amount of EPIC1 RNA in a cell or tissue in which an EPIC1 gene is transcribed and which has been treated such that the expression of an EPIC1 RNA is inhibited, may be determined as compared to a second cell or tissue substantially identical to the first cell or tissue but which has not been so treated (control cells), e.g., obtained and cultured from a tumor biopsy. The degree of inhibition may be expressed in terms of:

$$\left( \frac{(mRNA \text{ in control cells}) - (mRNA \text{ in treated cells})}{(mRNA \text{ in control cells})} \times 100\% \right)$$

The phrase "contacting a cell with an RNAi agent," such as a dsRNA, as used herein, includes contacting a cell by any possible means. Contacting a cell with an RNAi agent includes contacting a cell in vitro with the iRNA or contacting a cell in vivo with the iRNA. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell. Further, an shRNA RNAi agent can be produced from a gene for expressing an shRNA, transferred by any suitable means, such as by recombinant vector such as a recombinant Adeno-associated virus (AAV) or retrovirus vector, or by gene editing, such as by CRISPR-Cas or TALENS methods, as are broadly-known. These technologies are broadly-known by those of ordinary skill and resources, such as suitable vectors and production systems are broadly-available, including from commercial sources.

Contacting a cell in vitro may be done, for example, by incubating the cell with the RNAi agent. Contacting a cell in vivo may be done, for example, by injecting the RNAi agent into or near the tissue where the cell is located, such as a tumor, or by injecting the RNAi agent into another area, e.g., the bloodstream or the subcutaneous space, such that the agent will subsequently reach the tissue where the cell to be contacted is located. For example, the RNAi agent may contain and/or be coupled to a ligand, e.g., GalNAc3, which directs the RNAi agent to a site of interest, e.g., the liver. Combinations of in vitro and in vivo methods of contacting are also possible. For example, a cell may also be contacted in vitro with an RNAi agent and subsequently transplanted into a subject.

In one aspect, contacting a cell with an iRNA includes "introducing" or "delivering the iRNA into the cell" by facilitating or effecting uptake or absorption into the cell. Absorption or uptake of an iRNA can occur through unaided diffusive or active cellular processes, or by use of auxiliary agents or devices. Introducing an iRNA into a cell may be in vitro and/or in vivo. For example, for in vivo introduction, iRNA can be injected into a tissue site or administered systemically. In vivo delivery can also be done by a beta-glucan delivery system, such as those described in U.S. Pat. Nos. 5,032,401 and 5,607,677, and U.S. Patent Application Publication No. 2005/0281781. In vitro introduction into a cell includes methods known in the art such as electroporation and lipofection. Further approaches are described herein below and/or are known in the art.

As used herein, and further to the discussion above regarding iRNA reagents, "agent" or "RNAi agent," when used in the context of an antisense, RNAi, or ribozyme, or other single-stranded or double-stranded RNA interfering nucleic acids, refers not only to RNA structures, but effective nucleic acid analog structures. In antisense and RNAi technologies, use of RNA poses significant delivery issues due to the lability of RNA molecules. As such, RNA is commonly chemically-modified to produce nucleic acid analogs, not only to enhance stability of the nucleic acid molecules, but often resulting in increased binding affinity, and with reduced toxicity. Such modifications are broadly-known to those of ordinary skill in the art, and are available commercially (see, e.g., Corey, D. R., Chemical modification: the key to clinical application of RNA interference? (2007) J Clin Invest.117(12):3615-3622, also describing RNAi, and U.S. Patent Application Publication No. 2017/0081667, incorporated herein by reference for its technical disclosure). Non-limiting examples of modifications to the nucleic acid structure in nucleic acid analogs include: modifications to the phosphate linkage, such as phosphoramidates or phosphorothioates; sugar modification, such as 2'-O, 4'-C methylene bridged, locked nucleic acid (LNA), 2'-methoxy, 2'-O-methoxyethyl (MOE), 2'-fluoro, S-constrained-ethyl (cEt), and tricyclo-DNA (tc-DNA); and non-ribose structures, such as phosphorodiamidate morpholino (PMO) and peptide-nucleic acids (PNA).

In addition to those EPIC1-active RNAi agents described herein, antisense agents (ASOs), other RNAi agents, ribozyme agents, and other nucleic acid-based methods of reducing gene expression, can be designed and tested based on known sequences of EPIC1 RNAs and gene structure (exemplary sequences are provided herein). Based on the present disclosure, one of ordinary skill can design, and/or produce an active agent capable of knocking down EPIC1 expression. Of note, a number of publications describe algorithms for generating candidate iRNA sequences, and publicly-available software can be used to implement those algorithms. As such, typically, one only needs to enter an mRNA sequence into a calculator to produce candidate iRNAs. That said, as shown in the examples below, not all RNAi agents are equal, and thus those including the sequences of:

```
                                              SEQ ID NO: 4
        (5'-CCUUCAGACUGUCUUUGAA-3'),

SEQ ID NO: 5
        (5'-GCUUUCUCUCGGAAACGUG-3'),

SEQ ID NO: 6
        (5'-AGUGUGGCCUCAGCUGAAA-3'),

SEQ ID NO: 7
        (5'-TGCCTTCAGACTGTCTTTGAA-3'),
        or

SEQ ID NO: 8
        (5'-GCTTTCTCTCGGAAACGTGAA-3'),
``` may be preferred in instances. RNAi agents that include sequences, such as the sequences of SEQ ID NOS: 4-8, may have 100% sequence identity with a portion or fragment of any one or more of SEQ ID NOS: 1-3 or a sequence complementary thereto, or may include one or more additional nucleobases at their 3' or 5' end, or may include one or more substitutions that do not substantially interfere with the activity of the RNAi agent in knocking down or silencing EPIC1 expression. Also, SEQ ID NOS: 1-3 are exemplary cDNAs of three isoforms of EPIC1. Alleles, mutations, or other variants or polymorphisms (e.g., single-nucleotide polymorphisms, SNPs) of EPIC1 sequences are possible, and as such effective agents, such as RNAi and antisense agents may be substituted to accommodate those variants. Further, some sequence mismatches in RNAi agents are not only tolerated, but may be beneficial (see, e.g., Wu, H., et al. "Improved siRNA/shRNA Functionality by Mismatched Duplex" PLoS One. 2011; 6(12): e28580). As such, sequences having up to 90% or 95% (two or one mismatches, respectively) sequence identity with SEQ ID NOS: 4-8 are expected, in many circumstances, to be effective RNAi agents.

In aspects, a useful antisense oligonucleotide, e.g., a nucleic acid or nucleic acid analog, comprises a sequence having at least 90% sequence identity, at least 95% sequence identity, or 100% sequence identity with SEQ ID NO: 9 (5'-GTCGACTCCTGCCGGA-3'). The antisense oligonucleotide may have the sequence of SEQ ID NO: 9. In aspects, the antisense oligonucleotide is an LNA.

Therefore, according to one aspect, provided herein is a method of treating cancer in a patient, comprising knocking down or silencing EPIC1 expression or activity to a level effective to treat a cancer in a patient. EPIC1 expression can be knocked down or silenced, e.g., by use of antisense nucleic acids, or by use of RNAi agents. In one aspect expression of the EPIC1 gene is silenced by administration of an RNAi agent to the patient, such as a siRNA, as described above and which are commercially available. Cancers in which Myc, e.g., c-Myc as is broadly-known is activated, meaning its expression and/or transcriptional activation function is increased, in a cancer cell. In one aspect, the cancer is breast cancer, e.g., luminal B or HER2 subtype breast cancer. In another aspect, the cancer is endometrial cancer, ovarian cancer, pancreatic cancer, or leukemia. As can be seen in the Examples below, knocking down or silencing EPIC1 RNA or expression also is useful as an adjunct to chemotherapy for the treatment of cancer, e.g. for treatment of a cancer in which Myc is activated. In one aspect, the cancer is breast cancer. In other aspects, the cancer is endometrial cancer, ovarian cancer, pancreatic cancer, or leukemia.

Chemotherapy agents include, for example and without limitation: histone deacetylase inhibitors, inhibitors of topoisomerase II, inhibitors of topoisomerase II, kinase inhibitors, nucleotide analogs and precursor analogs, peptide antibiotics, platinum-based agents, and vinca alkaloids and derivatives, such as, for example and without limitation: vorinostat, romidepsin, irinotecan, topotecan, etoposide, teniposide, tafluposide, bortezomib, erlotinib, gefitinib, imatinib, vemurafenib, vismodegib, azacitidine, azathioprine, capecitabine, cytarabine, doxifluridine, fluorouracil, gemcitabine, hydroxyurea, mercaptopurine, methotrexate, tioguanine, bleomycin, actinomycin, carboplatin, cisplatin, oxaliplatin, retinoids, tretinoin, alitretinoin, bexarotene, vinblastine, vincristine, vindesine, or vinorelbine. In one aspect, the chemotherapy agent is a Bromodomain and Extra-Terminal motif (BET) inhibitor, such as, for example and without limitation, one or more of: (+)-JQ1, I-BET151 (GSK1210151A), PFI-1 (PF-6405761), I-BET-762 (iBET762), or Apabetalone (RVX-208) (FIG. 2).

As shown in the Examples below, knocking down or silencing EPIC1 has the effect of reducing the occupancy of Myc protein on promoters of its target genes. Myc target genes are broadly-known, many of which are described in the Examples below. Thus, in another aspect, a method of reducing the occupancy of Myc protein on promoters of its target genes in a cell, comprising knocking down or silencing EPigenetically Induced lnCRNA1 (EPIC1) levels in the cell with a nucleic acid or nucleic acid analog able to knock down expression of EPIC1.

In aspects, by knocking down or silencing EPIC1 RNA expression or activity, it is meant any action that results in lower activity of EPIC1 in a cell or patient—typically by use of a therapeutic agent. Useful therapeutic agents include, without limitation, antisense or RNAi compositions.

U.S. Pat. No. 7,737,265 and International Patent Publication No. WO 2016/209862, each of which is incorporated herein by reference for its technical disclosure to the extent it is consistent with the present disclosure, are examples of the many publications disclosing further details regarding iRNA technology and RNAi agents, the disclosure of which is broadly applicable to methods of making and using agents for use in knocking down or silencing EPIC1 expression, as described herein. Disclosed in WO/2016/209862 are details relating to iRNA structure, definition of required sequences and agent size, definitions and descriptions of target sequences, methods of making iRNAs, variations or modifications in iRNA structures, such as nucleic acid analogs or mimetics, methods of modification of iRNAs such as ligand-modified iRNAs, including polysaccharide-modified or polypeptide-modified iRNAs and linkers that can be useful in targeting the iRNA, pharmaceutical compositions for delivery of iRNAs, delivery methods and delivery routes for iRNAs, including liposome or micellar delivery systems, and methods of determining whether iRNAs are effective. One of ordinary skill in the art can identify and optimize EPIC1 RNAi agents based on available knowledge and resources. Further disclosure of how to identify, make, or use EPIC1 RNAi agents is unnecessary.

EXAMPLES

Provide herein are methods and compositions to detect and target a specific group of cancer-related long non-coding RNAs (lncRNAs). The lncRNAs are specifically overexpressed by epigenetic mechanism in tumor tissues and not expressed in normal tissues. Such lncRNAs can be used as biomarkers for cancer diagnosis. One of the identified lncRNAs, referred to as EPIC1 (EPigenetically Induced lnCRNA 1), regulates tumor cell proliferation by directly interacting with oncogene Myc. Inhibitors of EPIC1 suppress tumor growth in both tumor cell lines and animal models. These EPIC1 inhibitors can be used in tumor therapy. Further, EPIC1 is implicated with drug resistance in cancers, and by knocking down expression of EPIC1, drug therapies and immunotherapies are shown herein to have increased efficacy.

Example 1

The epigenetic landscape of long noncoding RNAs (lncRNAs) was systematically characterized across 6,475 tumors and 455 cancer cell lines. This analysis revealed a recurrent hypomethylation phenotype of 1,006 lncRNAs in tumors, in stark contrast to the established CpG island hypermethylation phenotype (CIMP) of protein-coding genes. The lncRNA that is most frequently activated in 20 cancer types is EPigenetically Induced lnCRNA1 (EPIC1). Knockdown of EPIC1 led to breast cancer cell cycle arrest, suppression of colony formation, and inhibition of tumor growth in vitro and in vivo. EPIC1 knockdown reduces the occupancy of Myc protein to the promoters of its target genes (e.g., p21, CCNA2, CDC20, and CDC45) without influencing Myc expression. EPIC1 interacts with the 148-220 amino acid region of Myc through EPIC1's 129-283 nt region. Overexpression of EPIC1 increased Myc target expression and breast tumorigenesis in vitro and in vivo, which can be abolished by Myc knockdown.

Cell Culture, RNA Interference, LNA Transfection, and Plasmid Transfection: Human breast epithelial cell line, MCF10A, and human breast cancer cell lines, BT-20, BT-474, HCC1937, Hs578T, MCF-7, MDA-MB-231 (MB231), MDA-MB-361 (MB361), MDA-MB-468 (MB468), T-47D, and ZR-75-1, and human ovarian cancer cell lines, SK-OV-3, and NIH: OVCAR-3, and human pancreatic cancer cell lines, AsPC-1, BxPC-3, and PANC-1, and human prostate cancer cell lines, DU 145, and PC-3, and human leukemia cell line K562, and human lung cancer cell line A549, and human cervical cancer cell line HeLa, and human liver cancer cell line Hep G2, and human embryonic kidney (HEK) 293T cells were purchased from American Type Culture Collection (ATCC) and cultured as suggested by ATCC's guidelines. Human ovarian cancer cell lines, IGR-OV-1, OVCAR-4, and OVCAR-8 were purchased from NIH/NCI and kept in RPMI 1640 medium supplemented with 10% fetal bovine serum (FBS), 1% penicillin, and 1% streptomycin. The A2780 human ovarian cancer cell line and the cisplatin resistant version of the cell line, A2780cis, were obtained from the European Collection of Cell Cultures (ECACC), supplied by Sigma-Aldrich, and cultured in RPMI 1640 medium supplemented with 2 mM glutamine, 10% FBS, 1% penicillin, and 1% streptomycin; A2780cis cells were also supplemented with 1 mM cisplatin. Human pancreatic duct epithelial cell line (HPDE), and phoenix cells were kindly provided by Dr. Wen Xie (Department of Pharmaceutical Sciences, University of Pittsburgh), and HPDE cells were maintained in Keratinocyte-SFM medium supplemented with human recombinant epidermal growth factor and bovine pituitary extract (ThermoFisher, #17005042) and phoenix cells were maintained in DMEM supplemented with 10% FBS, 1% penicillin, and 1% streptomycin.

For RNA interference, cells were transfected with 40 nM siRNA targeting EPIC1, Myc, or a control siRNA using Lipofectamine RNAiMAX (ThermoFisher, #13778150) per the manufacturer's instructions. Total RNA was isolated 72 hr later for real-time PCR analysis. The siRNA sequences are SEQ ID NOS: 4-6.

For LNA transfection, cells were transfected with 40 nM LNA oligos targeting EPIC1, and a scramble control using Lipofectamine™ RNAiMAX per the guidelines. The LNA oligos (e.g., SEQ ID NO: 9) were designed and synthesized from Exiqon.

For plasmid transfection, cells were transfected with plasmid using Lipofectamine™ 2000 (ThermoFisher, #11668019) or Lipofectamine™ 3000 (ThermoFisher, #L3000015) as suggested approaches.

In Vivo Xenograft Model: Briefly, 5- to 6-week-old female athymic nude mice (Charles River) were used for the xenograft model. MCF-7 cells stably expressing shCtrl and shEPIC1 were trypsinized and washed twice with sterilized PBS, and then, 0.2 ml of PBS containing $5 \times 10^6$ cells was subcutaneously inoculated into the flanks of the mice. Mice were monitored twice every week for tumor growth, and tumor size was measured using a caliper. Tumor volume in $mm^3$ was calculated using the formula: Tumor volume=$0.5 \times$ $(width)^2 \times length$. Eight weeks after inoculation, mice were sacrificed in keeping with the policy for the humane treatment of tumor-bearing animals.

Data Collection: DNA methylation, PCG expression, whole-exome mutation and GISTIC copy number alteration data were downloaded from TCGA Pan-Cancer project (Data Freeze 1.3). The lncRNA annotation was downloaded from GENCODE (V22, GRCh38). There were 7,656 intergenic, 5,565 antisense, and 920 sense intronic lncRNAs. H3K4me3 and H3K27ac ChIP-seq data for seven cell lines were down-loaded from the UCSC genome browser: Integrated Regulation from ENCODE Tracks. DNA methylation data for breast cancer cell lines were downloaded from GSE57342 and GSE44837.

RNA-seq data from 781 cancer cell lines in the CCLE database were downloaded from Expression Atlas (E-MTAB-2770). HM450 DNA methylation profile of 1,028 cancer cells lines form COSMIC database. There are 455 cells which have both HM450 DNA methylation and RNA-seq data. The BAM files of RNA-seq of 939 breast cancer tumors were downloaded from Cancer Genomics Hub.

Mapping the Probes to GENCODE Genes: The genomic coordinates of HM450 probes based on GRCh37 were first transferred to genomic coordinates in GRCh38 using Lift-Over (UCSC genome browser). The nearest TSS of PCG and lncRNA for each probe was identified based on GENCODE V22 annotation. In this way, we defined: (1) the PCG probes, located in the PCG promoter region (+/− 3 kb from the TSS); (2) the lncRNA probes, located in the lncRNA promoter region; (3) the shared probes, located in both the PCG and lncRNA promoter regions; and (4) the non-probes, which are not located in any promoter regions.

DNA Methylation Dysregulation Pattern Analysis in Cancers: DNA methylation dysregulation in cancers showed a different beta value pattern in lncRNA promoter and protein-coding promoter regions. To evaluate the statistical significance of the difference between methylation in lncRNA and PCG promoter regions, we permuted the annotation for each probe 10,000 times to generate an experimental distribution of DNA methylation change. Through comparison with the experimental distribution, an empirical p value could be calculated. Finally, the weighted two-dimensional kernel density estimation R function kde2d.weighted (package: ggtern) was used to measure the distribution of hypomethylation or hyper-methylation according to the distance to promoters of lncRNA and PCGs.

Statistical and Clustering Analysis: Student's t-test, analysis of variance, chi-square, Wilcoxon rank-sum test, Fisher's exact test, Kaplan-Meier estimate, and Mantel-Cox survival analyses were performed using R 2.10.0. Significance was defined as $p<0.05$. Benjamini-Hochberg multiple testing correction was used to estimate the FDR when multiple testing correction was applied.

Integrating ChIP-Seq and RNA-Seq Data to Identify and Validate EPIC1-Myc Axis Target Gene: The genome-wide Myc protein binding sites were identified by applying Cistrome algorithm on two biological replicates of Myc ChIP-seq assays of MCF-7 cells. We identified Myc targets that regulated by EPIC1 based on two criteria: (1) at least one Myc binding peak falls within the TSS-proximal region (from 3 kb upstream to 500 bp downstream) of the gene; and (2) the gene is differentially expressed between the siEPIC1 and control MCF-7 cells. The top targets of EPIC1-Myc axis were selected based on their significance of Myc binding signal, differential expression after EPIC1 knockdown, and their roles in cell proliferation/cycle. For each target, primers were designed to target the Myc binding region. ChIP-qPCR was further performed to demonstrate whether EPIC1 knockdown decreases the recruitment of Myc to its target promoter sites.

Antibodies: The following antibodies were used for immunoblotting: rabbit anti-SNRP70 (Abcam, #ab83306), rabbit anti-GAPDH (Santa Cruz, #sc-25778), rabbit anti-Myc (Cell Signaling, #13987), rabbit anti-p21 (Cell Signaling, #2947), rabbit anti-CDC20 (Cell Signaling, #14866), rabbit anti-FLAG (Cell Signaling, #14793), rabbit anti-CDC45 (Cell Signaling, #11881), rabbit anti-MAX (Novus, #NBP1-49963), mouse anti-Cyclin A2 (Santa Cruz, #sc-596), and mouse anti-b-actin (Sigma, #A5441). The following antibodies were used for co-immunoprecipitation (Co-IP), RNA immunoprecipitation (RIP) and chromatin immunoprecipitation (ChIP) analysis: rabbit anti-Myc (Santa Cruz, #sc-789), rabbit anti-MAX (Santa Cruz, #sc-764), rabbit anti-Myc (Cell Signaling, #9402), and normal rabbit IgG (Cell Signaling, #2729) as a negative control, and anti-FLAG M2 affinity gel (Sigma, #A2220).

Cell Fractionation, Cytoplasmic/Nuclear RNA Isolation: MCF-7, Hs578T, and T-47D cells were subjected to cytoplasmic and nuclear fractionation using a PARIS™ kit (ThermoFisher, #AM1921), and total RNA was isolated from each fraction following the recommended protocol.

RNA Isolation and Quantitative Real-Time PCR (qRT-PCR) Assays: Total RNA was isolated from cultured cells using an RNeasy Mini kit (Qiagen, #74104) according to the manufacturer's instructions. cDNAs were synthesized from 0.5 mg of total RNA using a High-Capacity cDNA Reverse Transcription Kit (Applied Biosystems, #4368813). Real-time PCR was performed with Power SYBR Green PCR Master Mix (Applied Biosystems, #4367659) on a QuantStudio 6 Flex Real-Time PCR System (Applied Biosystems). Relative gene expression was determined by DDCt normalized to GAPDH.

EPIC1 RNA Copy Number Analysis: Total RNA was isolated from $1\times10^6$ cells using an RNeasy Mini kit. The full-length of EPIC1 RNA was in vitro transcribed with Ribo-nucleotide solution set (NEB, #N0450) and T7 RNA polymerase (Roche, #10881775001) using the PCR products as a template, treated with RNase-free DNase I (Promega, #M198A), and then isolated with the RNeasy Mini kit. cDNA was synthesized using 1 mg of the total RNA or full-length of EPIC1 RNA. Serial ten-fold dilutions ($10^2$ to $10^9$ molecules per ml) of cDNA from in vitro-tran-scribed EPIC1 RNA were used as a reference molecule for the standard curve calculation. Real-time PCR was performed as above.

Cloning, shRNA Construction, and Lentiviral Transduction: Full-length of EPIC1 was identified and amplified from total RNAs of MCF-7/T-47D cells by 5'RACE and 3'-RACE using FirstChoice RLM-RACE Kit (ThermoFisher, #AM1700). To construct retroviral EPIC1 expression plasmids, PCR products containing the CMV-zsGreenl portion of pLncEXP (Addgene plasmid # 64865) were inserted into a pBABE puro vector (Addgene, #1764), and the resulting construct was named as pBABE-lnc. Then full-length and truncated mutants of EPIC1 were cloned into pBABE-lnc with AgeI and XhoI enzymes or cloned into pCDH-CMV-MCS-EF1-Puro (System Biosciences, #CD510B-1) with XbaI and EcoRI enzymes. Full-length of Flag-tagged or HA-tagged Myc expression vectors were generated using a human Myc cDNA Clone (OriGene, #SC112715) as a DNA template. Full-length of HA-tagged MAX expression vector was generated using cDNA from MCF-7 cells as a template. The truncated or deletion mutants and LNA-resistant EPIC1 expression vectors were constructed by using QuickChange II XL Site-Direct Mutagenesis Kit (Agilent Technologies, #200522). All constructs were confirmed by DNA sequencing.

To construct stable EPIC1-expressing cells, pBABE-lnc and lnc-EPIC1 plasmids were transfected into Phoenix cells to produce retrovirus, and viruses were collected 48 hr post-transfection. MCF-7 cells were infected for 24 hr with the retroviruses and selected with puromycin to establish stable EPIC1-expressing cells.

EPIC1 knockdown constructs were cloned by inserting oligos into a pLKO.1 TRC cloning vector (Addgene, #10878, See, e.g., FIG. 3). To produce lentiviral particles, HEK 293T cells were seeded into one 6-cm Petri dish in DMEM with 10% FBS without antibiotics and incubated overnight to reach approximately 80% confluence before transfection. Transfection was performed using Lipofectamine 2000 Transfection Reagent according to the recommended protocol. Then, 3 mg of pLKO.1 shControl (shCtrl) or pLK0.1 shEPIC1 plasmid, 2.25 mg of psPAX2 (Addgene, #12260), and 0.75 mg of pVSV-G (Addgene, #8454) were used for each 6-cm petri dish. After transfection for 6 hr, the medium was changed with fresh DMEM containing 10% FBS, and the cells were incubated for another 48 hr. Culture medium containing the lentiviral particles was collected and filtered through a 0.45 mm filter to remove any remaining cells and debris. Target cells were infected for 24 hr with lentiviral particles in the presence of 8 mg/ml polybrene and screened with puromycin to establish stable cells.

Promoter Cloning and Reporter Assay: Using genomic DNA from MCF-7 cells as DNA templates, the promoter region of CCNA2 ranging from −443 bp to +334 bp was amplified by PCR and inserted to pGL3 Basic vector (Promega, #E1751) with NheI and HindIII enzymes, named as CCNA2-Luc, and the promoter region of EPIC1 ranging from −133 bp to +587 bp were inserted to pGL3 Basic vector with HindIII enzymes, named as EPIC1-Luc. WWP-Luc (p21/WAF1 promoter) was a gift from Bert Vogelstein (Addgene plasmid #16451). For plasmid methylation followed by the previous report (DiNardo et al., 2001), briefly, 20 mg of EPIC1-Luc were methylated using Methyltransferase (M. SssI, NEB, #M0226S) at 37° C. for 12 hr, followed by subsequent inactivation of enzyme at 60° C. for 20 min. Mock-methylated mixtures were also performed in the absence of the methylase and S-adenosyl methionine. The methylated and mock-methylated mixtures were purified using QlAprep Spin Miniprep Kit (Qiagen, #27106) and the methylation status of the constructs was determined by HpaII digestion and 2% agarose gel eletrophoresis.

Cells were transiently transfected with un-methylated or methylated EPIC1-Luc reporter or a combination of either EPIC1siRNA, MycsiRNA, or a negative control siRNA with CCNA2-Luc or WWP-Luc constructs using Lipofectamine™ 2000, and b-Gal was used as an internal control. After 48 hr, the luciferase and b-Gal activities were detected in a Wallac 1420 Victor Microplate Reader (Perkin Elmer). The luciferase activities were normalized to the b-Gal activities. Data were shown as fold change over the control group.

Cell Proliferation and Cell Cycle Assay: Cells were seeded at 2,000 cells per well in 96-well culture plates, and MTT assays were performed with a CellTiter 96 Non-Radioactive Cell Proliferation Assay Kit (Promega, #G4100) following the manufacturer's guidelines. The absorbance value was measured at 570 nm using an xMark Microplate Spectrophotometer (Bio-Rad) with a reference wavelength of 630 nm.

For the cell cycle assay, cells were collected, rinsed with PBS, and fixed for a minimum of 2 hr by adding 70% ice-cold ethanol at −20° C. Cells were then sequentially washed once in PBS and BD Pharmingen stain buffer (BD Biosciences, #554656). Cell pellets were resuspended in 0.5 ml of BD Pharmingen PI/RNase staining buffer (BD Biosciences, #550825) and incubated for 15 min at room temperature (RT), and cells were immediately analyzed using an LSRFORTESSA X-20 flow cytometer (BD Biosciences). The data were analyzed with FlowJo software.

Soft Agar Colony Formation Assay: For each well, 2 ml of 0.6% NuSieve GTG agarose (Lonza, #50081) in culture medium was plated into 6-well plates as the bottom layer, and the agarose was allowed to solidify at RT. Then, 1 ml of cell mixture containing $10^4$ cells in culture medium and a final con-centration of 0.35% agarose was carefully plated on top of the bottom layer. The plates were incubated at 37° C. and 5% $CO_2$ until colonies were formed, and cells were fed with 0.5 ml of cell culture medium every other week. After 2-3 weeks, colonies were stained using 0.005% crystal violet in 4% paraformaldehyde solution and counted.

RNA Immunoprecipitation (RIP): RIP was performed as follows. Briefly, cultured cells were collected by trypsinization, washed once with cold PBS, and then treated with 0.3% formaldehyde in PBS for 10 min at 37° C. Then, 1.25 M glycine dissolved in PBS was added to a final concentration of 0.125 M, and the mixture continued to incubate for 5 min at RT. The cells were subsequently washed twice with cold PBS, and the pellets were resuspended in RIPA buffer (50 mM Tris-HCl, pH 7.4, 150 mM NaCl, 1 mM EDTA, 0.1% SDS, 1% NP-40, 0.5% sodium deoxycholate, 0.5 mM DTT, 1 mM PMSF, and 1 x protease inhibitor cocktail (Sigma, #P8340)) and incubated on ice for 30 min with shaking. The cleared lysates were incubated for 4 hr at 4° C. with the corresponding antibodies. Pellets were washed twice in RIPA buffer, four times in 1 M RIPA buffer (50 mM Tris-HCl, pH 7.4, 1 M NaCl, 1 mM EDTA, 0.1% SDS, 1% NP-40, and 0.5% sodium deoxycholate), and then twice in RIPA buffer. The pellets were resuspended and treated with RIPA buffer containing proteinase K at 45° C. for 45 min. Finally, RNA was isolated with TRIzol reagent.

RNA Pull-Down Assay: Biotin-labeled full-length and truncated fragments of EPIC1 RNA were transcribed in vitro with a Biotin RNA Labeling Mix Kit (Roche, #11685597910) and T7 RNA polymerase (Roche, #10881775001) using the PCR products as a template, treated with RNase-free DNase I (Promega, #M198A), and then isolated with an RNeasy Mini kit. Biotinylated RNA was folded in RNA structure buffer (10 mM Tris-HCl pH 7.0, 0.1 M KCl, 10 mM MgCl2) at 90° C. for 2 min, immediately put on ice for another 2 min, and then transferred to RT for 20 min to allow proper RNA secondary structure formation.

Cells were collected by trypsinization and washed twice with sterilized PBS. Cell pellets were resuspended in 2 ml of pre-chilled PBS, 2 ml of nuclear isolation buffer (1.28 M sucrose, 40 mM Tris-HCl pH 7.5, 20 mM MgCl2, and 4% Triton X-100) and 6 ml of sterilized DEPC-treated water and incubated on ice for 20 min with frequent vortexing. Nuclei were pelleted by centrifugation at 2,500 g for 15 min, washed once with 1 ml of nuclear isolation buffer, resuspended in RIP buffer (150 mM KCl, 25 mM Tris-HCl pH 7.4, 0.5 mM DTT, 0.5% NP-40, 1 mM PMSF, 1× Superase-in, and 1× protease inhibitor cocktail), and sheared on ice using a Dounce homogenizer with 15 to 20 strokes. After 1 mg of the cleared lysate was mixed with folded RNA in RIP buffer and incubated for 1 hr at RT, 60 ml of Dynabeads MyOne Streptavidin C1 magnetic beads (ThermoFisher, #65001) was added to each reaction, and the mixture was incubated for another 1 hr at RT. Beads were washed five times and boiled in 1× SDS loading buffer, and the retrieved protein was analyzed using western blotting.

The in vitro binding assay of biotin-labeled EPIC1 RNA and Myc protein was performed. Briefly, 0.1 mg of biotinylated RNA was incubated with different amounts of recombinant human Myc protein (Abcam, #ab84132) for 1 hr at RT in 200 ml of binding buffer (50 mM Tris-HCl pH 7.9, 10% glycerol, 100 mM KCl, 5 mM $MgCl_2$, 10 mM b-ME, 0.1% NP-40, 1 mM PMSF, 1× Superase-in, and 1× protease inhibitor cocktail). Then, 30 ml of washed streptavidin-conjugated magnetic beads were added to each reaction, and the mixtures were incubated at RT for 30 min. Beads were washed five times and boiled in 1× SDS loading buffer, and the retrieved protein was analyzed using western blotting.

Chromatin Immunoprecipitation (ChIP): The ChIP assay was performed as follows. Briefly, $1 \times 10^7$ cells were cross-linked with a final concentration of 1.42% formaldehyde in growth medium for 15 min at RT, and cross-linking was quenched by the addition of glycine to a final concentration of 125 mM and incubation for 5 min at RT. Cells were rinsed twice with cold PBS, harvested in IP buffer (50 mM pH 7.5 Tris-HCl, 150 mM NaCl, 5 mM EDTA, 0.5% NP-40, and 1% Triton X-100) supplemented with 1 mM PMSF and 1× protease inhibitor cocktail and sonicated to shear the chromatin to yield DNA fragment sizes of 0.5 to 1 kb. Samples were cleared by centrifuging at 12,000 g for 10 min at 4° C. and preincubated for 1 hr with 40 ml of protein A/G agarose beads. A portion of the precleared samples was used as input DNA. Then, approximately 2 mg of Myc antibody or rabbit normal immunoglobulin (IgG) was added to the remainder of the samples and incubated for 1 hr at 4° C., 40 ml of protein A/G agarose beads (ThermoFisher, #20421) were added, and the mixture was incubated for 4 hr at 4° C. Beads were washed six times with cold IP buffer, and DNA was isolated with 10% Chelex following the suggested protocol; the total input DNA was also isolated. Quantification was performed using real-time PCR with SYBR Green Master Mix. Control IgG and input DNA signal values were used to normalize the values from the Myc ChIP to target genes. The primers for target genes and the negative control are listed in Table S5.

Co-Immunoprecipitation (Co-IP), Protein Isolation and Western Blotting: Co-IP was performed as following, briefly, cells were collected and lysed in lysis buffer (50 mM Tris-HCl pH 7.5, 150 mM NaCl, 1 mM EDT, 1% Triton X-100, PMSF freshly added to a final concentration of 1mM, and 1× protease inhibitor cocktail). After quantification using a BCA protein assay kit (ThermoFisher, #23225), 1 mg of total protein were used for Co-IP and incubated for overnight with 2 mg of anti-Myc, anti-MAX antibodies, and normal rabbit IgG as a negative IP control, respectively. The mixtures were incubated for another 2-4 hr with protein A/G agarose beads, and then beads were washed at least 4 times, and treated and boiled for 10 min with 1× SDS sample buffer (Bio-Rad, #161-0737).

Cell lysates were also treated with equal volume of 2× SDS sample buffer and resolved by SDS-PAGE under denaturing conditions and transferred onto PVDF membranes (Bio-Rad, #162-0177). The membranes were blocked with 5% non-fat milk (LabScientific, #M0841) in 1× PBST at RT for 2 hr and incubated with primary antibody overnight at 4° C., followed by incubation with horseradish peroxidase-conjugated secondary antibodies for 1 hr at RT. Specific bands were visualized with enhanced chemiluminescence (ECL) substrate (ThermoFisher, #32106) and exposed onto films with an AX 700LE film processor (ALPHATEK).

Data And Software Availability: The RNA-seq datasets for gene expression in MCF-7 cells after siRNA-mediated knockdown of EPIC1 (Accession No. GSE98538), DNA methylation datasets of breast cancer cells (Accession No. GSE57342 and GSE44837), and gene expression profile of breast cancer patients (Accession Nos. GSE20711, GSE21653, GSE17907, GSE20685, GSE16446, and GSE19615), are available at GEO: https://www.ncbi.nlm.nih.gov/geo/.

Results

LncRNA Promoters Exhibit a Distinct Pattern of Epigenetic Alterations in Cancer Compared with PCG Promoters: To interrogate lncRNA DNA methylation in cancer, we developed a computational pipeline to repurpose HM450 probes to lncRNA promoters. This analysis resulted in a set of 225,868 probes annotated to 28,366 genes. Specifically, 66,832 HM450 probes were annotated to 9,606 lncRNA genes (29,117 CpG islands), comprising approximately 60.4% of all lncRNAs in ENCODE annotation. The lncRNAs that had at least one HM450 probe covering their promoters included 3,964 intergenic and 4,053 antisense lncRNA genes. The median distances between lncRNA promoters and their nearest HM450 probes is 1,267 bp. The identified DNA methylation probes are mainly located within 3 kb regions of H3K4me3 and H3K27ac peaks of their mapped genes, suggesting that the probes indeed represent the promoter methylation status of lncRNAs and PCGs. We first sought to determine the lncRNA DNA methylation pattern in cancer by comparing the DNA methylation profile of lncRNA promoters between tumors and normal tissues using the TCGA Pan-Cancer database (syn4382671). Because the CpG island hypermethylation phenotype (CIMP) has been established as one of the hallmarks in many cancer types, we originally expected to identify hypermethylated tumor-suppressing lncRNAs. Intriguingly, we observed both hypermethylated and hypomethylated lncRNA promoters in breast cancer tissues. This observation is in stark contrast to the PCG promoters, which were predominantly hypermethylated in breast cancer. Of the intergenic lncRNAs that do not share promoters with PCGs, there were 504 intergenic lncRNA promoters showing significant hypomethylation and 639 intergenic lncRNA promoters showing significant hypermethylation in breast cancer (false discovery rate [FDR] <0.05 and effect size >0.2). The hypomethylation pattern of lncRNA promoters was consistently observed in another nine cancer types that also had matched normal tissues available. To determine if this observation was an artifact due to bias of the HM450 microarray design, we randomly permuted the labels of lncRNAs and PCGs for 10,000 times and generated an empirical distribution to estimate the FDR for each promoter. This analysis revealed that the lncRNA promoters were significantly hypomethylated in all ten cancer types ($p<10^{-15}$, Kolmogorov-Smirnov test).

Figure 4:
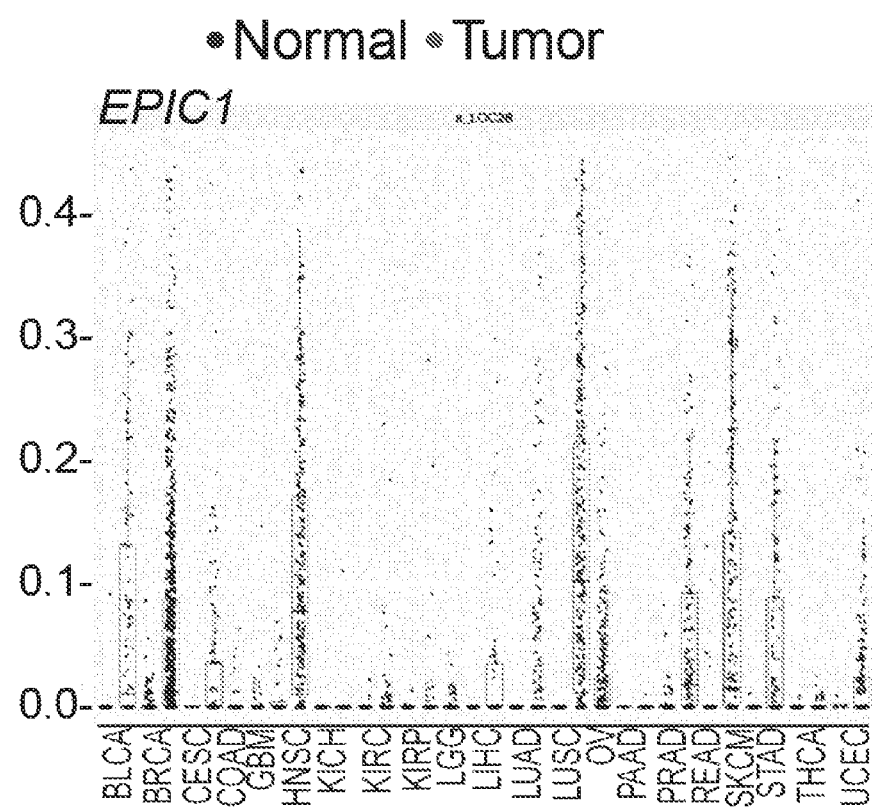
FIG. 4 is a graph showing a representative expression pattern of EPIC1 in multiple cancer types, compared with normal tissues. Red dots (in original) denote tumor, and blue dots (in original) denote normal tissue.

Integrative Analysis Identified 2,123 Recurrent Epigenetically Regulated lncRNAs in 20 Cancer Types: To determine whether lncRNAs' expression is regulated by the DNA methylation changes at their promoters (e.g., hypomethylation causes overexpression), we integrated the lncRNA expression data from MiTranscriptome, which summarized the expression of 12,382 cancer-associated lncRNA transcripts using an ab initio assembly method in 6,475 RNA sequencing (RNA-seq) profiles, including 5,602 TOGA samples. Our analysis focused on TOGA samples across 20 cancer types that have both DNA methylation and lncRNA expression data. We applied a heuristic strategy to identify the lncRNAs that are epigenetically activated (EA) or epigenetically silenced (ES) in tumors in comparison to their DNA methylation status in normal tissues. This method prioritized the lncRNAs that not only exhibited a significant difference in DNA methylation between tumors and normal tissues, but also exhibited expression changes highly correlated with their DNA methylation alterations. A patient-centric matrix with DNA methylation status of 2,123 lncRNA genes across 20 cancer types was characterized, including 1,006 EA and 1,117 ES lncRNAs that showed epigenetic alteration in at least one cancer type. All the epigenetically regulated lncRNAs, with either hypomethylation or hypermethylation in tumors, exhibited a significant negative correlation (FDR <0.01) between their expression and promoter DNA methylation status. Notably, a group of the EA lncRNAs in tumors was not expressed in normal tissues (FIG. 4). This "on or off" expression pattern of EA lncRNAs potentiated them as promising diagnostic biomarkers. To further validate the methylation status of the lncRNAs and their expression in cancer, we investigated the RNA-seq and HM450 DNA methylation profiles of 455 cancer cell lines from the CCLE and COSMIC databases. Among the top 40 lncRNAs, 34 (14 EA and 20 ES lncRNAs) exhibited a similar expression pattern in cancer cell lines and significantly negative correlation between their expression and promoter methylation.

Abbreviations for FIG. 4: BLCA=Bladder Urothelial Carcinoma; BRCA=Breast invasive carcinoma; CESC=Cervical squamous cell carcinoma and endocervical adenocarcinoma; COAD=Colon adenocarcinoma; GBM=Glioblastoma multiforme; HNSC=Head and Neck squamous cell carcinoma; KICH=Kidney Chromophobe; KIRC=Kidney renal clear cell carcinoma; KIRP=Kidney renal papillary cell carcinoma; LGG=Brain Lower Grade Glioma; LIHC=Liver hepatocellular carcinoma; LUAD=Lung adenocarcinoma; LUSC=Lung squamous cell carcinoma; OV=Ovarian serous cystadenocarcinoma; PAAD=Pancreatic adenocarcinoma; PRAD=Prostate adenocarcinoma; READ=Rectum adenocarcinoma; SKCM=Skin Cutaneous Melanoma; STAD=Stomach adenocarcinoma; THCA=Thyroid carcinoma; UCEC=Uterine Corpus Endometrial Carcinoma.

Epigenetically Regulated lncRNAs Are Associated with Tumor Survival and Protein-Coding Cancer Gene Alterations: We next analyzed the association of lncRNA epigenetic status with patient survival in 20 cancer types. Twelve of the top 20 EA lncRNAs were significantly correlated with poor survival in at least 1 cancer type, while 10 of the top 20 ES lncRNAs were significantly correlated with favorable survival. To explore the relationship between lncRNA epigenetic alterations and the somatic alterations of known tumor genes, we integrated the lncRNA epigenetic alterations with the mutation and copy-number alterations of known protein-coding cancer genes in the same tumors. Notably, the epigenetically regulated lncRNAs show a strong co-occurrence with a group of cancer gene mutations and copy-number alterations. For example, EA lncRNAs are significantly enriched in TP53 mutated tumors in multiple cancer types. By contrast, ES lncRNAs exhibit significant mutual exclusivity with EGFR amplifications and mutations.

Figure 5A:
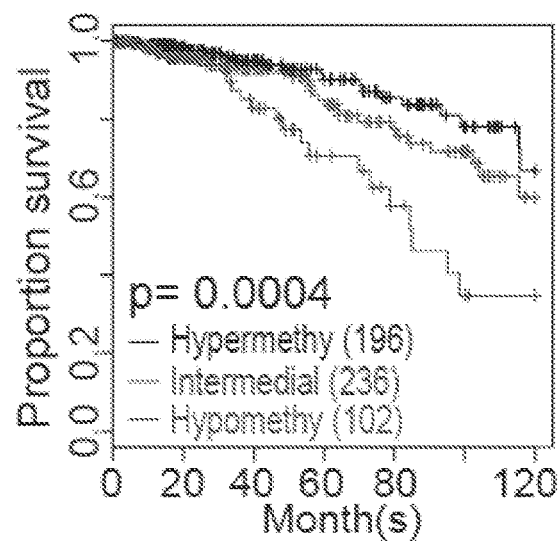
FIGS. 5A-5C. Expression Level of EPIC1 Is Regulated by DNA Methylation and associated with poor survival in breast cancer patients.
Figure 5B:
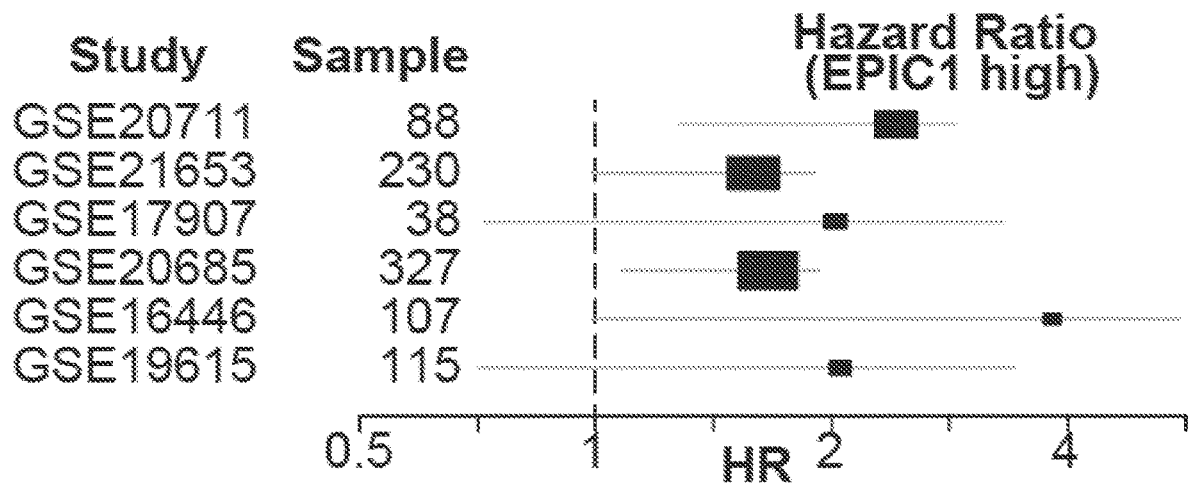
Figure 5C:
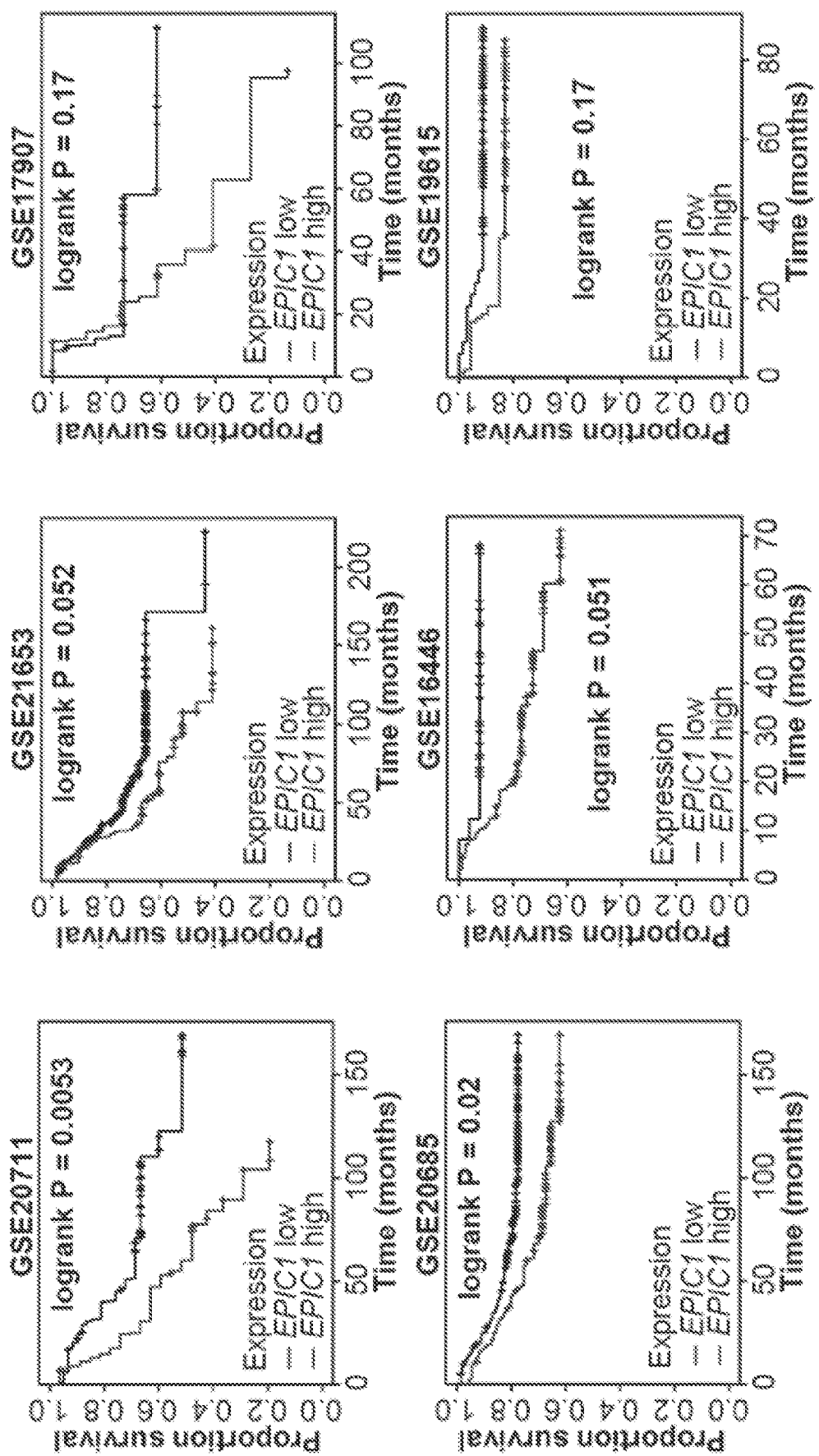

EPIC1 Is Epigenetically Activated and Correlated with Poor Survival in Breast Cancer: The lncRNA that is most frequently epigenetically activated in multiple cancer types is ENSG00000224271 (epigenetically induced lncRNA1 [EPIC1]). It is an intergenic lncRNA (CPAT coding probability=0.004) located on chr22:q13.31. There are CpG islands within 164 bp downstream of this gene's transcription start site. This lncRNA is epigenetically activated in up to 90% of tumor samples across ten cancer types, including breast cancer. Our algorithm identified three probes in HM450 mapping to the EPIC1 CpG islands. Based on the beta values of three probes, three subgroups of breast cancer were identified by the hierarchical clustering analysis in 534 breast tumors. The hypermethylated subgroup includes 196 (36.7%) breast tumors and exhibits a high EPIC1 methylation level similar to that in normal breast tissues. Breast tumors of this sub-group are characterized by reduced EPIC1 expression and an improved overall survival in comparison to the other two groups (FIG. 5A). In contrast, patients whose tumors exhibit EPIC1 hypomethylation and increased EPIC1 expression have the worst survival (FIG. 5A). To determine if EPIC1 expression is robustly associated with poor patient survival in breast cancer, we re-annotated the probes from five Affymetrix microarrays to lncRNAs and identified one probe (1563009_at) in an Affymetrix HG-U133plus2 microarray that specifically detected EPIC1 expression. As shown in FIG. 5B, increased expression of EPIC1 was consistently associated with poor survival in 6 independent patient cohorts, including 905 breast tumors (FIGS. 5B and 5C).

Further analysis revealed that EPIC1 epigenetic activation is significantly associated with luminal B and HER2 subtypes of breast cancer (p<0.001). In 119 TOGA luminal B tumors, patients with EPIC1 epigenetic activation demonstrated significant poor survival (p=0.002). The association between EPIC1 and breast cancer poor survival remains significant after adjusting cancer subtypes along with other prognostic factors including age and clinical stage (multivariate Cox regression model p=0.02). In all 20 cancer types assessed, EPIC1 epigenetic activation is also significantly correlated with poor survival in endometrial cancer patients (UCEC).

Using RNA-seq and HM450 DNA methylation data in the COLE database, we observed a significant negative correlation (p<0.05) between endogenous EPIC1 expression levels and its promoter methylation in 24 breast cancer cell lines. Among them, 18 cell lines showed epigenetic activation of EPIC1, while 4 (i.e., MB231, HCC1937, CAMA1, and ZR-75-30) exhibited promoter hypermethylation and had low EPIC1 expression. Decitabine treatment caused a dosage- and time-dependent EPIC1 expression and demethylation in EPIC1 hypermethylated cell lines (e.g., MB231), but not in cells that already exhibit EPIC1 hypomethylation and overexpression (e.g., MCF-7). Using a similar strategy, we selected seven other EA lncRNAs based on their novelty and demonstrated that decitabine treatment significantly induced EA lncRNAs expression by decreasing the DNA methylation level of their CpG islands.

To determine if EPIC1 is directly regulated by DNA methylation, we cloned EPIC1's promoter region (including the CpG islands) and performed in vitro DNA methylation assay. Luciferase reporter assays revealed that the unmethylated EPIC1 promoter (unMeth-EPIC1) led to a significantly higher reporter activity compared with the methylated version (Meth-EPIC1) (p<0.01). Collectively, these results demonstrated that EPIC1 is directly regulated by DNA methylation at the CpG islands in its promoter region.

Figure 6A:
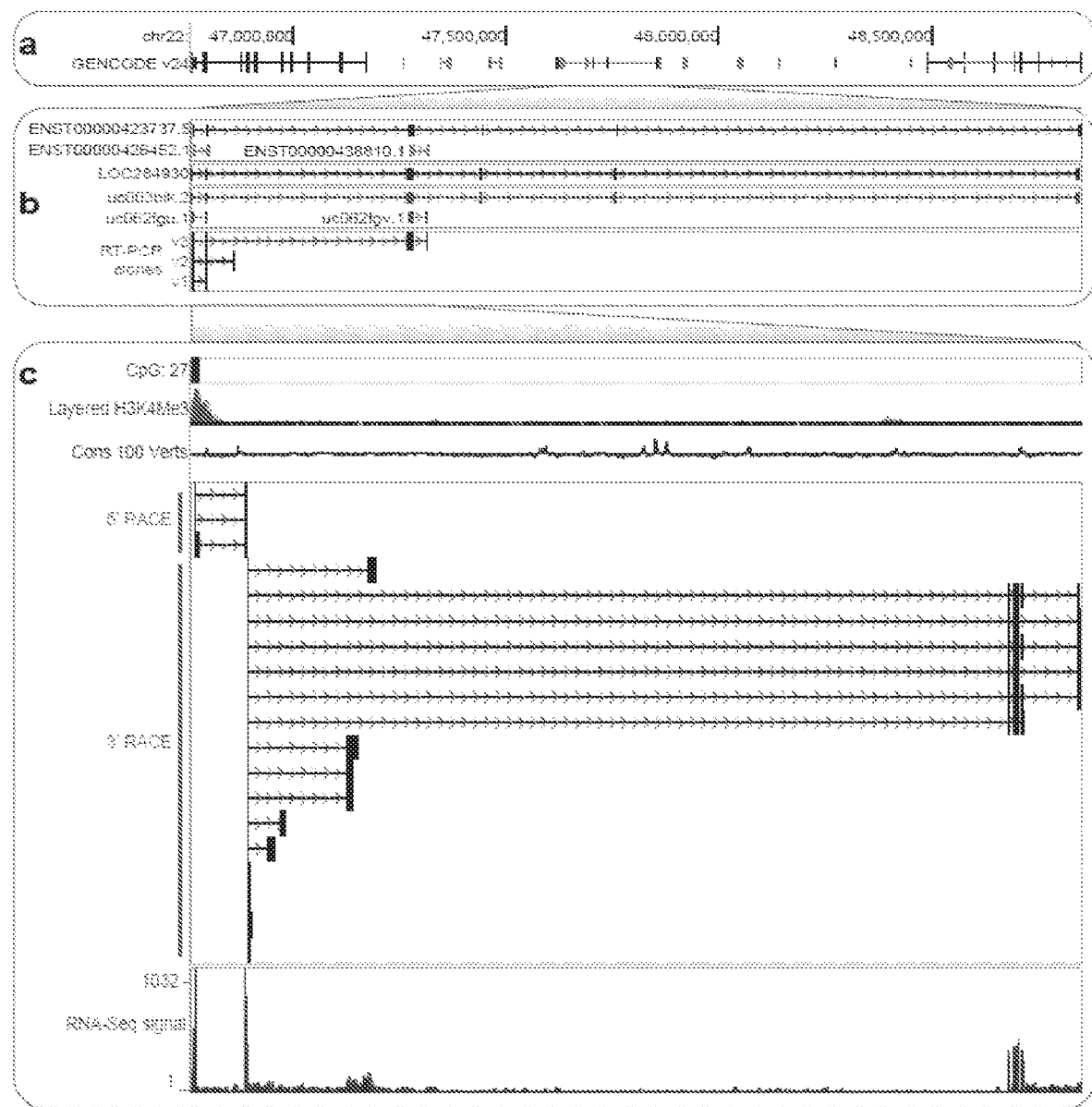
FIGS. 6A-6E FIG. 6A. Alignment of EPIC1 with UCSC browser. a. Genomic location of EPIC1 in GENCODE is highlighted in background. The nearest protein coding genes (upstream TBC1 D22A and downstream FAM19A5) are also shown in the two ends. b. EPIC1's gene structure, isoforms from GENCODE, RefSeq and UCSC annotation are enlarged. EPIC1 isoforms, i.e. v1, v2, and v3, are also listed in the window. c. The CpG island, H3K4Me3 signal from ENCODE project and conservation tracks are presented at top. Sequences derived from 5'RACE and 3'RACE are listed in red window. RNA-Seq signal from CCLE breast cancer cell lines are shown at bottom.
Figure 6B:
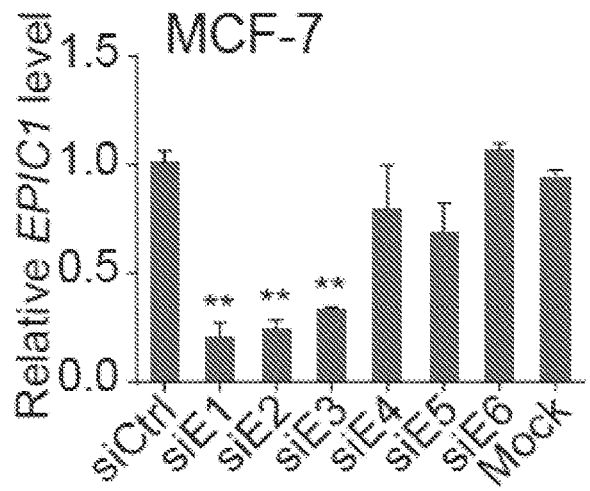
Figure 6C:
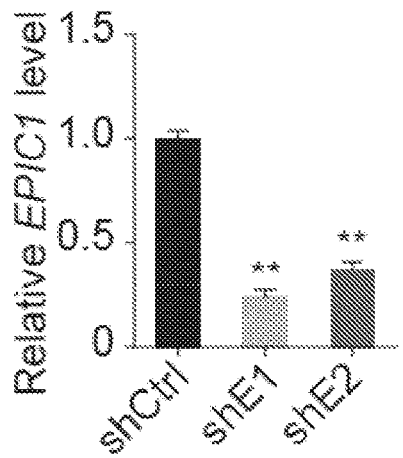
Figure 6D:
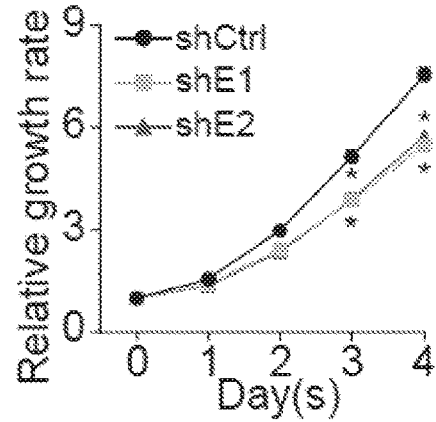
Figure 6E:
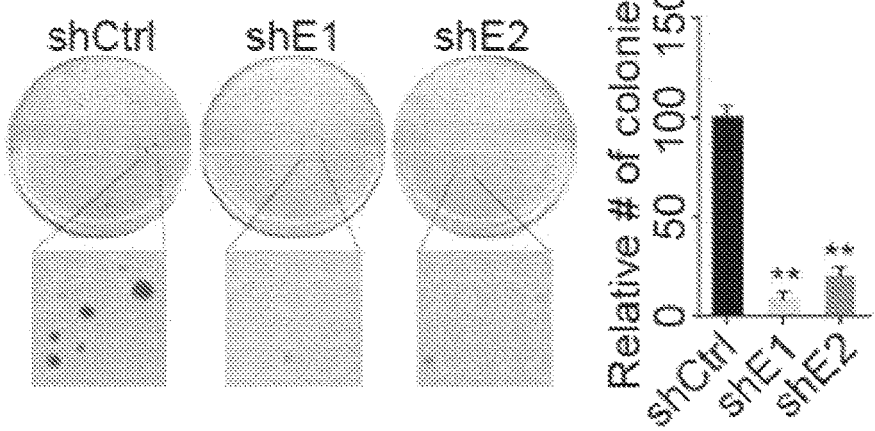
Figure 7A:
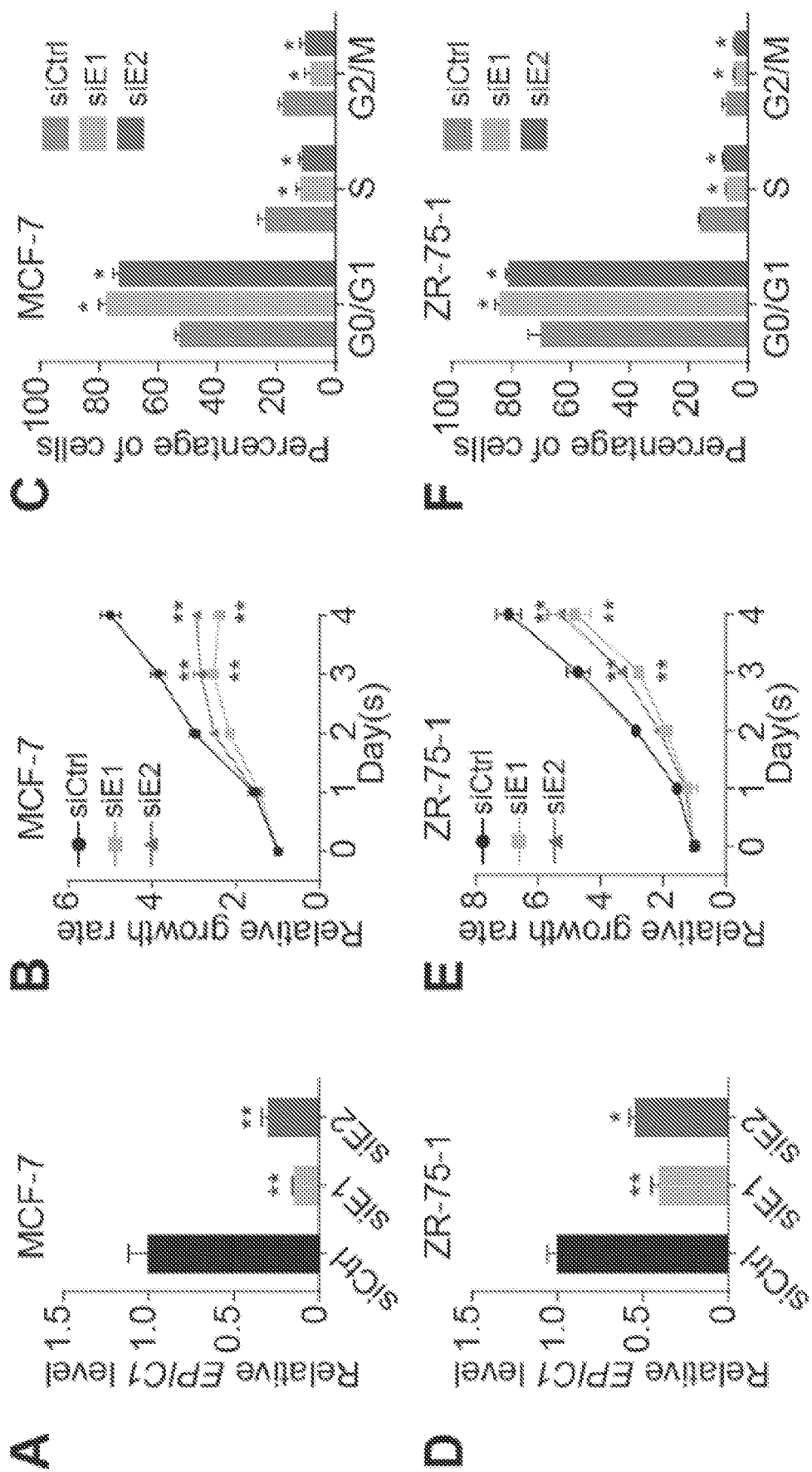
FIGS. 7A and 7B. EPIC1 Functions as an Oncogenic lncRNA in Breast Cancer (A-C) qRT-PCR analysis of EPIC1 (A), MTT assay (B), and cell-cycle analysis (C) in MCF-7 cells treated with EPIC1 siRNAs (siE1 and siE2). (D-F) qRT-PCR analysis of EPIC1 (D), MTT assay (E), and cell-cycle analysis (F) in ZR-75-1 cells treated with EPIC1 siRNAs. (G) Anchorage-independent colony formation assays of MCF-7 (left) and ZR-75-1 (right) cells treated with EPIC1 siRNAs. (H) Quantification of tumor growth in xenograft mouse models bearing with stable EPIC1 knockdown (shE1 and shE2) or control (shCtrl) MCF-7 cells. Error bars indicate means±SD, n=3 for technical replicates. *p<0.05, p<0.01. (I) Representative tumor size (left), and quantification of tumor weight (right) from xenograft mouse models. Data are presented as means±SD (n=10). p<0.01.
Figure 7B:
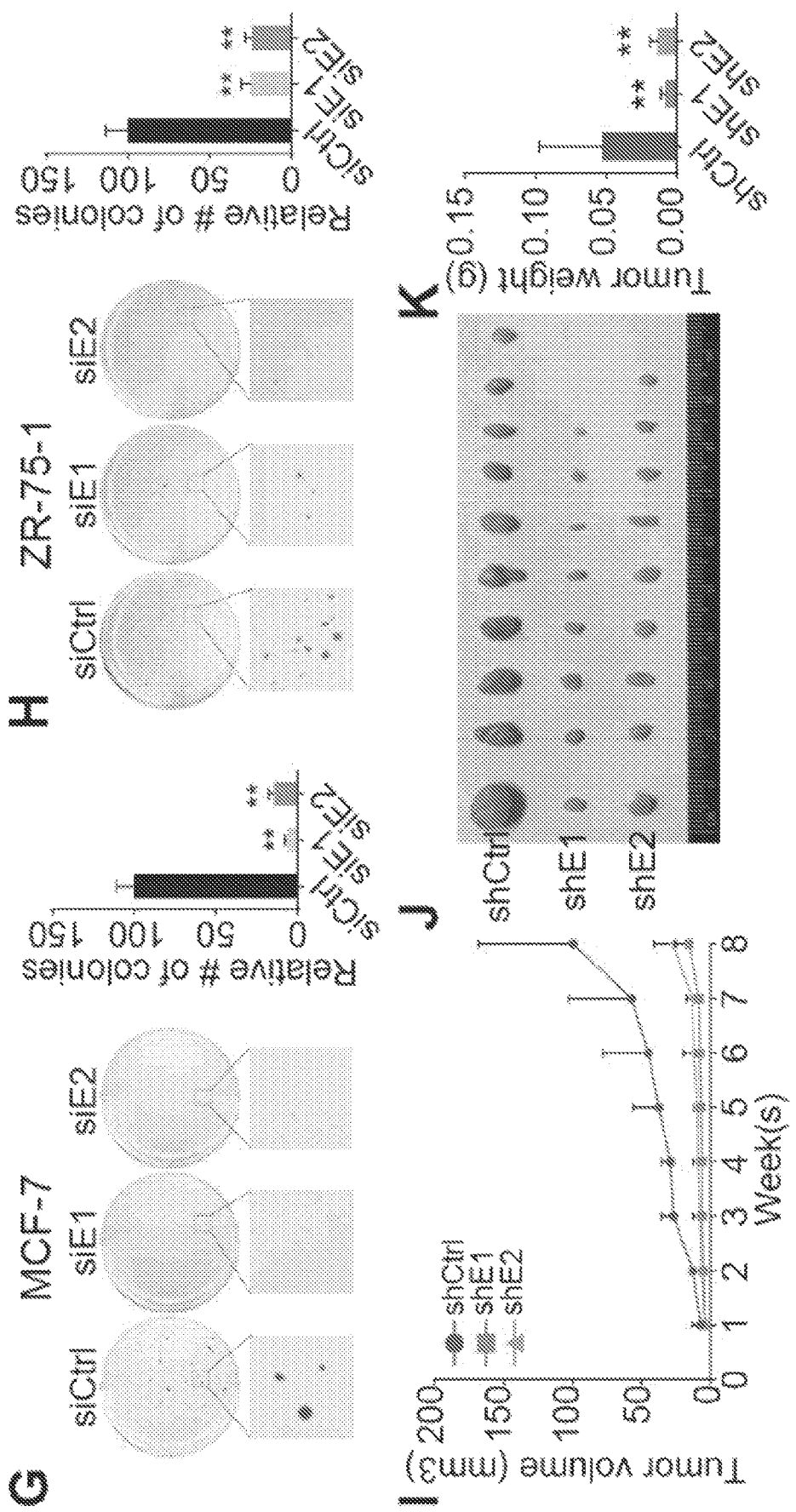

EPIC1 Functions as a Potential Oncogenic lncRNA by Promoting Cell-Cycle Progression: To evaluate the oncogenic role of EPIC1 in cancer, we analyzed the EPIC1 expression status in 28 cell lines across 8 cancer types using qRT-PCR. In agreement with EPIC1's activation in the luminal B breast cancer subtype, EPIC1 is overexpressed in luminal breast cancer cell lines (e.g., BT-474, MB361, MCF-7, ZR-75-1, and T-47D), along with ovarian cancer (A2780cis and OVCAR-4), pancreatic cancer (BxPC-3 and PANC-1), prostate cancer (PC-3), and leukemia (K562) cell lines. We further performed $5^{\circ}$-RACE and $3^{\circ}$-RACE cloning using total RNA from MCF-7 and T-47D cells to identify functional EPIC1 isoforms. Three splice variants of EPIC1 were cloned, including isoform v1 (567 nt), isoform v2 (844 nt), and isoform v3 (882 nt) (FIGS. 1 and 6A). All of them share same exon 1 and exon 2. We designed six siRNAs targeting shared sequence of all isoforms and screened three siRNAs that can readily knockdown EPIC1 expression (FIG. 6B). EPIC1 knockdown resulted in a decrease of cell proliferation in a time-dependent manner in luminal breast cancer cells MCF-7 and ZR-75-1 (FIGS. 7 (A-F)). Soft agar assays further demonstrated that EPIC1 knockdown significantly inhibits the anchorage-independent growth of cancer cells (FIG. 7 (G)). Moreover, cell-cycle analysis revealed that silencing of EPIC1 resulted in G0/G1 arrest in MCF-7 and ZR-75-1 cells (FIG. 7 (C, F)). Next, we established stable EPIC1 knockdown cells using lentiviral shRNAs. Both shEPIC1 stable cells exhibited significantly reduced cell proliferation (FIG. 6C), anchorage-independent growth (FIG. 6D), and in vivo xenograft growth (FIG. 6E), compared with the shCtrl cells. These results not only suggest oncogenic activity of EPIC1 in vivo, but also provide a potential therapeutic target for breast cancer treatment.

Figure 8A:
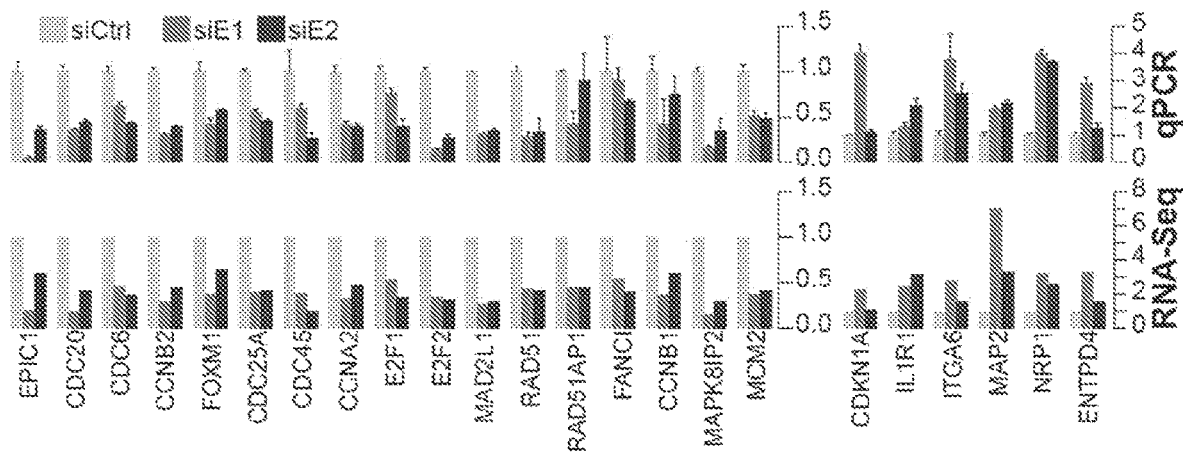
FIGS. 8A-8C EPIC1 Is a Nuclear lncRNA Regulating MYC Targets Expression (FIG. 8A) EPIC1-regulated gene expression by qRT-PCR analysis (top) and RNA-seq (bottom). Error bars indicate mean±SD, n=3 for technical replicates. Western blot of MYC-regulated targets in MCF-7 (FIG. 8B) and ZR-75-1 (FIG. 8C) cells treated with EPIC1 and MYC siRNAs.
Figures 8B, 8C:
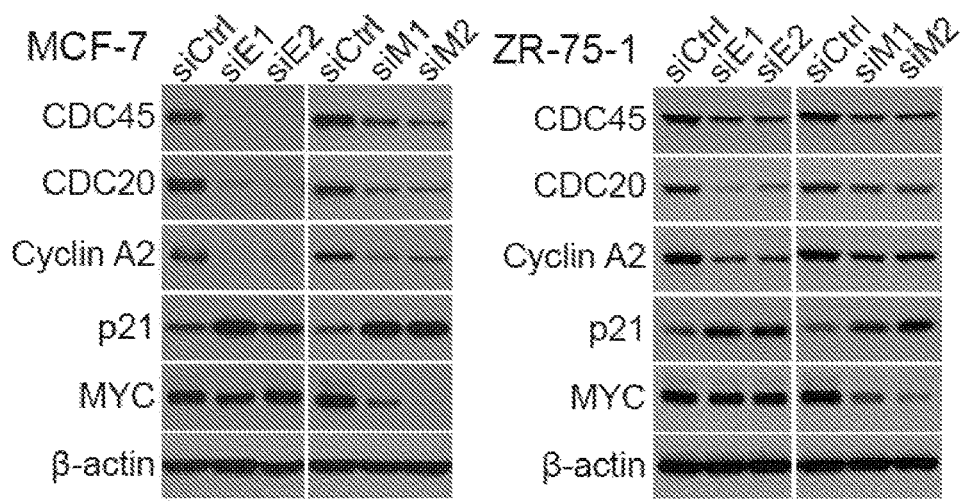

EPIC1 Is a Nuclear lncRNA that Regulates Myc Targets: Cell fractionation PCR and subcellular RNA-seq analyses revealed that EPIC1 RNA is predominately located in the nucleus, suggesting that EPIC1 might play a role in transcriptional regulation and chromatin interactions. To explore this possibility, RNA-seq analyses were performed on MCF-7 cells transfected with two siRNAs targeting EPIC1 individually or pooled. We have confirmed that both siRNAs can readily knockdown the level of nuclear EPIC1 RNA. To exclude possible off-target effects on gene expression associated with single siRNAs, we focused only on genes regulated in the same direction in all three transfection experiments. EPIC1 knockdown in MCF-7 cells resulted in the regulation of 805 genes (upregulation of 317 genes and downregulation of 488 genes), which are highly overlapped with 2,005 EPIC1-associated genes that were significantly correlated with EPIC1 expression across 559 TOGA breast tumors (p=2.6 3 $10^{-25}$). This overlap was even higher in the pathway analysis. Gene set enrichment analysis (GSEA) analysis showed that cell-cy-cle-related biological processes such as "Myc targets," "G2M checkpoint," and "E2F targets" were significantly enriched in the EPIC1-associated genes in 17 out of 20 cancer types. The same cellular processes were enriched in the EPIC1-regulated genes in MCF-7 cells. Among them, the Myc pathway/targets are prominent gene sets enriched with EPIC1-regulated genes in both tumor samples and cell lines. For example, the Myc targets CDC45, CDC20, and CCNA2 were significantly downregulated by EPIC1 knockdown. Moreover, CDKN1A (encoding the p21 protein) was significantly induced after EPIC1 knockdown (FIGS. 8A and 8B). p21 is a well-established negative regulator of cell-cycle progression at G1 and S phase that is directly inhibited by Myc. These observations are consistent with our observation that EPIC1 knockdown resulted in cancer cells' arrest at Go/Gi phase. Similarly, in MCF-7 and ZR-75-1 cells, Myc knockdown also led to a pattern of Myc target expression and cell growth comparable with EPIC1 knockdown (FIGS. 8B and 8C). This suggested that the oncogenic role of EPIC1 may be associated with Myc protein.

EPIC1 Interacts with the 148-220 Amino Acid Region of Myc through Its 129-283 nt Sequence: To study the interaction between EPIC1 RNA and Myc protein, we overexpressed each of three EPIC1 isoforms (v1, v2, and v3) with Flag-tagged Myc protein in 293T cells and performed RNA immunoprecipitation (RIP) assay. This analysis revealed that EPIC1 isoforms v1 and v2 could be enriched by Myc RIP. In v1 or v2 isoforms overexpressing MCF-7 cells, only the v1 isoform could regulate Myc target genes. We further observed that overexpression of the EPIC1 v1 isoform promoted Gi phase progression and in vivo xenograft growth. It is apparent to us that the v1 isoform is the functional isoform of EPIC1 gene in breast cancer. We therefore used isoform v1 (567 nt) as the reference sequence of EPIC1 in the following study.

Figure 9A:
Figure 9G:
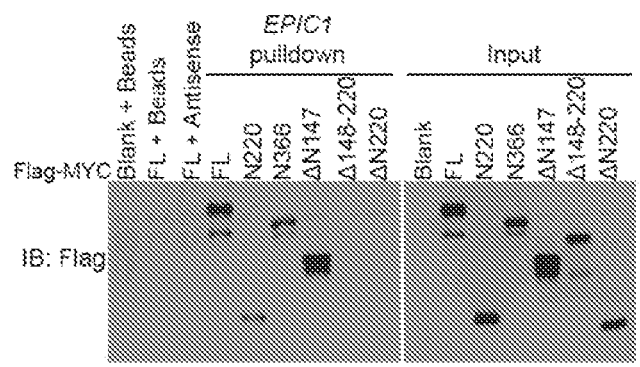
Figure 9H:
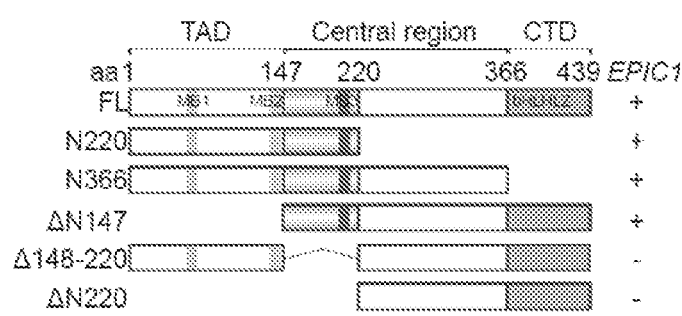

RNA pull-down assay showed that Myc protein could be co-precipitated by an in-vitro-transcribed biotinylated EPIC1 sense transcript, but not by the EPIC1 antisense transcript (FIG. 9A). Myc RIP with cell lysates from MCF-7 cells was then performed to confirm the interaction between endogenous EPIC1 and Myc protein (FIG. 9B). A well-documented Myc interacting lncRNA, PVT1 was included as positive control and could also be enriched by Myc RIP (FIG. 9B). Further in vitro binding assay using in-vitro-transcribed EPIC1 RNA and recombinant His-tagged Myc protein demonstrated that EPIC1 binds directly to Myc protein (FIG. 9C). To map the EPIC1 functional motifs corresponding to Myc binding, we conducted an in vitro RNA pull-down assay using a series of truncated EPIC1 fragments. This analysis revealed that nucleotides 1-358 of EPIC1 (EPIC1 1-358 nt) are sufficient to interact with Myc protein, while other EPIC1 truncated fragments could not (FIG. 9D). To map with greater precision the sequence of EPIC1 that binds to Myc, we further designed seven truncated or deletion mutants of the EPIC1 1-358 nt region and revealed that three deletion mutants (D121-180 nt, D181-240 nt, and D241-300 nt) can abolish EPIC1 binding to Myc protein. Deletion of all three regions (129-283 nt) also abolished EPIC1's interaction with Myc protein (named as DMyc-EPIC1; FIGS. 9E and 9F). These data suggested that the EPIC1 129-283 nt region is necessary for EPIC1's binding to the Myc protein. Myc protein domain mapping studies revealed that EPIC1 binds the 148-220 amino acid (aa) region of Myc, which is not overlapped with the well-characterized transcriptional activation domain and basic-helix-loop-helix domain of Myc protein (FIG. 9B (G, H)). Deletion of the 148-220 aa region of Myc protein (named as DEPIC1-Myc) abolished its interaction with EPIC1 (FIGS. 9G and 9H). Collectively, our findings demonstrated that EPIC1 interacts with the 148-220 aa region of Myc through its 129-283 nt sequence.

The Oncogenic Role of EPIC1 Partially Depends on Its Regulation of Myc Occupancy on Target Promoters: With the observation that EPIC1 directly interacts with Myc, we further analyzed the effect of EPIC1 on Myc target gene reporters (e.g., p21 and CCNA2 promoters) in MCF-7 cells. The reporter assays revealed that knockdown of either EPIC1 or Myc significantly regulates p21-Luc and CCNA2-Luc reporter luciferase activities. These observations indicate that EPIC1 directly regulates the expression of Myc targets through their promoter regions. Interestingly, EPIC1 knockdown had little effect on the expression of Myc (FIG. 8B), which led to our hypothesis that EPIC1 may regulate the transcriptional activity of the Myc protein.

Figure 10A:
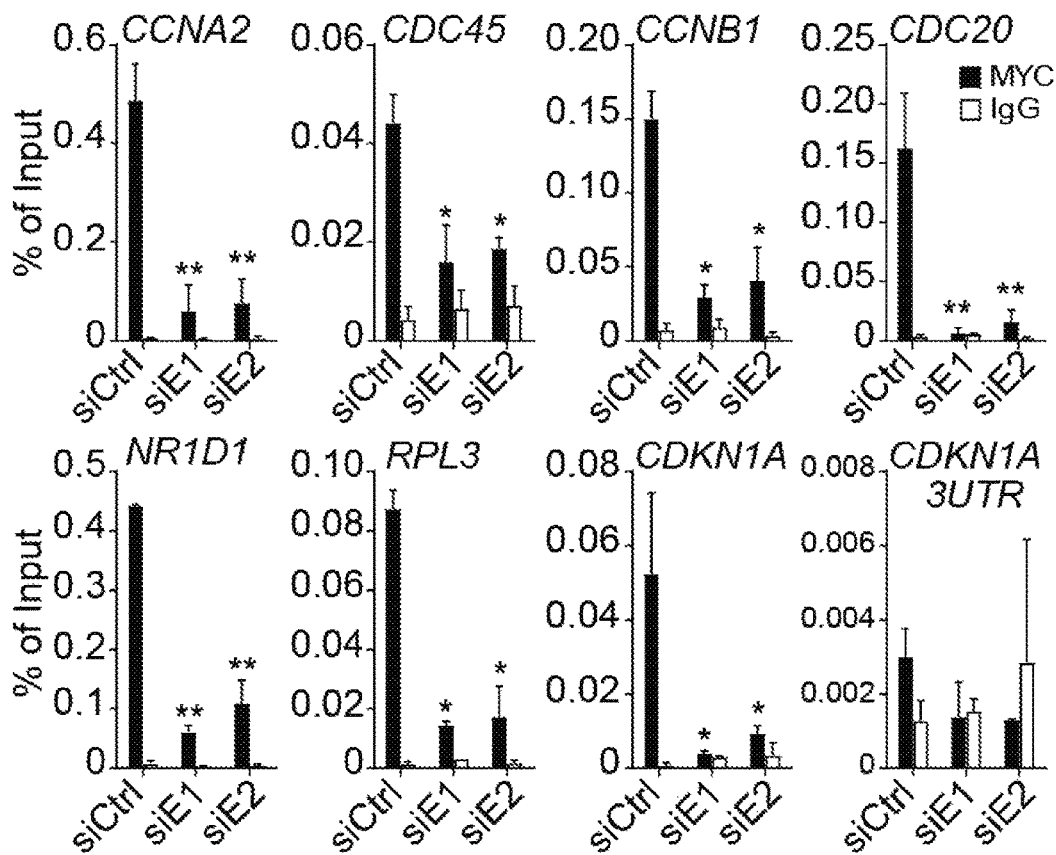
FIGS. 10A-10D. MYC Is Required for the Regulatory Role of EPIC1 in Cancer (FIG. 10A) ChIP-qPCR analysis of MYC occupancy on the promoters of target genes in MCF-7 cells treated with EPIC1 siRNAs.

To test this hypothesis, we performed an integrated analysis on Myc chromatin immunoprecipitation sequencing (ChIP-seq) data and RNA-seq data of EPIC1 knockdown MCF-7 cells. Among 805 EPIC1-regulated genes, 785 have robust Myc occupancy on their promoters in two biological replicates of MCF-7 ChIP-seq data. Interestingly, we did not observe a significant correlation between global Myc binding affinity and differential expression (i.e., fold change) after EPIC1 knockdown in MCF-7 cells, suggesting that EPIC1 may regulate Myc's occupancy on a specific group of targets. By further considering previously validated Myc targets, we identified 40 possible targets of the EPIC1-Myc regulatory axis. ChIP-qPCR were performed and validated that EPIC1 knock-down significantly reduces Myc's occupancies on the promoters of 26 targets, including CDKN1A (p21), CCNA2, CDC20, and CDC45 (FIG. 10A). It is known that Myc binds to DNA and functions as a transcription factor by heterodimerization with another transcription factor, MAX. Myc and MAX Co-IP assay in MCF-7 cells revealed that EPIC1 knockdown could moderately reduce the formation of Myc-MAX complexes. Moreover, overexpression of EPIC1, but not DMyc-EPIC1, could enhance the reporter luciferase activities mediated by Myc and MAX. These results suggest that EPIC1 promotes Myc's occupancy on EPIC1-regulated genes through its 129-283 nt sequence (Myc-binding sequence).

Figure 10B:
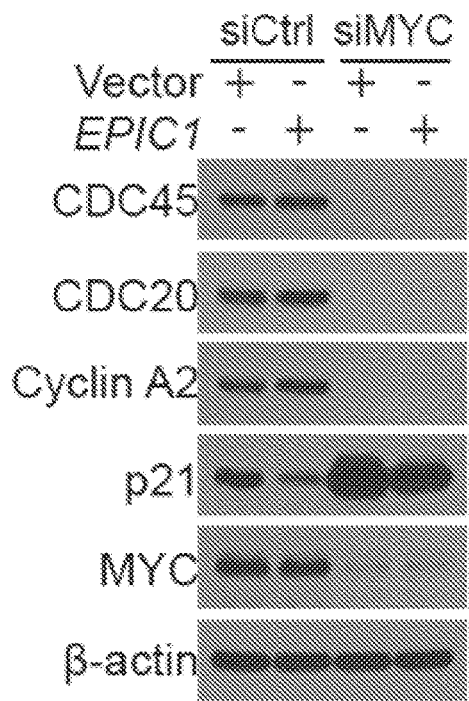
Figure 10C:
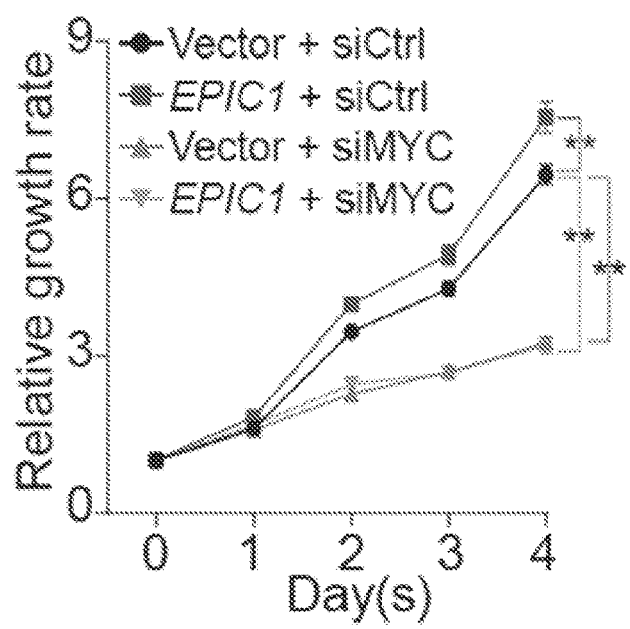
Figure 10D:
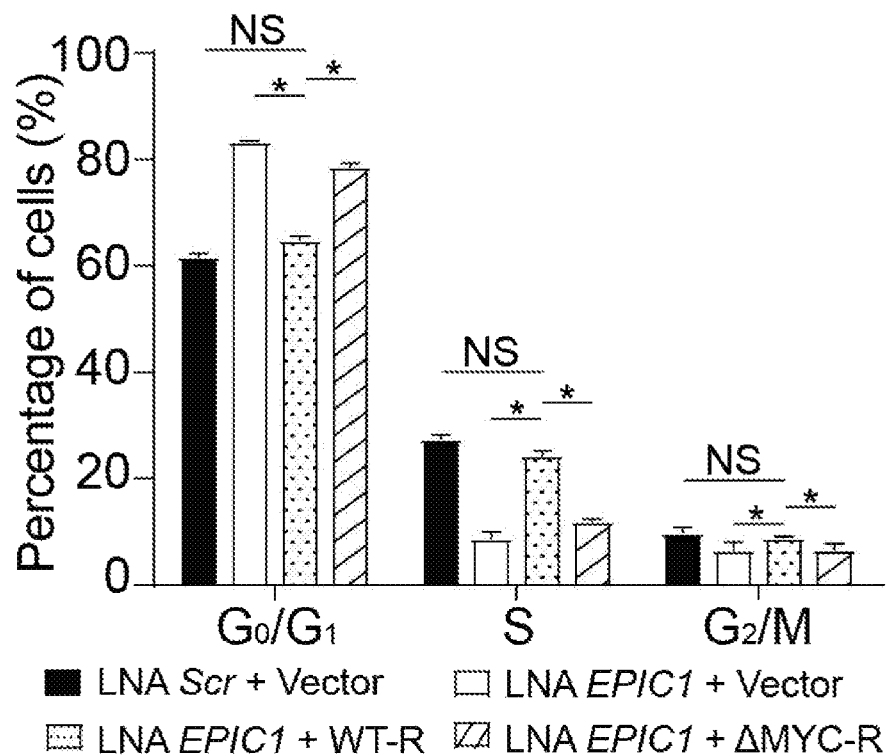

To further determine the role of the EPIC1-Myc regulatory axis in cancer, we performed the Myc knockdown in EPIC1 stably overexpressing MCF-7 cells and observed that EPIC1 regulation of cell proliferation and Myc target expression were attenuated by Myc knockdown (FIGS. 10B and 10C). Overexpression of Myc, but not EPIC1-binding-deficient mutant Myc proteins (DEPIC1-Myc), regulates CCNA2 and p21 expression. We further depleted the endogenous EPIC1 expression using locked nucleic acid (LNA) in MCF-7 cells, followed by overexpression of either LNA-resistant wild-type EPIC1 (WT-R-EPIC1) or deletion mutant of 129-283 nt Myc binding region (DMyc-R-EPIC1). Similar to EPIC1 siRNA treatment, LNA knockdown of EPIC1 significantly caused Gi arrest of MCF-7 cells, which could be rescued by reintroduction of full-length EPIC1, but not DMyc-EPIC1 (FIG. 10D). The expression of full-length and the truncated EPIC1s was confirmed to be comparable levels to rule out the influence of transfection efficiency. Consistently, LNA knockdown of EPIC1 also curtailed the expression of Myc target genes. Reintroduction of wild-type EPIC1, but not DMyc-EPIC1, was able to rescue the regulation of these genes. These results suggested that the oncogenic role of EPIC1 is at least in part dependent on its interaction with the Myc protein.

Example 2

We experimentally validate that EPIC1, the top predictive lncRNA for the Bromodomain and Extra-Terminal motif (BET) inhibitors, strongly promotes iBET762 and JQ-1 resistance through activating Myc transcriptional activity.

Methods

Cell culture, RNA interference, and real-time PCR. Human breast cancer cell lines, Hs578T, BT-474, and MCF-7, and human lung cancer cell line A549 were purchased from American Type Culture Collection (ATCC) and cultured as suggested by ATCC's guidelines. Human ovarian cancer cell line, A2780 and the cisplatin resistant version of the cell line, A2780cis, were obtained from the European Collection of Cell Cultures (ECACC), supplied by Sigma-Aldrich, and cultured in RPMI 1640 medium supplemented with 2 mM glutamine, 10% FBS, 1% penicillin, and 1% streptomycin; A2780cis cells were also supplemented with 1 µM cisplatin. Phoenix cells were kindly provided by Dr. Wen Xie (University of Pittsburgh) and maintained in Dulbecco's Modified Eagle's Medium supplemented with 10% FBS, 1% penicillin, and 1% streptomycin.

For RNA interference, cells were transfected with 40 nM siRNA targeting EPIC1, or control siRNA using Lipofectamine RNAiMAX (Thermo Fisher, #13778150) per the manufacturer's instructions. For quantitative real-time PCR (qRT-PCR) analysis, total RNA was isolated 72 h later using an RNeasy Mini kit (Qiagen, #74104) according to the manufacturer's instructions; cDNAs were synthesized from 0.5 µg of total RNA using a High-Capacity cDNA Reverse Transcription Kit (Applied Biosystems, #4368813). qRT-PCR was performed with Power SYBR Green PCR Master Mix (Applied Biosystems, #4367659) on a QuantStudio 6 Flex Real-Time PCR System (Applied Biosystems). Relative gene expression was determined by ΔΔCt normalized to GAPDH.

The following siRNAs (sense, antisense) were used as previously described:

```
EPIC1 siRNA_A#,
                            (SEQ ID NO: 10)
    CCUUCAGACUGUCUUUGAAdTdT, (SEQ ID NO: 11)
    UUCAAAGACAGUCUGAAGGdTdT;

EPIC1 siRNA_B#,
                            (SEQ ID NO: 12)
    GCUUUCUCUCGGAAACGUGdTdT, (SEQ ID NO: 13)
    CACGUUUCCGAGAGAAAGCdTdT;
```

```
EPIC1 siRNA_C#,
                                            (SEQ ID NO: 14)
AGUGUGGCCUCAGCUGAAAdTdT, (SEQ ID NO: 15)
UUUCAGCUGAGGCCACACUdTdT;

control siRNA,
                                            (SEQ ID NO: 16)
GUGCGUUGUUAGUACUAAUdTdT, (SEQ ID NO: 17)
AUUAGUACUAACAACGCACdTdT.
```

Sequences of primers for qRT-PCR were:

```
EPIC1 forward,
                                            (SEQ ID NO: 18)
TATCCCTCAGAGCTCCTGCT, EPIC1 reverse,
                                            (SEQ ID NO: 19)
AGGCTGGCAAGTGTGAATCT;

GAPDH forward,
                                            (SEQ ID NO: 20)
GGTGAAGGTCGGAGTCAACG,
and GAPDH reverse,
                                            (SEQ ID NO: 21)
TGGGTGGAATCATATTGGAACA.
```

Validation of lncRNA-drug predictive pairs in cell lines. MCF-7 cells (MCF-7/Vector and MCF-7/EPIC1) and A549 cells (A549/Vector and A549/EPIC1) stably expressing an empty vector and EPIC1 were established with retroviral particles using the previously published method. Briefly, full-length of EPIC1 was inserted into retroviral pBABE-lnc vector with AgeI and XhoI enzymes and the resulting construct was named as lnc-EPIC1. To establish stable EPIC1-expressing cells, 10 μg of pBABE-lnc or lnc-EPIC1 plasmids were transfected into a 10-cm culture dish of Phoenix cells to produce retroviral particles, and retroviruses were collected 48 hr post transfection. Then, cells were transduced for 24 hr with the retroviruses and selected with puromycin.

The ectopic expression level of EPIC1 in stable cells was confirmed using PCR. To validate lncRNA-Drug interactions, EPIC1 knockdown and overexpressed cells were seeded at 2000 cells per well in 96-well culture plates and incubate for overnight at 37° C., 5% $CO_2$. After treatment with a series of twofold diluted drugs (JQ-1 and I-BET-762) for 48 h, MTT assays were performed with a CellTiter 96 Non-Radioactive Cell Proliferation Assay Kit (Promega, #G410) following the manufacture's guidelines. The absorbance value was measured at 570 nm using an xMark Microplate Spectrophotometer (Bio-Rad) with a reference wavelength of 630 nm and the IC50 of JQ-1 and I-BET-762 on cells was calculated, respectively.

Results

EPIC1 as a master regulator of BET inhibitor resistance. The iBETs have been demonstrated to be a promising new therapy in several cancer types, including breast cancer. EPIC1 (Epigenetically induced lncRNA 1) is an intergenic lncRNA located on chromosome 22q13.31 and is highly overexpressed in 15 cancer types including BRCA. Using an lncRNA-based prediction model we developed, EPIC1 was identified as a top predictor of iBET resistance in a BRCA-specific iBET model. In the model, EPIC1 expression has a significant positive correlation with IC50s of iBET762 in breast cancer cell lines (rho=0.53, p=0.002, Spearman's correlation). Moreover, high expression of EPIC1 was also associated with poor survival in patients of BRCA (p=0.067, univariate Cox regression), UCEC (p=0.014), KIRC (p=0.0004) and COAD (p=0.052).

Figure 11A:
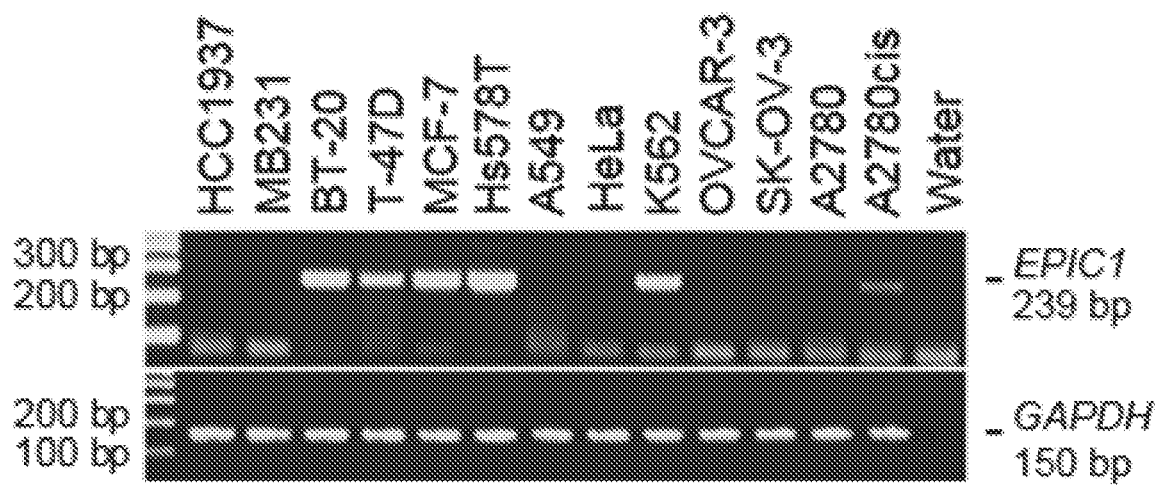
FIGS. 11A-11C EPIC1 overexpression enhances breast cancer cell lines resistance to BET inhibitors.
Figure 11B:
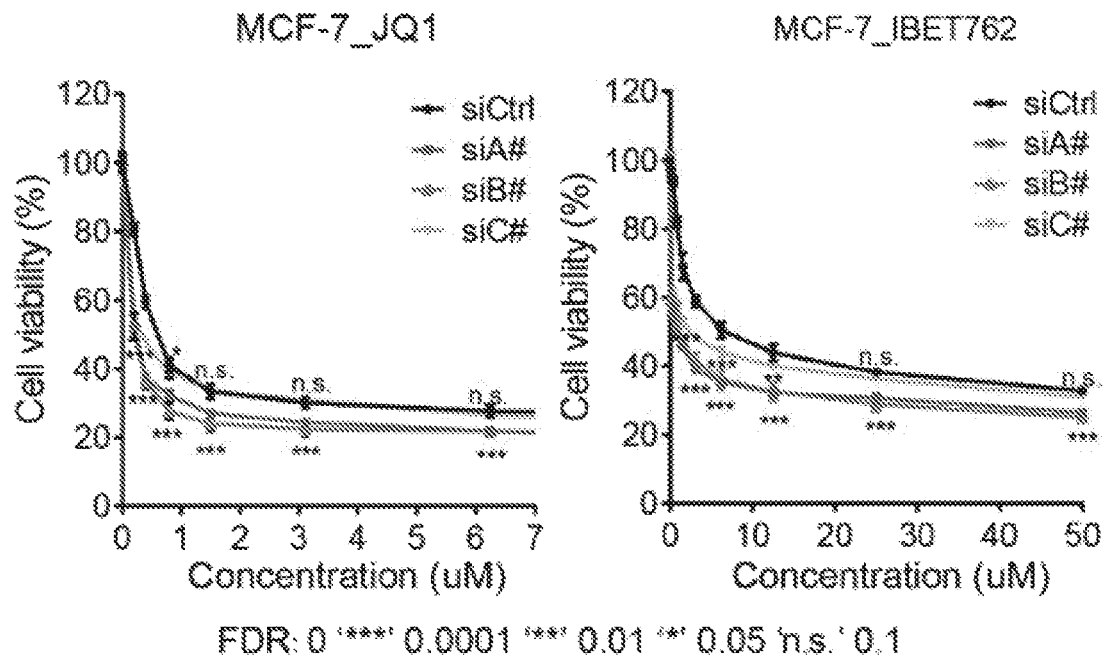
Figure 11C:
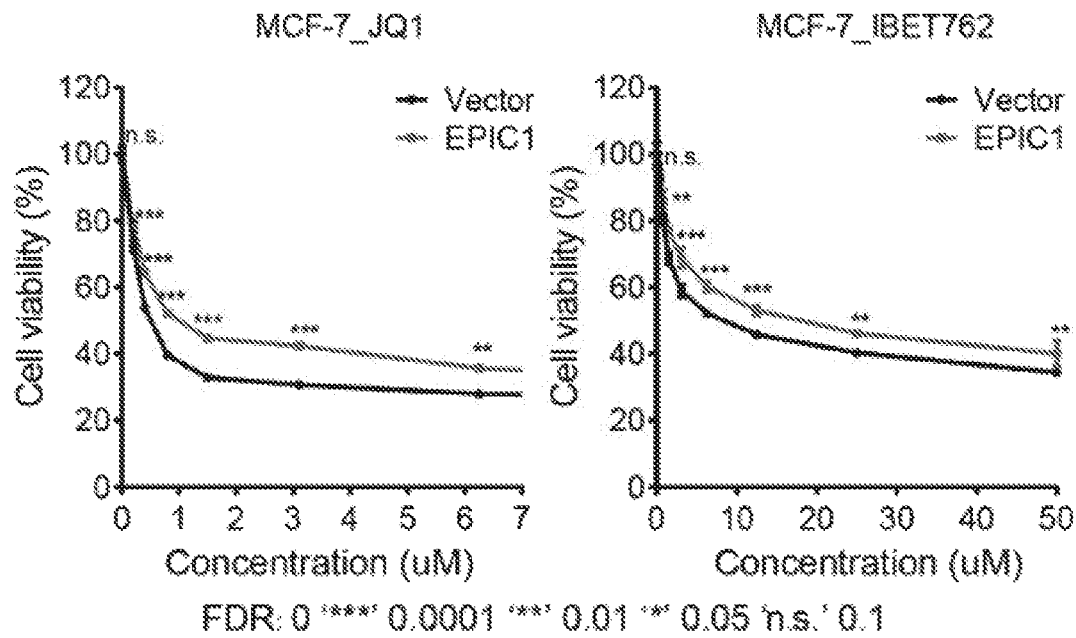

We designed primers to screen EPIC1's expression in 13 cell lines using RT-PCR (see Methods section). EPIC1 is upregulated in MCF-7, ZR-75-1, and Hs578T cell lines and is expressed at low levels in A549 cell line (FIG. 11A). To investigate the EPIC1's role in regulating the iBET response in cancer cell lines, we knocked down the EPIC1 expression in MCF-7, BT-474 and ZR-75-1 breast cancer cell lines with three EPIC1 siRNAs. Knockdown of EPIC1 significantly increased the iBETs sensitivity in MCF-7, BT-474, and ZR-75-1 cells (FIG. 11B). we further cloned the full-length human EPIC1 cDNA and overexpressed EPIC1 in MCF-7 breast cancer cells and A549 lung cancer cells. In accordance with our modeling prediction, overexpression of EPIC1 led to the drug resistance of iBET in MCF-7 and A549 cells (FIG. 11C).

To further explore the underlying mechanism of EPIC1 in regulating iBETs resistance, RNA-seq analyses were performed in four cancer cell lines including MCF-7 and Hs578T cells after EPIC1 knockdown by EPIC1 siRNAs, individually or pooled (GEO: GSE98538). We focused only on genes regulated in the same direction in all three transfections to exclude the possible siRNA off-target effects. EPIC1 knockdown in breast and ovarian cancer cells resulted in significant expression change of 4318 genes, which were significantly overlapped with EPIC1-correlated genes in 505 cancer cell lines (p <0.0001, two-side Fisher's exact test). Moreover, 16 out of 18 EPIC1-correlated pathways in 505 cancer cell lines are significantly regulated by EPIC1-knockdown (FDR<0.25, GSEA). Among them, the Myc pathway/targets are prominent gene sets enriched with EPIC1-associated genes in both cancer cell lines and EPIC1-knockdown cells. As described above, we have mechanistically demonstrated that EPIC1 regulates Myc transcriptional activity by directly interacting with Myc protein. Overexpression of EPIC1 increased Myc target expression and breast tumorigenesis in vitro and in vivo, which can be abolished by Myc knockdown. Our observations suggest that EPIC1 is an oncogenic lncRNA and also plays an important role in promoting the resistance to iBETs by increasing Myc protein's transcriptional activity.

The following numbered clauses outline various aspects of the present invention.

Clause 1. A method of reducing the occupancy of Myc protein to the promoters of its target genes in a cell, comprising knocking down or silencing EPigenetically Induced lnCRNA1 (EPIC1) levels in the cell with a nucleic acid or nucleic acid analog able to knock down expression of EPIC1.

Clause 2. The method of clause 1, wherein the nucleic acid or nucleic acid analog is an RNAi (RNA interference) agent, or an antisense agent (e.g., an ASO) that targets EPIC1.

Clause 3. The method of clause 1, wherein the nucleic acid or nucleic acid analog is an siRNA.

Clause 4. The method of clause 3, wherein the siRNA ranges from 20 to 25 bases in length, and comprises a sequence having at least 90% sequence identity, at least 95% sequence identity, or 100% sequence identity with SEQ ID NO: 4 (5'-CCUUCAGACUGUCUUUGAA-3).

Clause 5. The method of clause 3, wherein the siRNA ranges from 20 to 25 bases in length, and comprises a sequence having at least 90% sequence identity, at least 95% sequence identity, or 100% sequence identity with SEQ ID NO: 5 (5'-GCUUUCUCUCGGAAACGUG-3').

Clause 6. The method of clause 3, wherein the siRNA ranges from 20 to 25 bases in length, and comprises a sequence having at least 90% sequence identity, at least 95% sequence identity, or 100% sequence identity with SEQ ID NO: 6 (5'-AGUGUGGCCUCAGCUGAAA-3').

Clause 7. The method of any one of clauses 3-6, wherein the siRNA ranges from 20 to 29 bases in length.

Clause 8. The method of clause 3, wherein the siRNA has the sequence of SEQ ID NO: 4 (5'-CCUUCAGACUGU-CUUUGAA-3).

Clause 9. The method of clause 3, wherein the siRNA has the sequence of SEQ ID NO: 5 (5'-GCUUUCUCUCG-GAAACGUG-3').

Clause 10. The method of clause 3, wherein the siRNA has the sequence of SEQ ID NO: 6 (5'-AGUGUGGC-CUCAGCUGAAA-3').

Clause 11. The method of clause 1, wherein the nucleic acid or nucleic acid analog is an shRNA.

Clause 12. The method of clause 11, wherein the shRNA comprises a sequence having at least 90% sequence identity, at least 95% sequence identity, or 100% sequence identity with SEQ ID NO: 7 (5'-TGCCTTCA-GACTGTCTTTGAA-3').

Clause 13. The method of clause 11, wherein the shRNA comprises a sequence having at least 90% sequence identity, at least 95% sequence identity, or 100% sequence identity with SEQ ID NO: 8 (5'-GCTTTCTCTCG-GAAACGTGAA-3').

Clause 14. The method of clause 11, wherein the shRNA is produced in the cell by a gene encoding the shRNA.

Clause 15. The method of clause 14, wherein the shRNA is transferred into the cell in a recombinant viral genome or by gene editing.

Clause 16. The method of clause 15 wherein the shRNA is transferred into the cell in a recombinant retroviral or Adeno-associated virus genome.

Clause 17. The method of clause 1, wherein the nucleic acid or nucleic acid analog is a nucleic acid analog.

Clause 18. The method of clause 17, wherein the nucleic acid analog is a locked nucleic acid (LNA).

Clause 19. The method of clause 18, wherein the LNA comprises the sequence

Clause 20. 5'-GTCGACTCCTGCCGGA-3'.

Clause 21. The method of clause 18, wherein the LNA has the sequence

Clause 22. 5'-GTCGACTCCTGCCGGA-3'.

Clause 23. A method of treating cancer in a patient, comprising knocking down or silencing EPigenetically Induced lnCRNA1 (EPIC1) levels in a cancer cell of the patient with a nucleic acid or nucleic acid analog able to knock down expression of EPIC1.

Clause 24. The method of clause 21, wherein the nucleic acid or nucleic acid analog is an RNAi (RNA interference) agent, or an antisense agent that targets EPIC1.

Clause 25. The method of clause 21, wherein the nucleic acid or nucleic acid analog is an siRNA.

Clause 26. The method of clause 23, wherein the siRNA ranges from 20 to 25 bases in length, and comprises a sequence having at least 90% sequence identity, at least 95% sequence identity, or 100% sequence identity with SEQ ID NO: 4 (5'-CCUUCAGACUGUCUUUGAA-3).

Clause 27. The method of clause 23, wherein the siRNA ranges from 20 to 25 bases in length, and comprises a sequence having at least 90% sequence identity, at least 95% sequence identity, or 100% sequence identity with SEQ ID NO: 5 (5'-GCUUUCUCUCGGAAACGUG-3').

Clause 28. The method of clause 23, wherein the siRNA ranges from 20 to 25 bases in length, and comprises a sequence having at least 90% sequence identity, at least 95% sequence identity, or 100% sequence identity with SEQ ID NO: 6 (5'-AGUGUGGCCUCAGCUGAAA-3').

Clause 29. The method of any one of clauses 23-26, wherein the siRNA ranges from 20 to 29 bases in length.

Clause 30. The method of clause 23, wherein the siRNA has the sequence of SEQ ID NO: 4 (5'-CCUUCAGACUGU-CUUUGAA-3).

Clause 31. The method of clause 23, wherein the siRNA has the sequence of SEQ ID NO: 5 (5'-GCUUUCUCUCG-GAAACGUG-3').

Clause 32. The method of clause 23, wherein the siRNA has the sequence of SEQ ID NO: 6 (5'-AGUGUGGC-CUCAGCUGAAA-3').

Clause 33. The method of clause 21, wherein the nucleic acid or nucleic acid analog is an shRNA.

Clause 34. The method of clause 31, wherein the shRNA comprises a sequence having at least 90% sequence identity, at least 95% sequence identity, or 100% sequence identity with SEQ ID NO: 7 (5'-TGCCTTCA-GACTGTCTTTGAA-3').

Clause 35. The method of clause 31, wherein the shRNA comprises a sequence having at least 90% sequence identity, at least 95% sequence identity, or 100% sequence identity with SEQ ID NO: 8 (5'-GCTTTCTCTCG-GAAACGTGAA-3').

Clause 36. The method of clause 31, wherein the shRNA is produced in the cancer cell of the patient by a gene encoding the shRNA.

Clause 37. The method of clause 34, wherein the shRNA is transferred into the cancer cell of the patient in a recombinant viral genome or by gene editing.

Clause 38. The method of clause 34 wherein the shRNA is transferred into the cancer cell of the patient in a recombinant retroviral or Adeno-associated virus genome.

Clause 39. The method of clause 21, wherein the nucleic acid or nucleic acid analog is a nucleic acid analog.

Clause 40. The method of clause 37, wherein the nucleic acid analog is a locked nucleic acid (LNA).

Clause 41. The method of clause 38, wherein the LNA comprises the sequence

Clause 42. 5'-GTCGACTCCTGCCGGA-3'.

Clause 43. The method of clause 38, wherein the LNA has the sequence

Clause 44. 5'-GTCGACTCCTGCCGGA-3'.

Clause 45. The method of any one of clauses 21-40, wherein the cancer is a breast cancer, such as luminal B breast cancer, endometrial cancer, ovarian cancer, pancreatic cancer, or leukemia.

Clause 46. The method of any one of clauses 21-40, wherein the cancer is a cancer in which Myc is activated.

Clause 47. The method of any one of clauses 21-43, further comprising administering a chemotherapeutic agent to the patient when EPIC1 expression is knocked down or silenced (such that the chemotherapeutic agent is active in the patient when the EPIC1 expression is knocked down or silenced).

Clause 48. The method of clause 42, wherein the chemotherapeutic agent is a Bromodomain and Extra-Terminal motif (BET) inhibitor.

Clause 49. The method of clause 44, wherein the BET inhibitor is one or more of (+)–JQ1, I-BET151, PFI-1, I-BET-762, or Apabetalone.

Clause 50. The method of any one of clauses 21-45, further comprising: obtaining an RNA sample from a tumor biopsy of a patient; determining if the RNA sample has elevated EPIC1 RNA levels as compared to normal tissue from the patient; and, where levels of EPIC1 RNA levels are elevated, knocking down or silencing EPIC1 expression in the cancer cell of the patient Clause 51. A nucleic acid or nucleic acid analog comprising a sequence that has at least 95% sequence identity, at least 99% sequence identity, or 100% sequence identity with at least 15 contiguous bases of SEQ ID NO: 1, SEQ ID NO: 2, or SEQ ID NO: 3, or a sequence complementary thereto.

Clause 52. The nucleic acid or nucleic acid analog of clause 47, comprising a nucleic acid including a gene for expressing a sequence that has at least 95% sequence identity, at least 99% sequence identity, or 100% sequence identity with at least 15 contiguous bases of SEQ ID NO: 1, SEQ ID NO: 2, or SEQ ID NO: 3, or a sequence complementary thereto.

Clause 53. The nucleic acid or nucleic acid analog of clause 47, comprising a nucleic acid including a vector comprising a gene for expressing a sequence that has at least 95% sequence identity, at least 99% sequence identity, or 100% sequence identity with at least 15 contiguous bases of SEQ ID NO: 1, SEQ ID NO: 2, or SEQ ID NO: 3, or a sequence complementary thereto.

Clause 54. The nucleic acid or nucleic acid analog of clause 48 or 49, wherein the gene for expressing a sequence that has at least 95% sequence identity, at least 99% sequence identity, or 100% sequence identity with at least 15 contiguous bases of SEQ ID NO: 1, SEQ ID NO: 2, or SEQ ID NO: 3, or a sequence complementary thereto is an shRNA targeting EPIC1.

Clause 55. The nucleic acid or nucleic acid analog of clause 47, wherein the nucleic acid or nucleic acid analog is an antisense agent or an interfering RNA agent for knocking down or silencing EPIC1.

Clause 56. The nucleic acid or nucleic acid analog of clause 51, wherein the nucleic acid or nucleic acid analog is DNA or a nucleic acid analog.

Clause 57. The nucleic acid or nucleic acid analog of clause 51, wherein the nucleic acid or nucleic acid analog is an siRNA.

Clause 58. The nucleic acid or nucleic acid analog of clause 53, wherein the siRNA ranges from 20 to 25 bases in length, and comprises a sequence having at least 90% sequence identity, at least 95% sequence identity, or 100% sequence identity with SEQ ID NO: 4 (5'-CCUUCA-GACUGUCUUUGAA-3).

Clause 59. The nucleic acid or nucleic acid analog of clause 53, wherein the siRNA ranges from 20 to 25 bases in length, and comprises a sequence having at least 90% sequence identity, at least 95% sequence identity, or 100% sequence identity with SEQ ID NO: 5 (5'-GCUUUCU-CUCGGAAACGUG-3').

Clause 60. The nucleic acid or nucleic acid analog of clause 53, wherein the siRNA ranges from 20 to 25 bases in length, and comprises a sequence having at least 90% sequence identity, at least 95% sequence identity, or 100% sequence identity with SEQ ID NO: 6 (5'-AGUGUGGC-CUCAGCUGAAA-3').

Clause 61. The nucleic acid or nucleic acid analog of clause 53, wherein the siRNA has the sequence of SEQ ID NO: 4 (5'-CCUUCAGACUGUCUUUGAA-3).

Clause 62. The nucleic acid or nucleic acid analog of clause 53, wherein the siRNA has the sequence of SEQ ID NO: 5 (5'-GCUUUCUCUCGGAAACGUG-3').

Clause 63. The nucleic acid or nucleic acid analog of clause 53, wherein the siRNA has the sequence of SEQ ID NO: 6 (5'-AGUGUGGCCUCAGCUGAAA-3').

Clause 64. The nucleic acid or nucleic acid analog of clause 51, wherein the nucleic acid or nucleic acid analog is an shRNA.

Clause 65. The nucleic acid or nucleic acid analog of clause 60, wherein the shRNA comprises a sequence having at least 90% sequence identity, at least 95% sequence identity, or 100% sequence identity with SEQ ID NO: 7 (5'-TGCCTTCAGACTGTCTTTGAA-3').

Clause 66. The nucleic acid or nucleic acid analog of clause 60, wherein the shRNA comprises a sequence having at least 90% sequence identity, at least 95% sequence identity, or 100% sequence identity with SEQ ID NO: 8 (5'-GCTTTCTCTCGGAAACGTGAA-3').

Clause 67. The nucleic acid or nucleic acid analog of clause 51, wherein the nucleic acid or nucleic acid analog is an LNA.

Clause 68. The nucleic acid or nucleic acid analog of clause 63, wherein the LNA comprises the sequence 5'-GTCGACTCCTGCCGGA-3'.

Clause 69. The nucleic acid or nucleic acid analog of clause 63, wherein the LNA has the sequence 5'-GTCGACTCCTGCCGGA-3'.

Clause 70. The nucleic acid or nucleic acid analog of clause 47, comprising a sequence that has at least 95% sequence identity, at least 99% sequence identity, or 100% sequence identity with at least 25, 50, or 100 contiguous bases of SEQ ID NO: 1, SEQ ID NO: 2, or SEQ ID NO: 3, or a sequence complementary thereto.

Clause 71. The nucleic acid or nucleic acid analog of clause 47, comprising a sequence that has 100% sequence identity with at least 15, 20, or 25 contiguous bases of SEQ ID NO: 1, SEQ ID NO: 2, or SEQ ID NO: 3, or a sequence complementary thereto.

Clause 72. The nucleic acid or nucleic acid analog of clause 74, comprising a sequence that has at least 95% sequence identity, at least 99% sequence identity, or 100% sequence identity with at least 15 contiguous bases of SEQ ID NO: 1, SEQ ID NO: 2, and SEQ ID NO: 3, or a sequence complementary thereto.

Clause 73. The nucleic acid or nucleic acid analog of clause 47, comprising a sequence that has at least 95% sequence identity, at least 99% sequence identity, or 100% sequence identity with SEQ ID NO: 1, SEQ ID NO: 2, or SEQ ID NO: 3, or a sequence complementary thereto.

While the present invention is described with reference to several distinct embodiments, those skilled in the art may make modifications and alterations without departing from the scope and spirit. Accordingly, the above detailed description is intended to be illustrative rather than restrictive.

What is claimed is:

1. A method of reducing the occupancy of Myc protein to the promoters of its target genes in a cell or of treating cancer in a patient, comprising knocking down or silencing EPigenetically Induced lnCRNA1 (EPIC1) levels in the cell with a nucleic acid or nucleic acid analog able to knock down expression of EPIC1.

2. The method of claim 1, for treating cancer in a patient, comprising knocking down or silencing EPIC1 levels in a cancer cell of the patient with a nucleic acid or nucleic acid analog able to knock down expression of EPIC1.

3. The method of claim 1, wherein the nucleic acid or nucleic acid analog is an RNA interference RNAi agent that targets EPIC1 or an antisense agent that targets EPIC1.

4. The method of claim 1, wherein the nucleic acid or nucleic acid analog is an siRNA, and shRNA, or an antisense agent.

5. The method of claim 4, the nucleic acid or nucleic acid analog is an siRNA, optionally ranging from 20 to 29 bases in length, and optionally comprising a sequence having at least 90% sequence identity, at least 95% sequence identity, or 100% sequence identity with: SEQ ID NO: 4 (5'-CCUUCAGACUGUCUUUGAA-3'); SEQ ID NO: 5 (5'-GCUUUCUCUCGGAAACGUG-3'); or SEQ ID NO: 6 (5'-AGUGUGGCCUCAGCUGAAA-3'); or has the sequence of SEQ ID NO: 4 (5'-CCUUCAGACUGUCUUUGAA-3'); SEQ ID NO: 5 (5'-GCUUUCUCUCGGAAACGUG-3'); or SEQ ID NO: 6 (5'-AGUGUGGCCUCAGCUGAAA-3').

6. The method of claim 1, wherein the nucleic acid or nucleic acid analog is an shRNA, and optionally comprises a sequence having at least 90% sequence identity, at least 95% sequence identity, or 100% sequence identity with SEQ ID NO: 7 (5'-TGCCTTCAGACTGTCTTTGAA-3') or SEQ ID NO: 8 (5'-GCTTTCTCTCGGAAACGTGAA-3').

7. The method of claim 4, wherein the shRNA is produced in the cell by a gene encoding the shRNA.

8. The method of claim 4, wherein the shRNA is transferred into the cell in a recombinant viral genome or by gene editing.

9. The method of claim 1, wherein the nucleic acid or nucleic acid analog is a nucleic acid analog, and optionally is a locked nucleic acid (LNA), and optionally comprises or has the sequence 5'-GTCGACTCCTGCCGGA-3' (SEQ ID NO: 9), a sequence complementary thereto, or a sequence having at least 90% sequence identity, at least 95% sequence identity, or 100% sequence identity with 5'-GTCGACTCCTGCCGGA-3' (SEQ ID NO: 9), or a sequence complementary thereto.

10. The method of claim 2, wherein the shRNA is transferred into the cancer cell of the patient in a recombinant viral genome or by gene editing.

11. The method of claim 2, wherein the cancer is a breast cancer, such as luminal B breast cancer, endometrial cancer, ovarian cancer, pancreatic cancer, or leukemia.

12. The method of claim 2, wherein the cancer is a cancer in which Myc is activated.

13. The method of claim 2, further comprising administering a chemotherapeutic agent to the patient when EPIC1 expression is knocked down or silenced.

14. The method of claim 13, wherein the chemotherapeutic agent is a Bromodomain and Extra-Terminal motif (BET) inhibitor.

15. The method of claim 2, further comprising: obtaining an RNA sample from a tumor biopsy of a patient; determining if the RNA sample has elevated EPIC1 RNA levels as compared to normal tissue from the patient; and, where levels of EPIC1 RNA levels are elevated, knocking down or silencing EPIC1 expression in the cancer cell of the patient.

16. A nucleic acid or nucleic acid analog comprising a sequence that has at least 95% sequence identity, at least 99% sequence identity, or 100% sequence identity with at least 15 contiguous bases of SEQ ID NO: 1, SEQ ID NO: 2, or SEQ ID NO: 3, or a sequence complementary thereto; or a gene for expressing a sequence that has at least 95% sequence identity, at least 99% sequence identity, or 100% sequence identity with at least 15 contiguous bases of SEQ ID NO: 1, SEQ ID NO: 2, or SEQ ID NO: 3, or a sequence complementary thereto, wherein the nucleic acid or nucleic acid analog is:

an siRNA, optionally ranging from 20 to 29 bases in length, and optionally comprising a sequence having at least 90% sequence identity, at least 95% sequence identity, or 100% sequence identity with: SEQ ID NO: 4 (5'-CCUUCAGACUGUCUUUGAA-3'); SEQ ID NO: 5 (5'-GCUUUCUCUCGGAAACGUG-3'); or SEQ ID NO: 6 (5'-AGUGUGGCCUCAGCUGAAA-3'); or has the sequence of SEQ ID NO: 4 (5'-CCUUCAGACUGUCUUUGAA-3'); SEQ ID NO: 5 (5'-GCUUUCUCUCGGAAACGUG-3'); or SEQ ID NO: 6 (5'-AGUGUGGCCUCAGCUGAAA-3'); or an shRNA, that optionally comprises a sequence having at least 90% sequence identity, at least 95% sequence identity, or 100% sequence identity with SEQ ID NO: 7 (5'-TGCCTTCAGACTGTCTTTGAA-3') or SEQ ID NO: 8 (5'-GCTTTCTCTCGGAAACGTGAA-3').

17. The nucleic acid or nucleic acid analog of claim 16, wherein the nucleic acid or nucleic acid analog is a nucleic acid analog, and optionally is a locked nucleic acid (LNA), and optionally comprises or has the sequence 5'-GTCGACTCCTGCCGGA-3' (SEQ ID NO: 9), a sequence complementary thereto, or a sequence having at least 90% sequence identity, at least 95% sequence identity, or 100% sequence identity with 5'-GTCGACTCCTGCCGGA-3' (SEQ ID NO: 9), or a sequence complementary thereto.

18. The nucleic acid or nucleic acid analog of claim 16, comprising a sequence that has at least 95% sequence identity, at least 99% sequence identity, or 100% sequence identity with at least 25, 50, or 100 contiguous bases of SEQ ID NO: 1, SEQ ID NO: 2, and/or SEQ ID NO: 3, or a sequence complementary thereto.

19. The nucleic acid or nucleic acid analog of claim 16, comprising a sequence that has at least 95% sequence identity, at least 99% sequence identity, or 100% sequence identity with SEQ ID NO: 1, SEQ ID NO: 2, or SEQ ID NO: 3, or a sequence complementary thereto.

20. The method of claim 14, wherein the Bromodomain and Extra-Terminal motif (BET) inhibitor comprises (+)-JQ1, I-BET151, PFI-1, I-BET-762, Apabetalone, or any combination thereof.

* * * * *